United States Patent
Shekdar et al.

(10) Patent No.: US 9,534,035 B2
(45) Date of Patent: Jan. 3, 2017

(54) CELL LINES EXPRESSING ENAC AND METHODS USING THEM

(75) Inventors: Kambiz Shekdar, New York, NY (US); Jessica Langer, Highland Park, NJ (US); Dennis Sawchuk, Hoboken, NJ (US)

(73) Assignee: CHROMOCELL CORPORATION, North Brunswick, NJ (US)

( * ) Notice: Subject to any disclaimer, the term of this patent is extended or adjusted under 35 U.S.C. 154(b) by 854 days.

(21) Appl. No.: 12/864,295

(22) PCT Filed: Jan. 25, 2009

(86) PCT No.: PCT/US2009/031936
§ 371 (c)(1),
(2), (4) Date: Jul. 23, 2010

(87) PCT Pub. No.: WO2009/094610
PCT Pub. Date: Jul. 30, 2009

(65) Prior Publication Data
US 2010/0298167 A1    Nov. 25, 2010

Related U.S. Application Data

(60) Provisional application No. 61/062,371, filed on Jan. 25, 2008, provisional application No. 61/063,219, filed on Feb. 1, 2008.

(51) Int. Cl.
*C40B 30/06* (2006.01)
*C07K 14/705* (2006.01)
*G01N 33/68* (2006.01)

(52) U.S. Cl.
CPC ......... *C07K 14/705* (2013.01); *G01N 33/6872* (2013.01); *G01N 2500/10* (2013.01)

(58) Field of Classification Search
USPC .................... 435/325, 353, 354, 358, 366
See application file for complete search history.

(56) References Cited

U.S. PATENT DOCUMENTS

| | | | |
|---|---|---|---|
| 5,693,756 A | 12/1997 | Li et al. | |
| 6,692,965 B1 | 2/2004 | Shekdar | |
| 2005/0059094 A1* | 3/2005 | Servant et al. | 435/7.2 |
| 2006/0223117 A1 | 10/2006 | Moyer | |
| 2008/0153120 A1 | 6/2008 | LeCoutre et al. | |

FOREIGN PATENT DOCUMENTS

| | | |
|---|---|---|
| GB | 2 396 414 | 6/2004 |
| WO | WO9840516 | 9/1998 |
| WO | WO02087306 | 11/2002 |
| WO | WO2005014848 | 2/2005 |
| WO | WO 2004/072645 | 8/2006 |
| WO | WO 2006/082110 | 8/2006 |
| WO | WO2007092185 | 8/2007 |
| WO | WO 2008/009565 | 1/2008 |

OTHER PUBLICATIONS

Witkowski et al.; Conversion of b-ketoacyl synthase to a malonyl decarboxylase by replacement of the active site cysteine with glutamine; Biochemistry 38:11643-11650, (1999).*
Seffernick et al.; Melanine deaminase and atrazine chlorohydrolase: 98 percent identical but functionally different; J. Bacteriol. 183(8):2405-2410, 2001.*
Branden et al.; Introduction to Protein Structure, Garland Publishing Inc., New York, p. 247, (1991).*
Hanwell et al.; Trafficking and Cell Surface Stability of the Epithelial Na+ Channel Expressed in Epithelial Madin-Darby Canine Kidney Cells; The Journal of Biological Chemistry; vol. 277, No. 12, pp. 9772-9779, Mar. 22, 2002.*
NCBI Reference Sequence: NM_001038.4; updated Dec. 3, 2006.*
NCBI Reference Sequence: NM_000336.2; updated Jan. 31, 2007.*
NCBI Reference Sequence: NM_001039.2; updated Feb. 9, 2004.*
NCBI Reference Sequence: NM_011324.1; updated Jan. 14, 2007.*
NCBI Reference Sequence: NM_011325.1; updated Jan. 14, 2007.*
NCBI Reference Sequence: NM_011326.2; updated Nov. 17, 2006.*
NCBI Reference Sequence: NM_031548.2; updated Jan. 14, 2007.*
NCBI Reference Sequence: NM_012648.1; updated Nov. 17, 2006.*
NCBI Reference Sequence: NM_017046.1; updated Jan. 14, 2007.*
Bengrine et al.; Indirect Activation of the Epithelial Na+ Channel by Trypsin; The Journal of Biological Chemistry; vol. 282, No. 37, pp. 26884-26896, Sep. 14, 2007.*
Staub et al.; Regulation of stability and function of the epithelial Na+ channel (ENaC) by ubiquitination; The EMBO Journal vol. 16 No. 21 pp. 6325-6336, 1997.*
Chraibi et al., "Protease modulation of the activity of the epithelial sodium channel expressed in Xenopus oocytes," Journal of General Physiology, 111(1):127-138 (1998).
Gupta et al., "Heterologous expression of a mammalian epithelial sodium channel in yeast," FEBS Letters, 481(1):77-80 (2000).
Lin et al., "The gene expression of the amiloride-sensitive epithelial sodium channel alpha-subunit is regulated by antagonistic effects between glucocorticoid hormone and Ras pathways in salivary epithelial cells," Journal of Biological Chemistry, 274(31):21544-21554 (1999).

(Continued)

*Primary Examiner* — Antonio Galisteo Gonzalez
(74) *Attorney, Agent, or Firm* — Ropes & Gray LLP; Brian M. Gummow; Sabine U Epelbaum

(57) ABSTRACT

Cell lines that stably express ENaC and methods for using those cell lines are disclosed herein. The invention includes cell lines that express various subunit combinations and various proteolyzed isoforms of ENaC and techniques for creating cell lines. The ENaC-expressing cell lines are highly sensitive, physiologically relevant and produce consistent results.

39 Claims, 11 Drawing Sheets

(56) References Cited

OTHER PUBLICATIONS

Staruschenko et al., "Functional reconstitution of the human epithelial Na+ channel in a mammalian expression system," Methods in Molecular Biology, 337:3-13 (2006).

Volk et al., "Overexpression of the epithelial Na+ channel gamma subunit in collecting duct cells—Interactions of Liddle's mutations and steroids on expression and function," Journal of Biological Chemistry, 280(18): 18348-118354 (2005).

Zhang et al., "A Simple Statistical Parameter for Use in Evaluation and Validation of High Throughput Screening Assays," Journal of Biomolecular Screening, 4(2):67-73 (1999).

Allen et al., "A homogeneous high throughput nonradioactive method for measurement of functional activity of Gs-coupled receptors in membranes," Journal of Biomolecular Screening, 7(1):35-44 (2002).

Benjamin et al., "State-dependent compound inhibition of Nav1.2 sodium channels using the FLIPR Vm dye: on-target and off-target effects of diverse pharmacological agents," Journal of Biomolecular Screening, 11(1):29-39 (2006).

Benjamin et al., "Validation of a fluorescent imaging plate reader membrane potential assay for high-throughput screening of glycine transporter modulators," Journal of Biomolecular Screening, 10(4):365-373 (2005).

Caliper Life Sciences, "Calcium Flux Assays using the LabChip 3000," (10 pages), May 16, 2006.

Caliper Life Sciences, "HEK293 Calcium Flux Assay using the LabChip 3000," (4 pages), May 2008.

Dorn et al., "Evaluation of a high-throughput fluorescence assay method for HERG potassium channel inhibition," Journal of Biomolecular Screening, 10(4):339-347 (2005).

Drake et al., "Development of a homogeneous, fluorescence resonance energy transfer-based in vitro recruitment assay for peroxisome proliferator-activated receptor delta via selection of active LXXLL coactivator peptides," Analytical Biochemistry, 304(1):63-69 (2002).

Falconer et al., "High-throughput screening for ion channel modulators," Journal of Biomolecular Screening, 7(5):460-465 (2002).

Gao et al., "Miniaturization of a Calcium Mobilization Assay in 384 Well Format," SnAPPShots, available at www.corning.com (2009).

Graham et al., "Application of beta-galactosidase enzyme complementation technology as a high throughput screening format for antagonists of the epidermal growth factor receptor," Journal of Biomolecular Screening, 6(6):401-411 (2001).

Huang, "Development of a high throughput screening assay for mitochondrial membrane potential in living cells," Journal of Biomolecular Screening, 7(4):383-389 (2002).

Kizer, et al. "Reconstitution of stretch-activated cation channels by expression of the α-subunit of the epithelial sodium channel cloned from osteoblasts," PNAS Feb. 4, 1997 94(3):1013-1018.

Le Poul et al., "Adaptation of aequorin functional assay to high throughput screening," Journal of Biomolecular Screening, 7(1):57-65 (2002).

McDonald, et al. "Cloning and expression of the beta- and gamma-subunits of the human epithelial sodium channel," Am. J. Physiol. 1995; 268(5): C1157-C1163.

Miret et al.,"Multiplexed G-protein-coupled receptor Ca2+ flux assays for high-throughput screening," Journal of Biomolecular Screening, 10(8):780-787 (2005).

Shimkets, et al. "In vivo phosphorylation of the epithelial sodium channel," PNAS. Mar. 17, 1998 95(6):3301-3305.

Stucchi et al., "Evaluation of Ion Channels Activity Using the FLIPR System: FLIPR(tetra) and FLIPR(384) Performance," www.axxam.com, downloaded Jan. 9, 2009.

Stucchi et al., "Evaluation of Ion Channels Activity Using the FLIPR System: FLIPRTETRA and FLIPR384 Performance," The 9th International Conference and Exhibition on Drug Discovery, May 10, 2006.

Trivedi et al., "Cellular HTS assays for pharmacological characterization of Na(V)1.7 modulators," Assay and Drug Development Technologies, 6(2):167-179 (2008).

Trivedi et al., "Membrane Potential Assay to Identify Ion Channel Modulars," downloaded Jan. 9, 2009.

Voilley et al. "The lung amiloride-sensitive Na+ channel: Biophysical properties, pharmacology, ontogenesis, and molecular cloning," PNAS 1994; 91(1): 247-251.

Wagstaff et al., "High-throughput screening for norepinephrine transporter inhibitors using the FLIPRTetra," Journal of Biomolecular Screening, 12(3):436-441 (2007).

Waldmann et al. "Molecular Cloning and Functional Expression of a Novel Amiloride-sensitive Na$^+$ Channel," JBC 1995; 270(46): 27411-27414.

Wolff et al., "Comparative study of membrane potential-sensitive fluorescent probes and their use in ion channel screening assays," Journal of Biomolecular Screening, 8(5):533-543 (2003).

Woollhead et al., "Forskolin-induced Cell Shrinkage and Apical Translocation of Functional Enhanced Green Fluorescent Protein-Human αENaC in H441 Lung Epithelial Cell Monolayers," JBC vol. 281(8) 5158-5168 Feb. 24, 2006.

Xie et al , "Inhibition of ENaC by intracellular Cl$^-$ in an MDCK clone with high ENaC expression," Am J Physiol Renal Physiol 287: F722-F731, 2004.

Xin et al., "Evaluation of no-wash calcium assay kits: enabling tools for calcium mobilization," Journal of Biomolecular Screening, 12(5):705-714 (2007).

Zeissig et al, "Restoration of ENaC expression by glucocorticoid receptor transfection in human HT-29/B6 colon cells," BBRC. 344(4):1065-70, 2006.

Dirks et al., "Visualizing RNA molecules inside the nucleus of living cells," Methods, 29: 51-57 (2003).

\* cited by examiner

SEQUENCE LISTING

```
<160> NUMBER OF SEQ ID NOS: 25

<210> SEQ ID NO 1
<211> LENGTH: 2010
<212> TYPE: DNA
<213> ORGANISM: Homo sapiens

<400> SEQUENCE: 1
atggagggga acaagctgga ggagcaggac tctagccctc cacagtccac tccagggctc      60
atgaagggga acaagcgtga ggagcagggg ctgggcccccg aacctgcggc gccccagcag     120
cccacggcgg aggaggaggc cctgatcgag ttccaccgct cctaccgaga gctcttcgag     180
ttcttctgca acaacaccac catccacggc gccatccgcc tggtgtgctc ccagcacaac     240
cgcatgaaga cggccttctg ggcagtgctg tggctctgca ccttttggcat gatgtactgg     300 caattcggcc tgcttttcgg agagtacttc agctaccccg tcagcctcaa catcaacctc     360
```

```
aactcggaca agctcgtctt ccccgcagtg accatctgca ccctcaatcc ctacaggtac    420
ccggaaatta agaggagct ggaggagctg gaccgcatca cagagcagac gctctttgac    480
ctgtacaaat acagctcctt caccactctc gtggccggct cccgcagccg tcgcgacctg    540
cgggggactc tgccgcaccc cttgcagcgc ctgagggtcc cgcccccgcc tcacggggcc    600
cgtcgagccc gtagcgtggc ctccagcttg cgggacaaca accccaggt ggactggaag    660 gactggaaga tcggcttcca gctgtgcaac cagaacaaat cggactgctt ctaccagaca    720
tactcatcag gggtggatgc ggtgagggag tggtaccgct ccactacat caacatcctg    780 tcgaggctgc cagagactct gccatccctg gaggaggaca cgctgggcaa cttcatcttc    840
gcctgccgct tcaaccaggt ctcctgcaac caggcgaatt actctcactt tcaccaccg    900 atgtatggaa actgctatac tttcaatgac aagaacaact ccaacctctg gatgtcttcc    960
atgcctggaa tcaacaacgg tctgtccctg atgctgcgcg cagagcagaa tgacttcatt   1020
cccctgctgt ccacagtgac tggggcccgg gtaatggtgc acgggcagga tgaacctgcc   1080
tttatggatg atggtggctt aacttgcgg cctggcgtgg agacctccat cagcatgagg   1140
aaggaaaccc tggacagact tgggggcgat tatggcgact gcaccaagaa tggcagtgat   1200
gttcctgttg agaacctta cccttcaaag tacacacagc aggtgtgtat tcactcctgc   1260
ttccaggaga gcatgatcaa ggagtgtggc tgtgcctaca tcttctatcc gcggccccag   1320
aacgtggagt actgtgacta cagaaagcac agttcctggg ggtactgcta ctataagctc   1380
caggttgact tctcctcaga ccacctgggc tgtttcacca agtgccggaa gccatgcagc   1440
gtgaccagct accagctctc tgctggttac tcacgatggc cctcggtgac atcccaggaa   1500
tgggtcttcc agatgctatc gcgacagaac aattacaccg tcaacaacaa gagaaatgga   1560
gtggccaaag tcaacatctt cttcaaggag ctgaactaca aaaccaattc tgagtctccc   1620
tctgtcacga tggtcaccct cctgtccaac ctgggcagcc agtggagcct gtggttcggc   1680
tcctcggtgt tgtctgtggt ggagatggct gagctcgtct ttgacctgct ggtcatcatg   1740
ttcctcatgc tgctccgaag gttccgaagc cgatactggt ctccaggccg aggggcagg   1800 ggtgctcagg aggtagcctc caccctggca tcctccccctc cttcccactt ctgccccac   1860 cccatgtctc tgtccttgtc ccagccaggc cctgctccct ctccagcctt gacagcccct   1920 cccctgcct atgccaccct gggccccgc ccatctccag gggctctgc aggggccagt   1980 tcctccacct gtcctctggg ggggccctga                                      2010
```

<210> SEQ ID NO 2
<211> LENGTH: 1923
<212> TYPE: DNA
<213> ORGANISM: Homo sapiens

<400> SEQUENCE: 2

```
atgcacgtga agaagtacct gctgaagggc ctgcatcggc tgcagaaggg ccccggctac     60
acgtacaagg agctgctggt gtggtactgc gacaacacca cacccacgg ccccaagcgc    120 atcatctgtg agggggcccaa gaagaaagcc atgtggttcc tgctcaccct gctcttcgcc    180
gccctcgtct gctggcagtg gggcatcttc atcaggacct acttgagctg ggaggtcagc    240 gtctcccctct ccgtaggctt caagaccatg gacttccctg ccgtcaccat ctgcaatgct    300
agccccttca gtattccaa aatcaagcat ttgctgaagg acctggatga gctgatggaa    360
gctgtcctgg agagaatcct ggctcctgag ctaagccatg ccaatgccac caggaacctg    420
```

| | |
|---|---|
| aacttctcca tctggaacca cacaccctg gtccttattg atgaacggaa ccccaccac | 480 |
| cccatggtcc ttgatctctt tggagacaac cacaatggct taacaagcag ctcagcatca | 540 |
| gaaaagatct gtaatgccca cgggtgcaaa atggccatga gactatgtag cctcaacagg | 600 |
| acccagtgta ccttccggaa cttcaccagt gctacccagg cattgacaga gtggtacatc | 660 |
| ctgcaggcca ccaacatctt tgcacaggtg ccacagcagg agctagtaga gatgagctac | 720 |
| cccggcgagc agatgatcct ggcctgccta ttcggagctg agccctgcaa ctaccggaac | 780 |
| ttcacgtcca tcttctaccc tcactatggc aactgttaca tcttcaactg ggcatgaca | 840 |
| gagaaggcac ttccttcggc caaccctgga actgaattcg gcctgaagtt gatcctggac | 900 |
| ataggccagg aagactacgt ccccttcctt gcgtccacgg ccggggtcag gctgatgctt | 960 |
| cacgagcaga ggtcataccc cttcatcaga gatgagggca tctacgccat gtcggggaca | 1020 |
| gagacgtcca tcggggtact cgtggacaag cttcagcgca tgggggagcc ctacagcccg | 1080 |
| tgcaccgtga atggttctga ggtccccgtc caaaacttct acagtgacta caacacgacc | 1140 |
| tactccatcc aggcctgtct tcgctcctgc ttccaagacc acatgatccg taactgcaac | 1200 |
| tgtggccact acctgtaccc actgccccgt ggggagaaat actgcaacaa ccgggacttc | 1260 |
| ccagactggg cccattgcta ctcagatcta cagatgagcg tggcgcagag agagacctgc | 1320 |
| attggcatgt gcaaggagtc ctgcaatgac acccagtaca agatgaccat ctccatggct | 1380 |
| gactggcctt ctgaggcctc cgaggactgg atttttccacg tcttgtctca ggagcgggac | 1440 |
| caaagcacca atatcaccct gagcaggaag ggaattgtca agctcaacat ctacttccaa | 1500 |
| gaatttaact atcgcaccat tgaagaatca gcagccaata acatcgtctg gctgctctcg | 1560 |
| aatctgggtg ccagtttgg cttctggatg gggggctctg tgctgtgcct catcgagttt | 1620 |
| ggggagatca tcatcgactt tgtgtggatc accatcatca gctggtggc cttggccaag | 1680 |
| agcctacggc agcggcgagc ccaagccagc tacgctggcc caccgccac cgtggccgag | 1740 |
| ctggtggagg cccacaccaa ctttggcttc agcctgaca cggccccccg cagccccaac | 1800 |
| actgggccct accccagtga gcaggccctg cccatcccag gcaccccgcc ccccaactat | 1860 |
| gactccctgc gtctgcagcc gctggacgtc atcgagtctg acagtgaggg tgatgccatc | 1920 |
| taa | 1923 |

<210> SEQ ID NO 3
<211> LENGTH: 1950
<212> TYPE: DNA
<213> ORGANISM: Homo sapiens

<400> SEQUENCE: 3

| | |
|---|---|
| atggcacccg gagagaagat caaagccaaa atcaagaaga atctgcccgt gacgggccct | 60 |
| caggcgccga ccattaaaga gctgatgcgg tggtactgcc tcaacaccaa cacccatggc | 120 |
| tgtcgccgca tcgtggtgtc ccgcggccgt ctgcgccgcc tcctctggat cgggttcaca | 180 |
| ctgactgccg tggccctcat cctctggcag tgcgccctcc tcgtcttctc cttctatact | 240 |
| gtctcagttt ccatcaaagt ccacttccgg aagctggatt tccctgcagt caccatctgc | 300 |
| aacatcaacc cctacaagta cagcaccgtt cgccacttc tagctgactt ggaacaggag | 360 |
| accagagagg ccctgaagtc cctgtatggc tttccagagt cccggaagcg ccgagaggcg | 420 |
| gagtcctgga actccgtctc agagggaaag cagcctagat tctcccaccg gattccgctg | 480 |
| ctgatctttg atcaggatga aagggcaag gccaggact tcttcacagg gaggaagcgg | 540 |
| aaagtcggcg gtagcatcat tcacaaggct tcaaatgtca tgcacatcga gtccaagcaa | 600 |

```
gtggtgggat tccaactgtg ctcaaatgac acctccgact gtgccaccta caccttcagc    660
tcgggaatca atgccattca ggagtggtat aagctacact acatgaacat catggcacag    720
gtgcctctgg agaagaaaat caacatgagc tattctgctg aggagctgct ggtgacctgc    780
ttctttgatg gagtgtcctg tgatgccagg aatttcacgc ttttccacca cccgatgcat    840
gggaattgct atactttcaa caacagagaa atgagacca ttctcagcac ctccatgggg     900
ggcagcgaat atgggctgca agtcattttg tacataaacg aagaggaata caacccattc    960
ctcgtgtcct ccactggagc taaggtgatc atccatcggc aggatgagta tcccttcgtc   1020
gaagatgtgg aacagagat tgagacagca atggtcacct ctataggaat gcacctgaca    1080
gagtccttca agctgagtga gccctacagt cagtgcacgg aggacgggag tgacgtgcca   1140
atcaggaaca tctacaacgc tgcctactcg ctccagatct gccttcattc atgcttccag   1200
acaaagatgg tggagaaatg tgggtgtgcc cagtacagcc agcctctacc tcctgcagcc   1260
aactactgca actaccagca gcaccccaac tggatgtatt gttactacca actgcatcga   1320
gcctttgtcc aggaagagct gggctgccag tctgtgtgca aggaagcctg cagctttaaa   1380
gagtggacac taaccacaag cctggcacaa tggccatctg tggtttcgga agtggttg     1440 ctgcctgttc tcacttggga ccaaggccgg caagtaaaca aaaagctcaa caagacagac   1500
ttggccaaac tcttgatatt ctacaaagac ctgaaccaga gatccatcat ggagagccca   1560
gccaacagta ttgagatgct tctgtccaac ttcggtggcc agctgggcct gtggatgagc   1620
tgctctgttg tctgcgtcat cgagatcatc gaggtcttct tcattgactt cttctctatc   1680
attgcccgcc gccagtggca aaagccaag gagtggtggg cctggaaaca ggctccccca    1740
tgtccagaag ctccccgtag cccacagggc caggacaatc cagccctgga tatagacgat   1800
gacctaccca cttttcaactc tgctttgcac ctgcctccag ccctaggaac ccaagtgccc   1860
ggcacaccgc ccccaaaata caataccttg cgcttggaga gggccttttc caaccagctc   1920
acagataccc agatgctgga tgagctctga                                    1950

<210> SEQ ID NO 4
<211> LENGTH: 2100
<212> TYPE: DNA
<213> ORGANISM: Rattus sp.

<400> SEQUENCE: 4
atgatgctgg accacaccag agcccctgag ctcaacattg acctagacct tcacgcctcc     60
aactcgccta aggggtccat gaagggcaac caattcaagg agcaagaccc ttgtcctcct    120
cagcccatgc aaggactggg gaaggggac aaacgtgaag agcagggcct gggcccggaa     180 cctcagcac cccggcagcc caccgaggag gaggaggcac tgattgagtt ccaccgctcc     240
taccgggagc tcttccagtt cttctgcaac aacaccacca tccacggggc catccgcctg    300
gtgtgctcca acacaaccg catgaagacg gccttctggg cggtgctgtg gctgtgcacc    360
ttcggcatga tgtactggca gttcgccttg ctgttcgagg agtacctcag ctacccagtg    420
agcctcaaca tcaacctcaa ttcagacaag ctggtcttcc ctgccgtcac tgtctgcacc    480
cttaatcctt acagatacac tgaaattaaa gaggagctgg aagagctgga ccgcatcacg    540
gagcagacgc tttttgactt gtacaaatac aactcttcct acactcgcca ggctggggcc    600
cgacgccgca gctcccgcga cctcctgggt gctttcccgc acccccctgca cgcgcctcgc   660 actccacctc cgcccctactc cggccgcacg gcgcgcagcg ggtcttccag cgtacgcgac   720
```

```
aacaatcccc aagtggaccg aaggactgg aagatcggct tccaactgtg caaccagaac      780
aaatcagact gtttctacca gacatactcc tctggggtgg atgcagtgag ggagtggtac      840
cgcttccatt acatcaacat tctgtccagg ctgtcggaca cctcgcccgc tctagaggaa      900
gaagccctgg gcaacttcat cttcacctgt cgcttcaacc aggcccctg caaccaggcg      960 aattattcca agttccacca ccccatgtac gggaactgct acactttcaa tgacaagaac     1020
aactccaatc tctggatgtc ctccatgcct ggagtcaaca atggtttgtc cctgacactg     1080
cgcacagagc agaatgactt catcccctg ctgtccacag tgacggggc cagggtgatg      1140 gtgcatggtc aggatgagcc tgcctttatg gatgatggtg gcttcaactt gaggcctggc     1200
gtggagacct ccatcagtat gagaaaggaa gccctggaca gcctcggagg aaattacggc     1260
gactgtactg agaatggtag cgatgtcccg gtcaagaacc tttacccttc caagtataca     1320
cagcaggtgt gcattcactc ctgcttccag gagaacatga tcaagaagtg tggctgtgcc     1380
tacatcttct accctaagcc caagggagtt gagttctgtg actaccgaaa gcagagctcc     1440
tggggctatt gctattataa actgcagggc gccttctcct tggacagcct gggctgtttc     1500
tccaagtgtc ggaagccttg tagtgtgatc aactacaaac tctctgccgg ctactcacgg     1560
tggccatctg tgaagtccca ggattggatc ttcgagatgc tgtccttgca gaacaattac     1620
actattaaca caaaagaaa cggagttgca aagctcaaca tcttcttcaa ggagctgaac     1680
tataaaacta attcggagtc tccttctgtc acgatggtca gctcctgtc caacctgggc     1740 agccagtgga gcctgtggtt tggctcgtcc gtgctctctg tggtggagat ggcggagctc     1800
atcttcgacc tcctggtcat cacacttctc atgctgctac gccggttccg gagccggtac     1860
tggtctccag gacgaggggc caggggtgcc agggaggtgg cctccactcc agcttcctcc     1920
ttcccgtccc gtttctgtcc tcaccctaca tccccaccac cttctttgcc ccagcagggc     1980
atgacccctc ccctggccct gacagcccct ccacctgcct atgctactct aggccccagt     2040
gcccctccac tggactctgc ggcgcctgac tgttctgcct gtgccctggc ggcgctctga     2100
```

<210> SEQ ID NO 5
<211> LENGTH: 1917
<212> TYPE: DNA
<213> ORGANISM: Rattus sp.

<400> SEQUENCE: 5

```
atgccagtga agaagtacct gctgaagtgc ctgcacaggc tgcagaaggg cccaggctac       60
acctacaagg agctgctagt gtggtactgc aacaacacca acacacacgg ccccaaacgc      120
atcatctgcg aggggcccaa gaagaaggcc atgtggttcc tgctcacgct gctcttcgcc      180
tgcctggtgt gctggcagtg gggcgtcttc atccagacct acctgagctg ggaggtcagc      240
gtctcgctct ccatgggctt caagaccatg aacttcccag cagtcaccgt ctgcaattcc      300
agccccttcc agtactccaa ggtcaagcac ttgctgaagg acttgtacaa gctgatggag      360
gctgtcctgg acaagattct ggctccgaag tccagccaca ccaacaccac cagtaccctg      420
aactttacca tctggaacca cacgcccctg gtccttattg atgagcggaa ccctgaccat      480
ccagtggtcc tcaacttgtt tgggacagca caacagca gcaacccagc cccaggaagc      540
acctgtaatg cccaagggtg caaagtggcc atgaggctgt gcagtgccaa tgggaccgtg      600
tgtaccttcc gaaacttcac cagtgccacc caggccgtga ctgagtggta catcctgcag      660
gccaccaaca tcttctcaca agtgctcccc caggacctgg tggggatggg ctatgctcct      720
gatcgcataa tcctagcctg tctgtttgga acggagccct gcagtcatcg gaacttcaca      780
```

```
cctatcttct accctgatta tggcaactgc tacatcttca actggggcat gacagagaag      840
gcacttcctt ctgccaaccc tgggactgaa tttggtctca agttgatcct ggacattggt      900
caggaggact atgtccsctt ccttgcgtcc acagcagggg ctaggctgat gctccacgag      960
cagaggacat accccttcat tagagaagag ggcatctatg ccatggcagg aactgagact     1020
tctattgggg tgctgctgga caagctgcag ggcaaggggg agccatacag tccctgcacc     1080
atgaacggcc ccgacgttgc cattcagaac ctctacagtg actacaacac gacctattcc     1140
atccaggcct gccttcattc ctgtttccaa gaccacatga tccataactg cagctgtggt     1200
cactacttgt accctttgcc tgctggggag aaatactgca acaacagaga cttcccagac     1260
tgggcctact gctacctaag cctacagatg agtgtggtcc agagagagac ctgcctcagc     1320
atgtgcaagg agtcctgcaa cgacacccag tataagatga ccatctccat ggctgactgg     1380
ccatccgagg cctctgagga ttggatccta catgtcctgt ctcaggagcg ggaccagagc     1440
tcaaatatca ccctgagcag gaagggtatt gtcaagctca atatctactt ccaagagttc     1500
aactaccgta ccatcgagga atcgccggcc aacaatatcg tgtggctgct ctctaacctg     1560
ggtggccagt ttggcttctg gatgggggc tcggtgctgt gcctcattga gtttggggag     1620
atcattatcg acttcatttg gatcactgtc atcaagctag tggcctcctg taaaggcctg     1680
cgcaggaggc ggccacagcg accctacact ggcccgccgc ccactgtggc cgagctggtg     1740
gaggcccaca ccaactgtgt cttccagcct gacacaacca gctgcaggcc caatgccgag     1800
gtctaccctg accaacagac tctgcccatt ccgggcactc cacctcccaa ctatgactcc     1860
ctgaggctgc agccgctgga caccatggag tctgacagcg aggtggaggc catctag       1917

<210> SEQ ID NO 6
<211> LENGTH: 1953
<212> TYPE: DNA
<213> ORGANISM: Rattus sp.

<400> SEQUENCE: 6
atggcgcctg agagaagat caaagccaaa atcaaaaaga atctgccggt tcgaggcccc       60
caggcaccaa ccattaagga cctgatgcat tggtactgca tgaacaccaa cacccacggg      120
tgccgccgca tcgtggtgtc ccaggccgc cttcggcctc tgctgtggat cgcgttcacg      180
ctaactgcag tggcccctcat tatctggcag tgcgccctcc tcgtcttctc tttctacacc      240
gtctctgtct ccatcaaagt ccacttccag aaactggatt ccctgccgt cactatctgc      300 aatatcaacc cttacaagta cagtgctgtg agtgaccttc tgactgactt ggacagtgag      360
acaaaacagg ccttgctgtc cttgtatggg gtcaagaat ctcggaaacg ccgggaagca      420
ggatccatgc cgtccacctt ggaaggcaca ccacccagat tcttcaaact gatcccactg      480
ctggtcttca atgagaatga aagggaaag gccagggact tcttcactgg ccggaagcgg      540
aaaatcagcg ggaaaatcat tcacaaagct ctaatgtca tgcacgttca tgagtcgaag      600
aaactggtgg gatttcaatt gtgctcaaat gataccctg actgcgccac ctacaccttc      660
agctcaggaa tcaatgccat ccaggagtgg tacaagcttc actacatgaa atcatggca      720 caggtgcctc tagagaagaa aatcaacatg agctattctg ccgaagaact gctggtgacc      780
tgcttcttcg atgggatgtc ctgtgatgcc aggaacttca cgcttttcca ccatccaatg      840
tatgggaact gctacacatt taacaacaaa gaaaatgcca ccatcctcag cacctccatg      900
ggaggcagtg agtacgggct gcaagtcatc ttatacataa acgaagatga atacaacccc      960
```

```
ttcctggtgt cctccactgg agccaaggtg cttatccatc agcagaatga ataccccttc    1020
atcgaagacg tggggatgga gatcgagaca gcaatgtcca cttccatagg aatgcacctg    1080
acagaatcct tcaagctgag cgaaccttac agccagtgca cagaggacgg cagtgatgtg    1140
cccgtcacaa acatctacaa cgctgcctac tccctccaga tctgccttta ttcatgcttc    1200
caaacaaaga tggtggaaaa atgtggctgc gcccagtaca ccagcctct gcctccagca    1260 gccaattact gcaactacca gcaacacccc aactggatgt attgctacta ccagttgtac    1320
caggcctttg tccgggaaga actgggctgc caatcagtgt gcaagcaatc ctgtagcttt    1380
aaggaatgga cactgaccac cagcttggca caatggccgt ctgaggcttc cgagaaatgg    1440
ttgctgaatg ttctcacctg ggaccaaagc cagcaaataa acaaaaagct caacaagact    1500
gacctggcca agctcttgat attctacaaa gacctgaacc aaagatccat catggagagc    1560
ccagccaaca gtattgagat gctcctgtcc aactttggtg acagctcgg cctgtggatg    1620 agctgttcag tcgtctgtgt cattgaaatc attgaagtct tcttcattga cttcttctct    1680
atcatcgccc gccgtcagtg gcacaaagcc aaggattgtt gggcccgtag gcagacaccg    1740
ccctccactg agactccctc cagccggcaa ggccaggata atccagctct ggatacggac    1800
gatgacctgc ccacttttac ctctgctatg cgcctgcctc cagcccgggg gtccacggtg    1860
cctggcacac cacctcccag atacaatacc ttgcgcttgg atagagcctt ttcatcccag    1920
ctcacagaca ctcagttgac caatgagttg taa                                 1953

<210> SEQ ID NO 7
<211> LENGTH: 669
<212> TYPE: PRT
<213> ORGANISM: Homo sapiens

<400> SEQUENCE: 7

Met Glu Gly Asn Lys Leu Glu Glu Gln Asp Ser Ser Pro Pro Gln Ser
1               5                   10                  15

Thr Pro Gly Leu Met Lys Gly Asn Lys Arg Glu Glu Gln Gly Leu Gly
                20                  25                  30

Pro Glu Pro Ala Ala Pro Gln Gln Pro Thr Ala Glu Glu Glu Ala Leu
            35                  40                  45

Ile Glu Phe His Arg Ser Tyr Arg Glu Leu Phe Glu Phe Phe Cys Asn
        50                  55                  60

Asn Thr Thr Ile His Gly Ala Ile Arg Leu Val Cys Ser Gln His Asn
65                  70                  75                  80

Arg Met Lys Thr Ala Phe Trp Ala Val Leu Trp Leu Cys Thr Phe Gly
                85                  90                  95

Met Met Tyr Trp Gln Phe Gly Leu Leu Phe Gly Glu Tyr Phe Ser Tyr
                100                 105                 110

Pro Val Ser Leu Asn Ile Asn Leu Asn Ser Asp Lys Leu Val Phe Pro
            115                 120                 125

Ala Val Thr Ile Cys Thr Leu Asn Pro Tyr Arg Tyr Pro Glu Ile Lys
        130                 135                 140

Glu Glu Leu Glu Glu Leu Asp Arg Ile Thr Glu Gln Thr Leu Phe Asp
145                 150                 155                 160

Leu Tyr Lys Tyr Ser Ser Phe Thr Thr Leu Val Ala Gly Ser Arg Ser
                165                 170                 175

Arg Arg Asp Leu Arg Gly Thr Leu Pro His Pro Leu Gln Arg Leu Arg
            180                 185                 190

Val Pro Pro Pro Pro His Gly Ala Arg Arg Ala Arg Ser Val Ala Ser
```

-continued

```
            195                 200                 205
Ser Leu Arg Asp Asn Asn Pro Gln Val Asp Trp Lys Asp Trp Lys Ile
210                 215                 220
Gly Phe Gln Leu Cys Asn Gln Asn Lys Ser Asp Cys Phe Tyr Gln Thr
225                 230                 235                 240
Tyr Ser Ser Gly Val Asp Ala Val Arg Glu Trp Arg Phe His Tyr
            245                 250                 255
Ile Asn Ile Leu Ser Arg Leu Pro Glu Thr Leu Pro Ser Leu Glu Glu
            260                 265                 270
Asp Thr Leu Gly Asn Phe Ile Phe Ala Cys Arg Phe Asn Gln Val Ser
            275                 280                 285
Cys Asn Gln Ala Asn Tyr Ser His Phe His His Pro Met Tyr Gly Asn
            290                 295                 300
Cys Tyr Thr Phe Asn Asp Lys Asn Asn Ser Asn Leu Trp Met Ser Ser
305                 310                 315                 320
Met Pro Gly Ile Asn Asn Gly Leu Ser Leu Met Leu Arg Ala Glu Gln
            325                 330                 335
Asn Asp Phe Ile Pro Leu Leu Ser Thr Val Thr Gly Ala Arg Val Met
            340                 345                 350
Val His Gly Gln Asp Glu Pro Ala Phe Met Asp Asp Gly Gly Phe Asn
            355                 360                 365
Leu Arg Pro Gly Val Glu Thr Ser Ile Ser Met Arg Lys Glu Thr Leu
            370                 375                 380
Asp Arg Leu Gly Gly Asp Tyr Gly Asp Cys Thr Lys Asn Gly Ser Asp
385                 390                 395                 400
Val Pro Val Glu Asn Leu Tyr Pro Ser Lys Tyr Thr Gln Gln Val Cys
            405                 410                 415
Ile His Ser Cys Phe Gln Glu Ser Met Ile Lys Glu Cys Gly Cys Ala
            420                 425                 430
Tyr Ile Phe Tyr Pro Arg Pro Gln Asn Val Glu Tyr Cys Asp Tyr Arg
            435                 440                 445
Lys His Ser Ser Trp Gly Tyr Cys Tyr Tyr Lys Leu Gln Val Asp Phe
            450                 455                 460
Ser Ser Asp His Leu Gly Cys Phe Thr Lys Cys Arg Lys Pro Cys Ser
465                 470                 475                 480
Val Thr Ser Tyr Gln Leu Ser Ala Gly Tyr Ser Arg Trp Pro Ser Val
            485                 490                 495
Thr Ser Gln Glu Trp Val Phe Gln Met Leu Ser Arg Gln Asn Asn Tyr
            500                 505                 510
Thr Val Asn Asn Lys Arg Asn Gly Val Ala Lys Val Asn Ile Phe Phe
            515                 520                 525
Lys Glu Leu Asn Tyr Lys Thr Asn Ser Glu Ser Pro Ser Val Thr Met
            530                 535                 540
Val Thr Leu Leu Ser Asn Leu Gly Ser Gln Trp Ser Leu Trp Phe Gly
545                 550                 555                 560
Ser Ser Val Leu Ser Val Val Glu Met Ala Glu Leu Val Phe Asp Leu
            565                 570                 575
Leu Val Ile Met Phe Leu Met Leu Leu Arg Arg Phe Arg Ser Arg Tyr
            580                 585                 590
Trp Ser Pro Gly Arg Gly Gly Arg Gly Ala Gln Glu Val Ala Ser Thr
            595                 600                 605
Leu Ala Ser Ser Pro Pro Ser His Phe Cys Pro His Pro Met Ser Leu
610                 615                 620
```

```
Ser Leu Ser Gln Pro Gly Pro Ala Pro Ser Pro Ala Leu Thr Ala Pro
625                 630                 635                 640

Pro Pro Ala Tyr Ala Thr Leu Gly Pro Arg Pro Ser Pro Gly Gly Ser
            645                 650                 655

Ala Gly Ala Ser Ser Ser Thr Cys Pro Leu Gly Gly Pro
            660                 665

<210> SEQ ID NO 8
<211> LENGTH: 640
<212> TYPE: PRT
<213> ORGANISM: Homo sapiens

<400> SEQUENCE: 8

Met His Val Lys Lys Tyr Leu Leu Lys Gly Leu His Arg Leu Gln Lys
1               5                   10                  15

Gly Pro Gly Tyr Thr Tyr Lys Glu Leu Leu Val Trp Tyr Cys Asp Asn
                20                  25                  30

Thr Asn Thr His Gly Pro Lys Arg Ile Ile Cys Glu Gly Pro Lys Lys
            35                  40                  45

Lys Ala Met Trp Phe Leu Leu Thr Leu Leu Phe Ala Ala Leu Val Cys
50                  55                  60

Trp Gln Trp Gly Ile Phe Ile Arg Thr Tyr Leu Ser Trp Glu Val Ser
65                  70                  75                  80

Val Ser Leu Ser Val Gly Phe Lys Thr Met Asp Phe Pro Ala Val Thr
                85                  90                  95

Ile Cys Asn Ala Ser Pro Phe Lys Tyr Ser Lys Ile Lys His Leu Leu
            100                 105                 110

Lys Asp Leu Asp Glu Leu Met Glu Ala Val Leu Glu Arg Ile Leu Ala
        115                 120                 125

Pro Glu Leu Ser His Ala Asn Ala Thr Arg Asn Leu Asn Phe Ser Ile
130                 135                 140

Trp Asn His Thr Pro Leu Val Leu Ile Asp Glu Arg Asn Pro His His
145                 150                 155                 160

Pro Met Val Leu Asp Leu Phe Gly Asp Asn His Asn Gly Leu Thr Ser
                165                 170                 175

Ser Ser Ala Ser Glu Lys Ile Cys Asn Ala His Gly Cys Lys Met Ala
            180                 185                 190

Met Arg Leu Cys Ser Leu Asn Arg Thr Gln Cys Thr Phe Arg Asn Phe
        195                 200                 205

Thr Ser Ala Thr Gln Ala Leu Thr Glu Trp Tyr Ile Leu Gln Ala Thr
210                 215                 220

Asn Ile Phe Ala Gln Val Pro Gln Gln Glu Leu Val Glu Met Ser Tyr
225                 230                 235                 240

Pro Gly Glu Gln Met Ile Leu Ala Cys Leu Phe Gly Ala Glu Pro Cys
                245                 250                 255

Asn Tyr Arg Asn Phe Thr Ser Ile Phe Tyr Pro His Tyr Gly Asn Cys
            260                 265                 270

Tyr Ile Phe Asn Trp Gly Met Thr Glu Lys Ala Leu Pro Ser Ala Asn
        275                 280                 285

Pro Gly Thr Glu Phe Gly Leu Lys Leu Ile Leu Asp Ile Gly Gln Glu
290                 295                 300

Asp Tyr Val Pro Phe Leu Ala Ser Thr Gly Gly Val Arg Leu Met Leu
305                 310                 315                 320

His Glu Gln Arg Ser Tyr Pro Phe Ile Arg Asp Glu Gly Ile Tyr Ala
```

```
                    325                 330                 335
Met Ser Gly Thr Glu Thr Ser Ile Gly Val Leu Val Asp Lys Leu Gln
            340                 345                 350

Arg Met Gly Glu Pro Tyr Ser Pro Cys Thr Val Asn Gly Ser Glu Val
            355                 360                 365

Pro Val Gln Asn Phe Tyr Ser Asp Tyr Asn Thr Thr Tyr Ser Ile Gln
370                 375                 380

Ala Cys Leu Arg Ser Cys Phe Gln Asp His Met Ile Arg Asn Cys Asn
385                 390                 395                 400

Cys Gly His Tyr Leu Tyr Pro Leu Pro Arg Gly Glu Lys Tyr Cys Asn
                405                 410                 415

Asn Arg Asp Phe Pro Asp Trp Ala His Cys Tyr Ser Asp Leu Gln Met
            420                 425                 430

Ser Val Ala Gln Arg Glu Thr Cys Ile Gly Met Cys Lys Glu Ser Cys
            435                 440                 445

Asn Asp Thr Gln Tyr Lys Met Thr Ile Ser Met Ala Asp Trp Pro Ser
450                 455                 460

Glu Ala Ser Glu Asp Trp Ile Phe His Val Leu Ser Gln Glu Arg Asp
465                 470                 475                 480

Gln Ser Thr Asn Ile Thr Leu Ser Arg Lys Gly Ile Val Lys Leu Asn
                485                 490                 495

Ile Tyr Phe Gln Glu Phe Asn Tyr Arg Thr Ile Glu Glu Ser Ala Ala
            500                 505                 510

Asn Asn Ile Val Trp Leu Leu Ser Asn Leu Gly Gly Gln Phe Gly Phe
            515                 520                 525

Trp Met Gly Gly Ser Val Leu Cys Leu Ile Glu Phe Gly Glu Ile Ile
            530                 535                 540

Ile Asp Phe Val Trp Ile Thr Ile Lys Leu Val Ala Leu Ala Lys
545                 550                 555                 560

Ser Leu Arg Gln Arg Arg Ala Gln Ala Ser Tyr Ala Gly Pro Pro Pro
                565                 570                 575

Thr Val Ala Glu Leu Val Glu Ala His Thr Asn Phe Gly Phe Gln Pro
            580                 585                 590

Asp Thr Ala Pro Arg Ser Pro Asn Thr Gly Pro Tyr Pro Ser Glu Gln
            595                 600                 605

Ala Leu Pro Ile Pro Gly Thr Pro Pro Asn Tyr Asp Ser Leu Arg
            610                 615                 620

Leu Gln Pro Leu Asp Val Ile Glu Ser Asp Ser Glu Gly Asp Ala Ile
625                 630                 635                 640

<210> SEQ ID NO 9
<211> LENGTH: 649
<212> TYPE: PRT
<213> ORGANISM: Homo sapiens

<400> SEQUENCE: 9

Met Ala Pro Gly Glu Lys Ile Lys Ala Lys Ile Lys Lys Asn Leu Pro
1               5                   10                  15

Val Thr Gly Pro Gln Ala Pro Thr Ile Lys Glu Leu Met Arg Trp Tyr
            20                  25                  30

Cys Leu Asn Thr Asn Thr His Gly Cys Arg Arg Ile Val Val Ser Arg
        35                  40                  45

Gly Arg Leu Arg Arg Leu Leu Trp Ile Gly Phe Thr Leu Thr Ala Val
    50                  55                  60
```

```
Ala Leu Ile Leu Trp Gln Cys Ala Leu Leu Val Phe Ser Phe Tyr Thr
 65                  70                  75                  80

Val Ser Val Ser Ile Lys Val His Phe Arg Lys Leu Asp Phe Pro Ala
                 85                  90                  95

Val Thr Ile Cys Asn Ile Asn Pro Tyr Lys Tyr Ser Thr Val Arg His
            100                 105                 110

Leu Leu Ala Asp Leu Glu Gln Glu Thr Arg Glu Ala Leu Lys Ser Leu
        115                 120                 125

Tyr Gly Phe Pro Glu Ser Arg Lys Arg Arg Glu Ala Glu Ser Trp Asn
    130                 135                 140

Ser Val Ser Glu Gly Lys Gln Pro Arg Phe Ser His Arg Ile Pro Leu
145                 150                 155                 160

Leu Ile Phe Asp Gln Asp Glu Lys Gly Lys Ala Arg Asp Phe Phe Thr
                165                 170                 175

Gly Arg Lys Arg Lys Val Gly Gly Ser Ile Ile His Lys Ala Ser Asn
            180                 185                 190

Val Met His Ile Glu Ser Lys Gln Val Val Gly Phe Gln Leu Cys Ser
        195                 200                 205

Asn Asp Thr Ser Asp Cys Ala Thr Tyr Thr Phe Ser Ser Gly Ile Asn
    210                 215                 220

Ala Ile Gln Glu Trp Tyr Lys Leu His Tyr Met Asn Ile Met Ala Gln
225                 230                 235                 240

Val Pro Leu Glu Lys Lys Ile Asn Met Ser Tyr Ser Ala Glu Glu Leu
                245                 250                 255

Leu Val Thr Cys Phe Phe Asp Gly Val Ser Cys Asp Ala Arg Asn Phe
                260                 265                 270

Thr Leu Phe His His Pro Met His Gly Asn Cys Tyr Thr Phe Asn Asn
                275                 280                 285

Arg Glu Asn Glu Thr Ile Leu Ser Thr Ser Met Gly Gly Ser Glu Tyr
    290                 295                 300

Gly Leu Gln Val Ile Leu Tyr Ile Asn Glu Glu Glu Tyr Asn Pro Phe
305                 310                 315                 320

Leu Val Ser Ser Thr Gly Ala Lys Val Ile Ile His Arg Gln Asp Glu
                325                 330                 335

Tyr Pro Phe Val Glu Asp Val Gly Thr Glu Ile Glu Thr Ala Met Val
            340                 345                 350

Thr Ser Ile Gly Met His Leu Thr Glu Ser Phe Lys Leu Ser Glu Pro
        355                 360                 365

Tyr Ser Gln Cys Thr Glu Asp Gly Ser Asp Val Pro Ile Arg Asn Ile
    370                 375                 380

Tyr Asn Ala Ala Tyr Ser Leu Gln Ile Cys Leu His Ser Cys Phe Gln
385                 390                 395                 400

Thr Lys Met Val Glu Lys Cys Gly Cys Ala Gln Tyr Ser Gln Pro Leu
                405                 410                 415

Pro Pro Ala Ala Asn Tyr Cys Asn Tyr Gln Gln His Pro Asn Trp Met
            420                 425                 430

Tyr Cys Tyr Tyr Gln Leu His Arg Ala Phe Val Gln Glu Glu Leu Gly
        435                 440                 445

Cys Gln Ser Val Cys Lys Glu Ala Cys Ser Phe Lys Glu Trp Thr Leu
    450                 455                 460

Thr Thr Ser Leu Ala Gln Trp Pro Ser Val Val Ser Glu Lys Trp Leu
465                 470                 475                 480

Leu Pro Val Leu Thr Trp Asp Gln Gly Arg Gln Val Asn Lys Lys Leu
```

```
                    485                 490                 495
Asn Lys Thr Asp Leu Ala Lys Leu Leu Ile Phe Tyr Lys Asp Leu Asn
                500                 505                 510

Gln Arg Ser Ile Met Glu Ser Pro Ala Asn Ser Ile Glu Met Leu Leu
            515                 520                 525

Ser Asn Phe Gly Gly Gln Leu Gly Leu Trp Met Ser Cys Ser Val Val
        530                 535                 540

Cys Val Ile Glu Ile Ile Glu Val Phe Phe Ile Asp Phe Phe Ser Ile
545                 550                 555                 560

Ile Ala Arg Arg Gln Trp Gln Lys Ala Lys Glu Trp Trp Ala Trp Lys
                565                 570                 575

Gln Ala Pro Pro Cys Pro Glu Ala Pro Arg Ser Pro Gln Gly Gln Asp
                580                 585                 590

Asn Pro Ala Leu Asp Ile Asp Asp Leu Pro Thr Phe Asn Ser Ala
            595                 600                 605

Leu His Leu Pro Pro Ala Leu Gly Thr Gln Val Pro Gly Thr Pro Pro
        610                 615                 620

Pro Lys Tyr Asn Thr Leu Arg Leu Glu Arg Ala Phe Ser Asn Gln Leu
625                 630                 635                 640

Thr Asp Thr Gln Met Leu Asp Glu Leu
                645

<210> SEQ ID NO 10
<211> LENGTH: 699
<212> TYPE: PRT
<213> ORGANISM: Rattus sp.

<400> SEQUENCE: 10

Met Met Leu Asp His Thr Arg Ala Pro Glu Leu Asn Ile Asp Leu Asp
1               5                   10                  15

Leu His Ala Ser Asn Ser Pro Lys Gly Ser Met Lys Gly Asn Gln Phe
            20                  25                  30

Lys Glu Gln Asp Pro Cys Pro Pro Gln Pro Met Gln Gly Leu Gly Lys
        35                  40                  45

Gly Asp Lys Arg Glu Glu Gln Gly Leu Gly Pro Glu Pro Ser Ala Pro
    50                  55                  60

Arg Gln Pro Thr Glu Glu Glu Ala Leu Ile Glu Phe His Arg Ser
65                  70                  75                  80

Tyr Arg Glu Leu Phe Gln Phe Cys Asn Asn Thr Thr Ile His Gly
                85                  90                  95

Ala Ile Arg Leu Val Cys Ser Lys His Asn Arg Met Lys Thr Ala Phe
            100                 105                 110

Trp Ala Val Leu Trp Leu Cys Thr Phe Gly Met Met Tyr Trp Gln Phe
        115                 120                 125

Ala Leu Leu Phe Glu Glu Tyr Leu Ser Tyr Pro Val Ser Leu Asn Ile
    130                 135                 140

Asn Leu Asn Ser Asp Lys Leu Val Phe Pro Ala Val Thr Val Cys Thr
145                 150                 155                 160

Leu Asn Pro Tyr Arg Tyr Thr Glu Ile Lys Glu Glu Leu Glu Leu
                165                 170                 175

Asp Arg Ile Thr Glu Gln Thr Leu Phe Asp Leu Tyr Lys Tyr Asn Ser
            180                 185                 190

Ser Tyr Thr Arg Gln Ala Gly Ala Arg Arg Arg Ser Arg Asp Leu
        195                 200                 205
```

```
Leu Gly Ala Phe Pro His Pro Leu Gln Arg Leu Arg Thr Pro Pro
    210                 215                 220

Pro Tyr Ser Gly Arg Thr Ala Arg Ser Gly Ser Ser Val Arg Asp
225                 230                 235                 240

Asn Asn Pro Gln Val Asp Arg Lys Asp Trp Lys Ile Gly Phe Gln Leu
                245                 250                 255

Cys Asn Gln Asn Lys Ser Asp Cys Phe Tyr Gln Thr Tyr Ser Ser Gly
                260                 265                 270

Val Asp Ala Val Arg Glu Trp Tyr Arg Phe His Tyr Ile Asn Ile Leu
                275                 280                 285

Ser Arg Leu Ser Asp Thr Ser Pro Ala Leu Glu Glu Glu Ala Leu Gly
    290                 295                 300

Asn Phe Ile Phe Thr Cys Arg Phe Asn Gln Ala Pro Cys Asn Gln Ala
305                 310                 315                 320

Asn Tyr Ser Lys Phe His His Pro Met Tyr Gly Asn Cys Tyr Thr Phe
                325                 330                 335

Asn Asp Lys Asn Asn Ser Asn Leu Trp Met Ser Ser Met Pro Gly Val
                340                 345                 350

Asn Asn Gly Leu Ser Leu Thr Leu Arg Thr Glu Gln Asn Asp Phe Ile
            355                 360                 365

Pro Leu Leu Ser Thr Val Thr Gly Ala Arg Val Met Val His Gly Gln
    370                 375                 380

Asp Glu Pro Ala Phe Met Asp Asp Gly Gly Phe Asn Leu Arg Pro Gly
385                 390                 395                 400

Val Glu Thr Ser Ile Ser Met Arg Lys Glu Ala Leu Asp Ser Leu Gly
                405                 410                 415

Gly Asn Tyr Gly Asp Cys Thr Glu Asn Gly Ser Asp Val Pro Val Lys
                420                 425                 430

Asn Leu Tyr Pro Ser Lys Tyr Thr Gln Gln Val Cys Ile His Ser Cys
            435                 440                 445

Phe Gln Glu Asn Met Ile Lys Lys Cys Gly Cys Ala Tyr Ile Phe Tyr
    450                 455                 460

Pro Lys Pro Lys Gly Val Glu Phe Cys Asp Tyr Arg Lys Gln Ser Ser
465                 470                 475                 480

Trp Gly Tyr Cys Tyr Tyr Lys Leu Gln Gly Ala Phe Ser Leu Asp Ser
                485                 490                 495

Leu Gly Cys Phe Ser Lys Cys Arg Lys Pro Cys Ser Val Ile Asn Tyr
                500                 505                 510

Lys Leu Ser Ala Gly Tyr Ser Arg Trp Pro Ser Val Lys Ser Gln Asp
            515                 520                 525

Trp Ile Phe Glu Met Leu Ser Leu Gln Asn Asn Tyr Thr Ile Asn Asn
    530                 535                 540

Lys Arg Asn Gly Val Ala Lys Leu Asn Ile Phe Phe Lys Glu Leu Asn
545                 550                 555                 560

Tyr Lys Thr Asn Ser Glu Ser Pro Ser Val Thr Met Val Ser Leu Leu
                565                 570                 575

Ser Asn Leu Gly Ser Gln Trp Ser Leu Trp Phe Gly Ser Ser Val Leu
            580                 585                 590

Ser Val Val Glu Met Ala Glu Leu Ile Phe Asp Leu Leu Val Ile Thr
    595                 600                 605

Leu Leu Met Leu Leu Arg Arg Phe Arg Ser Arg Tyr Trp Ser Pro Gly
    610                 615                 620

Arg Gly Ala Arg Gly Ala Arg Glu Val Ala Ser Thr Pro Ala Ser Ser
```

```
                    625                 630                 635                 640

Phe Pro Ser Arg Phe Cys Pro His Pro Thr Ser Pro Pro Ser Leu
                    645                 650                 655

Pro Gln Gln Gly Met Thr Pro Leu Ala Leu Thr Ala Pro Pro Pro
                    660                 665                 670

Ala Tyr Ala Thr Leu Gly Pro Ser Ala Pro Pro Leu Asp Ser Ala Ala
                    675                 680                 685

Pro Asp Cys Ser Ala Cys Ala Leu Ala Ala Leu
                    690                 695

<210> SEQ ID NO 11
<211> LENGTH: 638
<212> TYPE: PRT
<213> ORGANISM: Rattus sp.

<400> SEQUENCE: 11

Met Pro Val Lys Lys Tyr Leu Leu Lys Cys Leu His Arg Leu Gln Lys
 1                  5                  10                  15

Gly Pro Gly Tyr Thr Tyr Lys Glu Leu Leu Val Trp Tyr Cys Asn Asn
                    20                  25                  30

Thr Asn Thr His Gly Pro Lys Arg Ile Ile Cys Glu Gly Pro Lys Lys
                    35                  40                  45

Lys Ala Met Trp Phe Leu Leu Thr Leu Leu Phe Ala Cys Leu Val Cys
                    50                  55                  60

Trp Gln Trp Gly Val Phe Ile Gln Thr Tyr Leu Ser Trp Glu Val Ser
 65                 70                  75                  80

Val Ser Leu Ser Met Gly Phe Lys Thr Met Asn Phe Pro Ala Val Thr
                    85                  90                  95

Val Cys Asn Ser Ser Pro Phe Gln Tyr Ser Lys Val Lys His Leu Leu
                    100                 105                 110

Lys Asp Leu Tyr Lys Leu Met Glu Ala Val Leu Asp Lys Ile Leu Ala
                    115                 120                 125

Pro Lys Ser Ser His Thr Asn Thr Thr Ser Thr Leu Asn Phe Thr Ile
                    130                 135                 140

Trp Asn His Thr Pro Leu Val Leu Ile Asp Glu Arg Asn Pro Asp His
145                 150                 155                 160

Pro Val Val Leu Asn Leu Phe Gly Asp Ser His Asn Ser Ser Asn Pro
                    165                 170                 175

Ala Pro Gly Ser Thr Cys Asn Ala Gln Gly Cys Lys Val Ala Met Arg
                    180                 185                 190

Leu Cys Ser Ala Asn Gly Thr Val Cys Thr Phe Arg Asn Phe Thr Ser
                    195                 200                 205

Ala Thr Gln Ala Val Thr Glu Trp Tyr Ile Leu Gln Ala Thr Asn Ile
                    210                 215                 220

Phe Ser Gln Val Leu Pro Gln Asp Leu Val Gly Met Gly Tyr Ala Pro
225                 230                 235                 240

Asp Arg Ile Ile Leu Ala Cys Leu Phe Gly Thr Glu Pro Cys Ser His
                    245                 250                 255

Arg Asn Phe Thr Pro Ile Phe Tyr Pro Asp Tyr Gly Asn Cys Tyr Ile
                    260                 265                 270

Phe Asn Trp Gly Met Thr Glu Lys Ala Leu Pro Ser Ala Asn Pro Gly
                    275                 280                 285

Thr Glu Phe Gly Leu Lys Leu Ile Leu Asp Ile Gly Gln Glu Asp Tyr
                    290                 295                 300
```

```
Val Pro Phe Leu Ala Ser Thr Ala Gly Ala Arg Leu Met Leu His Glu
305                 310                 315                 320

Gln Arg Thr Tyr Pro Phe Ile Arg Glu Glu Gly Ile Tyr Ala Met Ala
            325                 330                 335

Gly Thr Glu Thr Ser Ile Gly Val Leu Leu Asp Lys Leu Gln Gly Lys
        340                 345                 350

Gly Glu Pro Tyr Ser Pro Cys Thr Met Asn Gly Ser Asp Val Ala Ile
    355                 360                 365

Gln Asn Leu Tyr Ser Asp Tyr Asn Thr Thr Tyr Ser Ile Gln Ala Cys
370                 375                 380

Leu His Ser Cys Phe Gln Asp His Met Ile His Asn Cys Ser Cys Gly
385                 390                 395                 400

His Tyr Leu Tyr Pro Leu Pro Ala Gly Glu Lys Tyr Cys Asn Asn Arg
            405                 410                 415

Asp Phe Pro Asp Trp Ala Tyr Cys Tyr Leu Ser Leu Gln Met Ser Val
            420                 425                 430

Val Gln Arg Glu Thr Cys Leu Ser Met Cys Lys Glu Ser Cys Asn Asp
        435                 440                 445

Thr Gln Tyr Lys Met Thr Ile Ser Met Ala Asp Trp Pro Ser Glu Ala
450                 455                 460

Ser Glu Asp Trp Ile Leu His Val Leu Ser Gln Glu Arg Asp Gln Ser
465                 470                 475                 480

Ser Asn Ile Thr Leu Ser Arg Lys Gly Ile Val Lys Leu Asn Ile Tyr
            485                 490                 495

Phe Gln Glu Phe Asn Tyr Arg Thr Ile Glu Glu Ser Pro Ala Asn Asn
            500                 505                 510

Ile Val Trp Leu Leu Ser Asn Leu Gly Gly Gln Phe Gly Phe Trp Met
            515                 520                 525

Gly Gly Ser Val Leu Cys Leu Ile Glu Phe Gly Glu Ile Ile Ile Asp
        530                 535                 540

Phe Ile Trp Ile Thr Val Ile Lys Leu Val Ala Ser Cys Lys Gly Leu
545                 550                 555                 560

Arg Arg Arg Arg Pro Gln Arg Pro Tyr Thr Gly Pro Pro Thr Val
            565                 570                 575

Ala Glu Leu Val Glu Ala His Thr Asn Cys Val Phe Gln Pro Asp Thr
            580                 585                 590

Thr Ser Cys Arg Pro Asn Ala Glu Val Tyr Pro Asp Gln Gln Thr Leu
        595                 600                 605

Pro Ile Pro Gly Thr Pro Pro Asn Tyr Asp Ser Leu Arg Leu Gln
610                 615                 620

Pro Leu Asp Thr Met Glu Ser Asp Ser Glu Val Glu Ala Ile
625                 630                 635

<210> SEQ ID NO 12
<211> LENGTH: 650
<212> TYPE: PRT
<213> ORGANISM: Rattus sp.

<400> SEQUENCE: 12

Met Ala Pro Gly Glu Lys Ile Lys Ala Lys Ile Lys Lys Asn Leu Pro
1               5                   10                  15

Val Arg Gly Pro Gln Ala Pro Thr Ile Lys Asp Leu Met His Trp Tyr
            20                  25                  30

Cys Met Asn Thr Asn Thr His Gly Cys Arg Arg Ile Val Val Ser Arg
        35                  40                  45
```

-continued

```
Gly Arg Leu Arg Pro Leu Leu Trp Ile Ala Phe Thr Leu Thr Ala Val
 50                  55                  60

Ala Leu Ile Ile Trp Gln Cys Ala Leu Leu Val Phe Ser Phe Tyr Thr
 65                  70                  75                  80

Val Ser Val Ser Ile Lys Val His Phe Gln Lys Leu Asp Phe Pro Ala
                 85                  90                  95

Val Thr Ile Cys Asn Ile Asn Pro Tyr Lys Tyr Ser Ala Val Ser Asp
            100                 105                 110

Leu Leu Thr Asp Leu Asp Ser Glu Thr Lys Gln Ala Leu Leu Ser Leu
        115                 120                 125

Tyr Gly Val Lys Glu Ser Arg Lys Arg Glu Ala Gly Ser Met Pro
130                 135                 140

Ser Thr Leu Glu Gly Thr Pro Pro Arg Phe Phe Lys Leu Ile Pro Leu
145                 150                 155                 160

Leu Val Phe Asn Glu Asn Glu Lys Gly Lys Ala Arg Asp Phe Phe Thr
                165                 170                 175

Gly Arg Lys Arg Lys Ile Ser Gly Lys Ile Ile His Lys Ala Ser Asn
            180                 185                 190

Val Met His Val His Glu Ser Lys Lys Leu Val Gly Phe Gln Leu Cys
        195                 200                 205

Ser Asn Asp Thr Ser Asp Cys Ala Thr Tyr Thr Phe Ser Ser Gly Ile
210                 215                 220

Asn Ala Ile Gln Glu Trp Tyr Lys Leu His Tyr Met Asn Ile Met Ala
225                 230                 235                 240

Gln Val Pro Leu Glu Lys Lys Ile Asn Met Ser Tyr Ser Ala Glu Glu
                245                 250                 255

Leu Leu Val Thr Cys Phe Phe Asp Gly Met Ser Cys Asp Ala Arg Asn
            260                 265                 270

Phe Thr Leu Phe His His Pro Met Tyr Gly Asn Cys Tyr Thr Phe Asn
        275                 280                 285

Asn Lys Glu Asn Ala Thr Ile Leu Ser Thr Ser Met Gly Gly Ser Glu
290                 295                 300

Tyr Gly Leu Gln Val Ile Leu Tyr Ile Asn Glu Asp Glu Tyr Asn Pro
305                 310                 315                 320

Phe Leu Val Ser Ser Thr Gly Ala Lys Val Leu Ile His Gln Gln Asn
                325                 330                 335

Glu Tyr Pro Phe Ile Glu Asp Val Gly Met Glu Ile Glu Thr Ala Met
            340                 345                 350

Ser Thr Ser Ile Gly Met His Leu Thr Glu Ser Phe Lys Leu Ser Glu
        355                 360                 365

Pro Tyr Ser Gln Cys Thr Glu Asp Gly Ser Asp Val Pro Val Thr Asn
370                 375                 380

Ile Tyr Asn Ala Ala Tyr Ser Leu Gln Ile Cys Leu Tyr Ser Cys Phe
385                 390                 395                 400

Gln Thr Lys Met Val Glu Lys Cys Gly Cys Ala Gln Tyr Ser Gln Pro
                405                 410                 415

Leu Pro Pro Ala Ala Asn Tyr Cys Asn Tyr Gln Gln His Pro Asn Trp
            420                 425                 430

Met Tyr Cys Tyr Tyr Gln Leu Tyr Gln Ala Phe Val Arg Glu Glu Leu
        435                 440                 445

Gly Cys Gln Ser Val Cys Lys Gln Ser Cys Ser Phe Lys Glu Trp Thr
450                 455                 460
```

```
Leu Thr Thr Ser Leu Ala Gln Trp Pro Ser Glu Ala Ser Glu Lys Trp
465                 470                 475                 480

Leu Leu Asn Val Leu Thr Trp Asp Gln Ser Gln Gln Ile Asn Lys Lys
                485                 490                 495

Leu Asn Lys Thr Asp Leu Ala Lys Leu Leu Ile Phe Tyr Lys Asp Leu
            500                 505                 510

Asn Gln Arg Ser Ile Met Glu Ser Pro Ala Asn Ser Ile Glu Met Leu
        515                 520                 525

Leu Ser Asn Phe Gly Gly Leu Gly Leu Trp Met Ser Cys Ser Val
    530                 535                 540

Val Cys Val Ile Glu Ile Ile Glu Val Phe Phe Ile Asp Phe Phe Ser
545                 550                 555                 560

Ile Ile Ala Arg Arg Gln Trp His Lys Ala Lys Asp Cys Trp Ala Arg
                565                 570                 575

Arg Gln Thr Pro Pro Ser Thr Glu Thr Pro Ser Ser Arg Gln Gly Gln
            580                 585                 590

Asp Asn Pro Ala Leu Asp Thr Asp Asp Leu Pro Thr Phe Thr Ser
        595                 600                 605

Ala Met Arg Leu Pro Pro Ala Pro Gly Ser Thr Val Pro Gly Thr Pro
610                 615                 620

Pro Pro Arg Tyr Asn Thr Leu Arg Leu Asp Arg Ala Phe Ser Ser Gln
625                 630                 635                 640

Leu Thr Asp Thr Gln Leu Thr Asn Glu Leu
                645                 650
```

<210> SEQ ID NO 13
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
gttcttaagg cacaggaact gggac                                          25

<210> SEQ ID NO 14
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
gaagttaacc ctgtcgttct gcgac                                          25

<210> SEQ ID NO 15
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 15
gttctatagg gtctgcttgt cgctc                                          25

<210> SEQ ID NO 16

```
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 16
gccagtccca gttcctgtgc cttaagaacc tcgc                               34

<210> SEQ ID NO 17
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 17
gcgagtcgca gaacgacagg gttaacttcc tcgc                               34

<210> SEQ ID NO 18
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 18
gcgagagcga caagcagacc ctatagaacc tcgc                               34

<210> SEQ ID NO 19
<211> LENGTH: 728
<212> TYPE: PRT
<213> ORGANISM: Homo sapiens

<400> SEQUENCE: 19
```

Met Gly Met Ala Arg Gly Ser Leu Thr Arg Val Pro Gly Val Met Gly
1               5                   10                  15

Glu Gly Thr Gln Gly Pro Glu Leu Ser Leu Asp Pro Asp Pro Cys Ser
                20                  25                  30

Pro Gln Ser Thr Pro Gly Leu Met Lys Gly Asn Lys Leu Glu Glu Gln
            35                  40                  45

Asp Pro Arg Pro Leu Gln Pro Ile Pro Gly Leu Met Glu Gly Asn Lys
        50                  55                  60

Leu Glu Glu Gln Asp Ser Ser Pro Pro Gln Ser Thr Pro Gly Leu Met
65                  70                  75                  80

Lys Gly Asn Lys Arg Glu Glu Gln Gly Leu Gly Pro Glu Pro Ala Ala
                85                  90                  95

Pro Gln Gln Pro Thr Ala Glu Glu Ala Leu Ile Glu Phe His Arg
            100                 105                 110

Ser Tyr Arg Glu Leu Phe Glu Phe Phe Cys Asn Asn Thr Thr Ile His
        115                 120                 125

Gly Ala Ile Arg Leu Val Cys Ser Gln His Asn Arg Met Lys Thr Ala
    130                 135                 140

Phe Trp Ala Val Leu Trp Leu Cys Thr Phe Gly Met Met Tyr Trp Gln
145                 150                 155                 160

Phe Gly Leu Leu Phe Gly Glu Tyr Phe Ser Tyr Pro Val Ser Leu Asn

```
            165                 170                 175
Ile Asn Leu Asn Ser Asp Lys Leu Val Phe Pro Ala Val Thr Ile Cys
            180                 185                 190

Thr Leu Asn Pro Tyr Arg Tyr Pro Glu Ile Lys Glu Glu Leu Glu Glu
            195                 200                 205

Leu Asp Arg Ile Thr Glu Gln Thr Leu Phe Asp Leu Tyr Lys Tyr Ser
210                 215                 220

Ser Phe Thr Thr Leu Val Ala Gly Ser Arg Ser Arg Arg Asp Leu Arg
225                 230                 235                 240

Gly Thr Leu Pro His Pro Leu Gln Arg Leu Arg Val Pro Pro Pro Pro
                245                 250                 255

His Gly Ala Arg Arg Ala Arg Ser Val Ala Ser Ser Leu Arg Asp Asn
                260                 265                 270

Asn Pro Gln Val Asp Trp Lys Asp Trp Lys Ile Gly Phe Gln Leu Cys
                275                 280                 285

Asn Gln Asn Lys Ser Asp Cys Phe Tyr Gln Thr Tyr Ser Ser Gly Val
                290                 295                 300

Asp Ala Val Arg Glu Trp Tyr Arg Phe His Tyr Ile Asn Ile Leu Ser
305                 310                 315                 320

Arg Leu Pro Glu Thr Leu Pro Ser Leu Glu Glu Asp Thr Leu Gly Asn
                325                 330                 335

Phe Ile Phe Ala Cys Arg Phe Asn Gln Val Ser Cys Asn Gln Ala Asn
                340                 345                 350

Tyr Ser His Phe His His Pro Met Tyr Gly Asn Cys Tyr Thr Phe Asn
                355                 360                 365

Asp Lys Asn Asn Ser Asn Leu Trp Met Ser Ser Met Pro Gly Ile Asn
            370                 375                 380

Asn Gly Leu Ser Leu Met Leu Arg Ala Glu Gln Asn Asp Phe Ile Pro
385                 390                 395                 400

Leu Leu Ser Thr Val Thr Gly Ala Arg Val Met Val His Gly Gln Asp
                405                 410                 415

Glu Pro Ala Phe Met Asp Asp Gly Gly Phe Asn Leu Arg Pro Gly Val
                420                 425                 430

Glu Thr Ser Ile Ser Met Arg Lys Glu Thr Leu Asp Arg Leu Gly Gly
                435                 440                 445

Asp Tyr Gly Asp Cys Thr Lys Asn Gly Ser Asp Val Pro Val Glu Asn
            450                 455                 460

Leu Tyr Pro Ser Lys Tyr Thr Gln Gln Val Cys Ile His Ser Cys Phe
465                 470                 475                 480

Gln Glu Ser Met Ile Lys Glu Cys Gly Cys Ala Tyr Ile Phe Tyr Pro
                485                 490                 495

Arg Pro Gln Asn Val Glu Tyr Cys Asp Tyr Arg Lys His Ser Ser Trp
                500                 505                 510

Gly Tyr Cys Tyr Tyr Lys Leu Gln Val Asp Phe Ser Ser Asp His Leu
            515                 520                 525

Gly Cys Phe Thr Lys Cys Arg Lys Pro Cys Ser Val Thr Ser Tyr Gln
            530                 535                 540

Leu Ser Ala Gly Tyr Ser Arg Trp Pro Ser Val Thr Ser Gln Glu Trp
545                 550                 555                 560

Val Phe Gln Met Leu Ser Arg Gln Asn Asn Tyr Thr Val Asn Asn Lys
                565                 570                 575

Arg Asn Gly Val Ala Lys Val Asn Ile Phe Phe Lys Glu Leu Asn Tyr
            580                 585                 590
```

```
Lys Thr Asn Ser Glu Ser Pro Ser Val Thr Met Val Thr Leu Leu Ser
            595                 600                 605

Asn Leu Gly Ser Gln Trp Ser Leu Trp Phe Gly Ser Ser Val Leu Ser
        610                 615                 620

Val Val Glu Met Ala Glu Leu Val Phe Asp Leu Leu Val Ile Met Phe
625                 630                 635                 640

Leu Met Leu Leu Arg Arg Phe Arg Ser Arg Tyr Trp Ser Pro Gly Arg
            645                 650                 655

Gly Gly Arg Gly Ala Gln Glu Val Ala Ser Thr Leu Ala Ser Ser Pro
        660                 665                 670

Pro Ser His Phe Cys Pro His Pro Met Ser Leu Ser Leu Ser Gln Pro
            675                 680                 685

Gly Pro Ala Pro Ser Pro Ala Leu Thr Ala Pro Pro Ala Tyr Ala
        690                 695                 700

Thr Leu Gly Pro Arg Pro Ser Pro Gly Gly Ser Ala Gly Ala Ser Ser
705                 710                 715                 720

Ser Thr Cys Pro Leu Gly Gly Pro
            725
```

<210> SEQ ID NO 20
<211> LENGTH: 244
<212> TYPE: PRT
<213> ORGANISM: Homo sapiens

<400> SEQUENCE: 20

```
Met Glu Gly Asn Lys Leu Glu Glu Gln Asp Ser Ser Pro Pro Gln Ser
1               5                   10                  15

Thr Pro Gly Leu Met Lys Gly Asn Lys Arg Glu Glu Gln Gly Leu Gly
            20                  25                  30

Pro Glu Pro Ala Ala Pro Gln Gln Pro Thr Ala Glu Glu Ala Leu
        35                  40                  45

Ile Glu Phe His Arg Ser Tyr Arg Glu Leu Phe Glu Phe Phe Cys Asn
        50                  55                  60

Asn Thr Thr Ile His Gly Ala Ile Arg Leu Val Cys Ser Gln His Asn
65                  70                  75                  80

Arg Met Lys Thr Ala Phe Trp Ala Val Leu Trp Leu Cys Thr Phe Gly
            85                  90                  95

Met Met Tyr Trp Gln Phe Gly Leu Leu Phe Gly Glu Tyr Phe Ser Tyr
            100                 105                 110

Pro Val Ser Leu Asn Ile Asn Leu Asn Ser Asp Lys Leu Val Phe Pro
        115                 120                 125

Ala Val Thr Ile Cys Thr Leu Asn Pro Tyr Arg Tyr Pro Glu Ile Lys
130                 135                 140

Glu Glu Leu Glu Glu Leu Asp Arg Ile Thr Glu Gln Thr Leu Phe Asp
145                 150                 155                 160

Leu Tyr Lys Tyr Ser Ser Phe Thr Thr Leu Val Ala Gly Ser Arg Ser
            165                 170                 175

Arg Arg Asp Leu Arg Gly Thr Leu Pro His Pro Leu Gln Arg Leu Arg
        180                 185                 190

Val Pro Pro Pro His Gly Ala Arg Arg Ala Arg Ser Val Ala Ser
        195                 200                 205

Ser Leu Arg Asp Asn Asn Pro Gln Val Asp Trp Lys Asp Trp Lys Ile
        210                 215                 220

Gly Phe Gln Leu Glu Leu Leu Ser Leu Pro Pro Pro Asp Val Trp Lys
```

```
                   225                 230                 235                 240

Leu Leu Tyr Phe

<210> SEQ ID NO 21
<211> LENGTH: 650
<212> TYPE: PRT
<213> ORGANISM: Homo sapiens

<400> SEQUENCE: 21

Met Glu Gly Asn Lys Leu Glu Glu Gln Asp Ser Ser Pro Pro Gln Ser
1               5                   10                  15

Thr Pro Gly Leu Met Lys Gly Asn Lys Arg Glu Glu Gln Gly Leu Gly
            20                  25                  30

Pro Glu Pro Ala Ala Pro Gln Gln Pro Thr Ala Glu Glu Ala Leu
        35                  40                  45

Ile Glu Phe His Arg Ser Tyr Arg Glu Leu Phe Glu Phe Phe Cys Asn
50                  55                  60

Asn Thr Thr Ile His Gly Ala Ile Arg Leu Val Cys Ser Gln His Asn
65                  70                  75                  80

Arg Met Lys Thr Ala Phe Trp Ala Val Leu Trp Leu Cys Thr Phe Gly
                85                  90                  95

Met Met Tyr Trp Gln Phe Gly Leu Leu Phe Gly Glu Tyr Phe Ser Tyr
            100                 105                 110

Pro Val Ser Leu Asn Ile Asn Leu Asn Ser Asp Lys Leu Val Phe Pro
        115                 120                 125

Ala Val Thr Ile Cys Thr Leu Asn Pro Tyr Arg Tyr Pro Glu Ile Lys
130                 135                 140

Glu Glu Leu Glu Glu Leu Asp Arg Ile Thr Glu Gln Thr Leu Phe Asp
145                 150                 155                 160

Leu Tyr Lys Tyr Ser Ser Phe Thr Thr Leu Val Ala Gly Ser Arg Ser
                165                 170                 175

Arg Arg Asp Leu Arg Gly Thr Leu Pro His Pro Leu Gln Arg Leu Arg
            180                 185                 190

Val Pro Pro Pro His Gly Ala Arg Arg Ala Arg Ser Val Ala Ser
        195                 200                 205

Ser Leu Arg Asp Asn Asn Pro Gln Val Asp Trp Lys Asp Trp Lys Ile
210                 215                 220

Gly Phe Gln Leu Cys Asn Gln Asn Lys Ser Asp Cys Phe Tyr Gln Thr
225                 230                 235                 240

Tyr Ser Ser Gly Val Asp Ala Val Arg Glu Trp Tyr Arg Phe His Tyr
                245                 250                 255

Ile Asn Ile Leu Ser Arg Leu Pro Glu Thr Leu Pro Ser Leu Glu Glu
            260                 265                 270

Asp Thr Leu Gly Asn Phe Ile Phe Ala Cys Arg Phe Asn Gln Val Ser
        275                 280                 285

Cys Asn Gln Ala Asn Tyr Ser His Phe His His Pro Met Tyr Gly Asn
290                 295                 300

Cys Tyr Thr Phe Asn Asp Lys Asn Asn Ser Asn Leu Trp Met Ser Ser
305                 310                 315                 320

Met Pro Gly Ile Asn Asn Val Thr Gly Ala Arg Val Met Val His Gly
                325                 330                 335

Gln Asp Glu Pro Ala Phe Met Asp Asp Gly Gly Phe Asn Leu Arg Pro
            340                 345                 350

Gly Val Glu Thr Ser Ile Ser Met Arg Lys Glu Thr Leu Asp Arg Leu
```

```
            355                 360                 365
Gly Gly Asp Tyr Gly Asp Cys Thr Lys Asn Gly Ser Asp Val Pro Val
        370                 375                 380
Glu Asn Leu Tyr Pro Ser Lys Tyr Thr Gln Gln Val Cys Ile His Ser
385                 390                 395                 400
Cys Phe Gln Glu Ser Met Ile Lys Glu Cys Gly Cys Ala Tyr Ile Phe
                405                 410                 415
Tyr Pro Arg Pro Gln Asn Val Glu Tyr Cys Asp Tyr Arg Lys His Ser
            420                 425                 430
Ser Trp Gly Tyr Cys Tyr Tyr Lys Leu Gln Val Asp Phe Ser Ser Asp
                435                 440                 445
His Leu Gly Cys Phe Thr Lys Cys Arg Lys Pro Cys Ser Val Thr Ser
        450                 455                 460
Tyr Gln Leu Ser Ala Gly Tyr Ser Arg Trp Pro Ser Val Thr Ser Gln
465                 470                 475                 480
Glu Trp Val Phe Gln Met Leu Ser Arg Gln Asn Asn Tyr Thr Val Asn
                485                 490                 495
Asn Lys Arg Asn Gly Val Ala Lys Val Asn Ile Phe Phe Lys Glu Leu
            500                 505                 510
Asn Tyr Lys Thr Asn Ser Glu Ser Pro Ser Val Thr Met Val Thr Leu
        515                 520                 525
Leu Ser Asn Leu Gly Ser Gln Trp Ser Leu Trp Phe Gly Ser Ser Val
530                 535                 540
Leu Ser Val Val Glu Met Ala Glu Leu Val Phe Asp Leu Leu Val Ile
                545                 550                 555                 560
Met Phe Leu Met Leu Leu Arg Arg Phe Arg Ser Arg Tyr Trp Ser Pro
                565                 570                 575
Gly Arg Gly Gly Arg Gly Ala Gln Glu Val Ala Ser Thr Leu Ala Ser
            580                 585                 590
Ser Pro Pro Ser His Phe Cys Pro His Pro Met Ser Leu Ser Leu Ser
        595                 600                 605
Gln Pro Gly Pro Ala Pro Ser Pro Ala Leu Thr Ala Pro Pro Ala
    610                 615                 620
Tyr Ala Thr Leu Gly Pro Arg Pro Ser Pro Gly Gly Ser Ala Gly Ala
625                 630                 635                 640
Ser Ser Ser Thr Cys Pro Leu Gly Gly Pro
                645                 650

<210> SEQ ID NO 22
<211> LENGTH: 2100
<212> TYPE: DNA
<213> ORGANISM: Mus sp.

<400> SEQUENCE: 22
atgctggacc acaccagagc ccctgagctc aaccttgacc tagaccttga cgtctccaac      60
tcaccgaagg gatccatgaa gggcaacaat ttcaaggagc aagacctttg tcctcctctg     120
cccatgcaag gactgggcaa gggggacaag cgtgaagaac aggcgctggg cccggaaccc     180
tcagagcccc ggcagcccac cgaggaggag gaggcactga tcgagttcca ccgctcctac     240
cgggagctct tccagttctt ctgcaacaat accaccatcc acggtgccat ccgcctggtg     300
tgctccaagc acaaccgcat gaagacggcc ttctgggcgg tgctgtggct ctgaccttc     360 ggcatgatgt actggcagtt tgctttgctg ttcgaggaat acttcagcta ccccgtgagt     420
ctcaacatca acctcaattc ggacaagctg gtcttccctg ccgtcactgt gtgcaccctt     480
```

```
aatccttaca gatacactga aattaaagag gatctggaag agctggaccg catcacggaa    540
cagacgcttt ttgacctgta caaatacaac tcttcctaca ctcgccaggc tgggggccgc    600
cgccgcagca cccgcgacct ccggggtgct ctcccacacc ccctgcagcg cctgcgcaca    660
ccacctccgc ccaatcccgc ccgctcggcg cgcagcgcgt cttccagtgt acgcgacaac    720
aatccccaag tggacaggaa ggactggaaa tcggcttcc  aactgtgcaa ccagaacaaa    780
tcagactgct tctaccagac atactcatcc ggggtggatg ccgtgagaga gtggtaccgc    840
ttccattaca tcaacattct gtccagactg cccgacacct cgcctgctct agaggaagaa    900
gccctgggca gcttcatctt tacctgtcgt ttcaaccagg ccccctgcaa tcaggcgaat    960
tattctcagt tccaccaccc catgtatggg aactgctaca cttttcaacaa caagaacaac   1020 tccaatctct ggatgtcttc catgcctgga gtcaacaatg gtttgtccct gacactgcgc   1080
acagagcaga atgacttcat ccccctgctg tccacagtga cggggccag  ggtgatggtg   1140 cacggtcagg atgagcctgc ttttatggat gatggtggct tcaacgtgag gcctggtgtg   1200
gagacctcca tcagtatgag aaaggaagcc ctggacagcc tcggaggcaa ctacggagac   1260
tgcactgaga tggcagcga  tgtccctgtc aagaaccttt accccctccaa gtacacacag   1320 caggtgtgca ttcactcctg cttccaggag aacatgatca agaagtgtgg ctgtgcctac   1380
atcttctacc ctaagcccaa gggtgtagag ttctgtgact acctaaagca gagctcctgg   1440
ggctactgct actataaact gcaggctgcc ttctccttgg atagcctggg ctgcttctcc   1500
aagtgcagga agccgtgcag tgtgaccaac tacaagctct ctgctggcta ctcaagatgg   1560
ccgtctgtga agtcccagga ttggatcttc gagatgctat ccttgcagaa taattacacg   1620
atcaacaaca aaagaaacgg agttgctaaa ctcaacatct tcttcaaaga gctgaactat   1680
aaaactaatt cggagtctcc ctctgtcacg atggtcagcc tcctgtccaa cctgggcagc   1740
cagtggagcc tgtggttcgg ctcatctgtg ctgtccgtgg tggaaatggc ggagctcatc   1800
ttcgacctcc tggtcatcac actcatcatg ttactgcaca ggttccggag ccggtactgg   1860
tctccaggac gaggggccag gggtgccagg gaggtggcct ctaccccagc ttcctccttc   1920
ccttcccgtt tctgtcccca ccctacatcc ccgccacctt ctttgcccca gcagggcacg   1980 accctccc  tggccctgac agcccctcca cctgcctatg ctaccctagg cccctctgcc   2040
tctccactgg actcggctgt gcctggctct tctgcctgtg ctccggccat ggcactctga   2100
```

<210> SEQ ID NO 23
<211> LENGTH: 1917
<212> TYPE: DNA
<213> ORGANISM: Mus sp.

<400> SEQUENCE: 23

```
atgccagtga agaagtacct cctgaagtgc ctgcaccggc tgcagaaggg cccaggctac     60
acctacaagg agctgctagt gtggtactgc aataacacca acaccacgg  ccccaaacgc    120 atcatctgtg aggggcccaa gaagaaggcc atgtggttcc tgcttacgct gctcttcgcc    180
tgcctggtgt gctggcagtg gggagtcttc atccagacct acctgagctg ggaggtcagc    240
gtctcgctct ccatgggctt caagacgatg aacttcccgg cggtcaccgt ctgcaattcc    300
agccccttcc agtactccaa ggtcaagcac ttgctcaagg acttggatga gctaatggag    360
gcagtccctg gaaaagattc tggctccaga gccagccaca gcaacaccac caggaccctg    420
aactttacca tctggaacca cacaccctg gtccttattg atgagcggaa ccctgaccac    480
```

```
ccgtggttc tcaatttgtt tggggacagc cacaacagca gcaacccggc tccaggaagc    540
acctgcaatg cccagggatg caaagtggcc atgaggctgt gcagtgccaa tggaactgtg    600
tgtaccttgc ggaacttcac cagtgccacc caggccgtaa ctgagtggta catcctgcag    660
gccaccaaca tcttctcaca agtgcttcct caggacctgg tggggatggg ctatgcccct    720
gatcgcataa tcctagcttg cctgtttgga acagagccct gcagtcatcg gaacttcacg    780
cctatcttct accctgatta tggcaactgc tacatcttca actggggcat gacagaggag    840
acacttcctt ctgccaaccc tgggactgaa tttggtctca agttgatcct ggacatcggt    900
caggaggact atgtcccctt ccttgcgtcc acagcagggg ctaggctgat gcttcatgag    960
cagaggacgt acccctttcat tagagaggag ggcatctatg ccatggcagg aactgagacg   1020
tctattgggg tgctggtgga caagctgcaa cgcaaggggg agccctacag tccctgcacc   1080
atgaacggct ccgatgttgc cataaagaac ctctacagtg tctacaacac cacctattcc   1140
atccaggcct gtcttcattc ctgttttccaa gaccacatga tccgtaactg cagttgtggc   1200
cactacttat acccactgcc tgaaggagag aaatactgca caacaggga cttcccagac   1260 tgggcctatt gctatctaaa cctgcagatg agtgtgaccc agagagagac ctgcctcagc   1320
atgtgcaagg agtcctgcaa tgacacccag tataagatga ccatctccat ggctgactgg   1380
ccatctgagg cctctgagga ttggatctta catgtcctgt ctcaggagcg ggaccagagc   1440
tcgaatatca ccctgagcag gaagggtatt gtcaagctca atatctactt ccaagagttc   1500
aactaccgta ccattgagga atctccagcc aacaatattg tgtggctgct ctctaacctg   1560
gggggccagt ttggcttctg gagtgggggc tcggtgctgt gcctcattga gtttggggag   1620
atcattatcg acttcatttg gatcaccatc atcaagctgg tggcctcctg caaaggcctg   1680
cgcaggaggc ggccacaggc accctacact ggcccaccgc ccactgtggc tgagctggta   1740
gaggcccaca ccaactttgg cttccagcct gacacaacca gctgcaggcc ccacggcgag   1800
gtctaccctg accaacagac tctgcccatc ccggggactc cacccccaa ctatgactcc    1860 ctgaggctgc agccgctgga caccatggag tcggacagtg aggtggaggc catctag      1917
```

<210> SEQ ID NO 24
<211> LENGTH: 1968
<212> TYPE: DNA
<213> ORGANISM: Mus sp.

<400> SEQUENCE: 24

```
atggcgcctg agagaagat caaagccaaa atcaaaaaga atctgccagt tcgaggcccc     60
caggcaccga ccattaagga cctgatgcat tggtactgcc tgaacaccaa cacccacggc    120
tgccggcgca tcgtggtgtc ccgaggccgc cttcggcgcc tgttgtggat tgcgttcacg    180
ctgacagcag tggccctcat tatctggcag tgcgccctcc tcgtcttctc tttctacacc    240
gtctctgtct ccatcaaagt ccacttccag aaactggatt tccccgctgt cactatctgc    300
aatatcaacc cctacaagta cagtgctgtg agtgacctcc tgactgactt ggacagtgag    360
acaaaacagg ccttgctgtc cttgtatggg gtcaaagatg ttctagacag tacacctcgg    420
aaacgccggg aagcaggatc catgcggtcc acgtgggaag gcacaccacc cagatttctc    480
aacctgatcc cattgttggt cttcaatgag aacgagaagg gaaaggccag ggacttcttc    540
actggtcgga agcggaaaat cagtgggaaa atcatacaca aggcttctaa tgtcatgcac    600
gttcatgagt cgaagaaact ggtgggattt cagttgtgct caaatgacac ctctgactgt    660
gccacctaca ccttcagctc aggaatcaat gccatccagg agtggtacaa acttcactac    720
```

-continued

| | |
|---|---|
| atgaatatca tggcacaggt gcctctagag aagaaaatca acatgagcta ttctgccgaa | 780 |
| gaactgctgg tgacctgctt cttcgatggg atgtcctgtg atgccaggaa cttcactctt | 840 |
| ttccaccatc caatgtatgg gaactgctac acgttcaaca acagagaaaa cgccaccatc | 900 |
| ctcagcacct ccatgggagg cagtgagtat ggtctgcaag tcatcttata cataaacgaa | 960 |
| gatgagtaca ccccttcct ggtgtcatcc actggagcca aggtgcttgt ccatcagcag | 1020 |
| aatgaatacc ctttcatcga agacgtgggg accgagatcg agacagcaat gtccacttcc | 1080 |
| ataggaatgc acctgacaga atccttcaag ctgagcgaac cttacagcca gtgcacagag | 1140 |
| gacggcagcg atgtgcccgt cacaaacatc tacaatgctg cctattccct ccagatctgc | 1200 |
| ctttactcat gcttccaaac gaagatggtg gaaaaatgtg gctgtgccca gtacagtcag | 1260 |
| cctctacctc cagcagccaa ttactgcaac taccagcaac accccaactg gatgtattgc | 1320 |
| tactaccagc tgtaccaggc ctttgtccgg gaagaactgg gctgccaatc agtgtgcaag | 1380 |
| caatcctgca gctttaagga atggacactg accaccagct ggcacagtg gccatctgag | 1440 |
| gcttctgaga atggttgct gaatgttctc acctgggacc aaagccagca aataaacaaa | 1500 |
| aagctcaaca agactgacct ggccaagctc ttgatattct acaaagacct gaaccaaaga | 1560 |
| tccatcatgg agagcccagc caacagtatt gagatgctcc tgtctaactt tggtggacag | 1620 |
| ctcggcctgt ggatgagctg ctcggtcgtc tgtgtcatcg aaatcatcga agtcttcttc | 1680 |
| attgatttct tctctattat tgcccgccgc cagtggcaga aagccaagga ttggtgggcc | 1740 |
| cgtaggcgga caccacccctc cactgagact ccctccagcc agcagggtca ggataatcca | 1800 |
| gccctggata cggacgatga tctgcccact tttacctctg ctatgcgcct gcctccagcc | 1860 |
| ccggaggctc cggtgcctgg cacaccaccc cccagataca ataccttgcg cttggacagt | 1920 |
| gccttttcct cccagctcac agacactcag ttgaccaatg agttctaa | 1968 |

<210> SEQ ID NO 25
<211> LENGTH: 2325
<212> TYPE: DNA
<213> ORGANISM: Mus sp.

<400> SEQUENCE: 25

| | |
|---|---|
| gtgctgctcc tggatgtctc aggggtgctg tacgggcagc ttgtgcttct attaaagcag | 60 |
| tgttggggcc actcagtcat catggcagtg tccccacact ctgagtgcaa attcttccca | 120 |
| tctatcgttc catgtgatgt aaacccacat cagtgagggt ctgagagttg tcagccttgg | 180 |
| gtatgggttc cccaacacat atatcagcct ggaatatatc cccgggtgta gtctcagatg | 240 |
| agacctcgtg atcctatttc tcccaactcc tgtacctaat tgggacttct cagatctttg | 300 |
| tgtcattcct aaaggaactc ctggacactg ctaggacccc cagggttatt aggtaaaggg | 360 |
| gaactttata ggtcagtctg agctgggttg caattgtaag gcacctcagg aggaaagacc | 420 |
| aagtagaact ccaggtaagg agtgtatatt cgcctgccac gagggcatgt ggccctggaa | 480 |
| atggccaggc tggagacctg atctcaactc tgaaatcatg agtgtatagg cccagctccg | 540 |
| aatccaaagc tctcttgcct tgagagaggg ataggctgct tgttttcatt ggacacaagg | 600 |
| gacactgacg ccacatagtg ctggatcacc ctgctctgta ccccagggaa acccacagga | 660 |
| ctctccacag gaacactagc catgcctaca ggccagacct catttgccaa catctggaag | 720 |
| tacttgattc tcttgcctgg gaaaacatca atgctctcta caagttccac tttagtgaaa | 780 |
| gatgggacac ccccttgct gaagtcccca gccataaact ccactttcgg ctggaccacg | 840 |

```
ggattcatct gcagcatctg agtcgtctgg acagtcagta cgaagtgggc ttcagactga      900
tgagctctgg gcctcaagga ggtaagcatg ctatatgctg ctgcccctag gaaggctttt      960
ctggcaggga cagacgatgg tctgtgactg acctaaccct gcctcctctc tgtgtaatag     1020
agaggtggca actgtttcta ctgtgcctac tcctcaggta tgccacctgc tcaggaatta     1080
tattgcttct gttacatgga cattttggcc tcactgcctg ggaagacagt caccaaagtc     1140
atggtgacct tgtcctgtca tcatgacagg attgccagaa cgggcagtaa ataggacaat     1200
attgttgggc tgctcccttc tgtctcacta gcagagttgt tttaccatgg ggtccagcta     1260
gtaaaagcta ggagttagct gcccaaggtt ggctatgaat aacaccctgc acaacagata     1320
ggccatggcg cctcaggaca tacatgatgg ggtagaaggt gacaagtacc taagcattgc     1380
cttaggtttc aggcacttcc agaagttcca ccacagatct ctggtaacta ctatgccttt     1440
aaggcgactg agctgcacaa ttctctggca tcacggatgg ttagtgttaa tccctggtag     1500
gcatgactct aaaggggttg ggcaggagtc ttcatatctc tttcttggtt tccccagaga     1560
tcagcctggt cctcgaggct ccctcttttg tccttggagg ctggaatcaa ggtcatggtt     1620
cgtagctaca caacacgct gtcctggggc acagtggctc catactacca ttggagttca     1680
agaggtaagc agggttattg gacttcctgt caaacccagg cgctgaggta gggcaggtcc     1740
tcaagatgga gtgaacaaag ttgaagcacc tttcccccaa gacaaggtgc gttggcttgg     1800
aagtccctgt tgcccctgca ccggtggtgc taagatcatg gatgtgggac tgctgtacaa     1860
taccgcaaac accacgcagg tgagtgggtg gcaaggaggc tccctgaatc acgcgtaggc     1920
aggaccctca gcttaagtcc ttgctgtctc ctcaggcatg cctggcgtcc tgcttccagc     1980
agctgatggt ggagatctgc tccagcaaga tcgcagttct gcagccatga acaacatccc     2040
gcctagggta aacctgtcat ctcctttgag gttgctgggg gtctccaagt ccagtcactc     2100
ctaatgggct ccctcaacaa ctcctcaggt cattgctgct accgactcta ccaggatctg     2160
gaacccctcc agcttcctag tatctcccac tgccccagac cttgaaggca agaggggaca     2220
atgatgttgg gagtctggta tcagttcctg ggagagcact gcagatggct gatggtgctg     2280
tctcgcccat aatgtctttg tataaaatct tcgcagggac ttcca                    2325
```

CELL LINES EXPRESSING ENAC AND METHODS USING THEM

CROSS-REFERENCE TO RELATED APPLICATION

This application is a United States National Stage Application under 35 U.S.C. §371 of International Application PCT/US2009/031936, filed Jan. 25, 2009, which claims priority to and the benefit of U.S. Provisional Applications 61/063,219, filed Feb. 1, 2008, and 61/062,371, filed Jan. 25, 2008. The entire disclosures of each of the above applications is incorporated by reference herein.

The Sequence Listing associated with this application is provided in text format in lieu of a paper copy, and is hereby incorporated by reference into the specification. The name of the text file containing the Sequence Listing is 002298_0014_301_Sequence_Listing.TXT. The text file is 76,113 bytes in size, was created on Jul. 23, 2010, and is being submitted electronically via EFS-Web.

FIELD OF THE INVENTION

The invention relates to ENaC and cells and cell lines stably expressing ENaC or proteolyzed forms of ENaC. The invention further provides methods of making such cells and cell lines. The ENaC cells and cell lines provided herein are useful in identifying modulators of ENaC or proteolyzed forms of ENaC.

BACKGROUND

Epithelial sodium channels (ENaC) are multimeric, transmembrane channels located in the apical membranes of a wide variety of epithelial tissues, including the kidneys, lungs and the colon, where they play an important role in homeostasis by regulating salt/water reabsorption. The channels comprise three subunits: alpha or delta, beta and gamma. Modulators of ENaC have therapeutic potential in diseases that are related to ion conductance through ENaC channels, such as hypertension, pulmonary edema and cystic fibrosis.

The discovery of new and improved therapeutics that specifically target ENaC family members has been hampered by the lack of robust, physiologically relevant cell-based systems and more especially such systems that are amenable to high through-put formats for identifying and testing ENaC modulators. Cell-based systems are preferred for drug discovery and validation because they provide a functional assay for a compound as opposed to cell-free systems, which only provide a binding assay. Moreover, cell-based systems have the advantage of simultaneously testing cytotoxicity. Ideally, cell-based systems should also stably and constitutively express the target protein. It is also desirable for a cell-based system to be reproducible. With ENaC, this was not possible because ENaC is a heteromultimeric protein and ENaC expression was cytotoxic. The present invention addresses these problems.

SUMMARY OF THE INVENTION

We have discovered new and useful cells and cell lines that express functional ENaC comprising an alpha or delta subunit, a beta subunit and a gamma subunit. The cells in the cell line may (a) be eukaryotic cells, (b) be mammalian cells, (c) not express ENaC endogenously, or (d) any combination of (a), (b) and (c). In some embodiments, the cells are CHO cells. In other embodiments, the cells are capable of forming polarized monolayers. In the cells or cell lines of the invention, the ENaC may be mammalian, such as mouse, rat or human, preferably human. One or more ENaC subunits may be chimeric, i.e., comprising sequences from two or more sources which can be different species. In some embodiments, a membrane potential dye assay using the cells or cell lines of the invention and NaCl as an agonist has a Z' value of at least 0.8. The cells or cell lines may be stable in culture media without antibiotics. In some embodiments, one or more ENaC subunits are expressed from an introduced nucleic acid encoding it. In some embodiments, one or more ENaC subunits are expressed from an endogenous nucleic acid by gene activation.

In another aspect of the invention, the cells or cell lines express a human ENaC alpha subunit. An ENaC alpha subunit may be a polypeptide having the amino acid sequence set forth in SEQ ID NO: 7, SEQ ID NO: 10, SEQ ID NO: 19, SEQ ID NO: 20, SEQ ID NO: 21; a polypeptide with 95% sequence identity to any one of SEQ ID NOS: 7, 10, 19, 20 and 21 and that is blocked by amiloride; a polypeptide encoded by a nucleotide that hybridizes to any one of SEQ ID NOS: 1, 4 and 22 under stringent conditions; or a polypeptide that is an allelic variant of any one of SEQ ID NOS: 7, 10, 19, 20 and 21. The ENaC alpha subunit may also be encoded by a nucleic acid having the sequence set forth in SEQ ID NO: 1, SEQ ID NO: 4, and SEQ ID NO: 22; a nucleic acid that hybridizes to any one of SEQ ID NOS: 1, 4, and 22 under stringent conditions; a nucleic acid that encodes the polypeptide of any one of SEQ ID NOS: 7, 10, 19, 20 and 21; a nucleic acid with at least 95% sequence identity to any one of SEQ ID NOS: 1, 4 and 22; or a nucleic acid that is an allelic variant of any one of SEQ ID NOS: 1, 4 and 22.

In another aspect of the invention, the cells or cell lines express a human ENaC beta subunit. An ENaC beta subunit may be a polypeptide having the amino acid sequence set forth in SEQ ID NO: 8, SEQ ID NO: 11; a polypeptide with 95% sequence identity to any one of SEQ ID NOS: 8 and 11 and that is blocked by amiloride; a polypeptide encoded by a nucleic acid that hybridizes to any one of SEQ ID NOS: 2, 5 and 23; or a polypeptide that is an allelic variant of any one of SEQ ID NOS: 8 and 11. The ENaC beta subunit may be encoded by a nucleic acid having the sequence set forth in SEQ ID NO: 2, SEQ ID NO: 5, and SEQ ID NO: 23; a nucleic acid that hybridizes to any one of SEQ ID NOS: 2, 5 and 23 under stringent conditions; a nucleic acid that encodes the polypeptide of any one of SEQ ID NOS: 8 and 11; a nucleic acid with at least 95% sequence identity to any one of SEQ ID NOS: 2, 5 and 23; or a nucleic acid that is an allelic variant of any one of SEQ ID NOS: 2, 5 and 23.

In another aspect, the cells or cell lines of the invention express a human ENaC gamma subunit. A gamma ENaC may be a polypeptide having the amino acid sequence set forth in SEQ ID NO: 9, SEQ ID NO: 12; a polypeptide with 95% sequence identity to any one of SEQ ID NOS: 9 and 12 and that is blocked by amiloride; a polypeptide encoded by a nucleic acid that hybridizes to any one of SEQ ID NOS: 3, 6 and 24; and a polypeptide that is an allelic variant of any one of SEQ ID NOS: 9 and 12. An ENaC gamma subunit may be encoded by a nucleic acid having the sequence set forth in SEQ ID NO: 3, SEQ ID NO: 6, and SEQ ID NO: 24; a nucleic acid that hybridizes to any one of SEQ ID NOS: 3, 6 and 24 under stringent conditions; a nucleic acid that encodes the polypeptide of any one of SEQ ID NOS: 9 and 12; a nucleic acid with at least 95% sequence identity to any one of SEQ ID NOS: 3, 6 and 24; and a nucleic acid that is an allelic variant of any one of SEQ ID NOS: 3, 6 and 24.

In another aspect, the cells or cell lines of the invention express a human ENaC delta subunit. A delta ENaC may be a encoded by a nucleic acid having the sequence set forth in SEQ ID NO: 25; a nucleic acid that hybridizes to SEQ ID NO: 25 under stringent conditions; a nucleic acid with at least 95% sequence identity to SEQ ID NO: 25; or a nucleic acid that is an allelic variant of any one of SEQ ID NO: 25.

In some embodiments, the cells or cell lines of the invention are treated with a protease so that the ENaC has a proteolyzed form. In some embodiments, the protease is trypsin.

In another aspect, the invention provides a method for producing the cells or cell lines of the invention comprising the steps of: (a) introducing a first vector comprising a nucleic acid encoding an ENaC alpha or delta subunit, a second vector comprising a nucleic acid encoding an ENaC beta subunit and a third vector comprising a nucleic acid encoding an ENaC gamma subunit into a host cell; (b) introducing into the host cell produced in step (a) a first signaling probe that detects the expression of the ENaC alpha or delta subunit, a second signaling probe that detects the expression of the ENaC beta subunit and a third signaling probe that detects the expression of the ENaC gamma subunit, (c) isolating a cell that expresses the ENaC alpha or delta subunit, the ENaC beta subunit and the ENaC gamma subunit. In some embodiments, the method comprises the additional step of generating a cell line from a cell isolated in step (c). In some embodiments, the host cells (a) are eukaryotic cells; (b) are mammalian cells; (c) do not express ENaC endogenously; or (d) any combination of (a), (b) and (c).

In some embodiments, the method produces an ENaC-expressing cell line wherein the ENaC alpha subunit comprises the amino acid sequence set forth in SEQ ID NO: 7, the ENaC beta subunit comprises the amino acid sequence set forth in SEQ ID NO: 8 and the ENaC gamma subunit comprises the amino acid sequence set forth in SEQ ID NO: 9. In other embodiments, the method produces an ENaC-expressing cell line wherein the ENaC alpha subunit is encoded by a nucleic acid comprising SEQ ID NO: 1, the ENaC beta subunit is encoded by a nucleic acid comprising SEQ ID NO: 2 and the ENaC gamma subunit is encoded by a nucleic acid comprising SEQ ID NO: 3.

In some embodiments, the method of producing cells and cell lines of the invention utilizes flow cytometry to isolate a cell that expresses the ENaC alpha or delta subunit, the ENaC beta subunit and the ENaC gamma subunit. In some embodiments, the method utilizes a signaling probe that fluoresces upon binding to a target sequence and uses a fluorescence activated cell sorter to isolate a cell.

In another aspect, the invention provides a method for identifying a modulator of an ENaC function comprising the step of exposing a cell or cell line of the invention to a test compound and detecting a change in an ENaC function. In some embodiments, the detecting step is selected from a membrane potential assay, electrophysiology assay, a binding assay or an Ussing chamber assay. The modulator may be an ENaC inhibitor, antagonist, partial antagonist, an ENaC agonist, partial agonist or potentiator. Test compounds used in the method may include a small molecule, a chemical moiety, a polypeptide, or an antibody. In other embodiments, the test compound is in a library of compounds. The library may be a small molecule library, a combinatorial library, a peptide library or an antibody library. In some embodiments, the modulator identified with the method of the invention is selective for an enzymatically modified form of ENaC.

In another aspect, the invention provides a method for producing a cell or cell line comprising an enzymatically modified form of ENaC, by exposing a cell or cell line of the invention to a protease, wherein at least one enzymatically modified form of ENaC is generated. In some embodiments, the protease is trypsin.

In another aspect, the invention provides a method of culturing a cell or cell line of the invention that expresses an ENaC comprising the step of culturing cells in media with reduced sodium. In some embodiments, the concentration of sodium in the media is between 9 mM and 140 mM sodium.

BRIEF DESCRIPTION OF THE FIGURES

FIG. 1 depicts cells that were transfected with either vectors containing ENaC subunits (right panel) or empty vector controls (left panel). Light microscopy showed increased cell death in ENaC-expressing cells.

FIG. 2 depicts CHO cells that were transfected with either vectors containing ENaC subunits (right panel) or empty vector controls (left panel). Cells expressing ENaC exhibited increased surface area and volume.

FIG. 3A is a series of histograms showing cells expressing ENaC alpha, beta and gamma subunits as detected by FACS. FIG. 3B depicts the relative expression level of ENaC alpha, beta and gamma subunits. FIG. 3C shows data for the ability of untransfected cells, and cells having various combinations of ENaC subunits to take up sodium and lithium in the presence or absence of amiloride (antagonist).

FIG. 4 shows representative traces from the ENaC membrane potential assay in the presence of added NaCl alone or NaCl plus amiloride. EC50 values for NaCl and 1050 values for amiloride are shown.

FIG. 5 shows that ENaC-expressing cells subjected to a membrane potential dye assay have a Z' of 0.85.

FIG. 6 shows traces produced by a test compound with ENaC inhibiting activity (left panel) and by a compound with ENaC potentiating activity (right panel), identified using an ENaC cell line of the invention in a membrane potential assay.

FIG. 7A shows the membrane potential response for 24 forms of proteolyzed ENaC. FIG. 7B shows the activation of a membrane potential dye in response to the addition of sodium to cell lines expressing each of the 24 proteolyzed variants and the non-proteolyzed form.

FIG. 8 is a dose response curve of amiloride for both non-proteolyzed (filled squares) and one proteolyzed form (open circles) of ENaC. A concentration sufficient to almost completely inhibit non-proteolyzed ENaC was not effective to inhibit Form 24.

FIG. 9 shows graphs depicting the response of 24 proteolyzed forms of ENaC in response to different compounds.

FIG. 10 shows the results of Ussing Chamber assays for potentiating compounds (upper panels) and inhibitory compounds (lower panel).

FIG. 11 shows the results of a taste test for controls and potentiators of a proteolyzed form of ENaC. The effects of compounds on salt taste was assessed by having taste panelists compare saline solutions with or without compound. Potentiators of the proteolyzed form of ENaC were selected as enhancing salt taste compared to control solutions containing NaCl without the potentiators more often than potentiators of the non-proteolyzed form.

DETAILED DISCLOSURE

Figure 1:
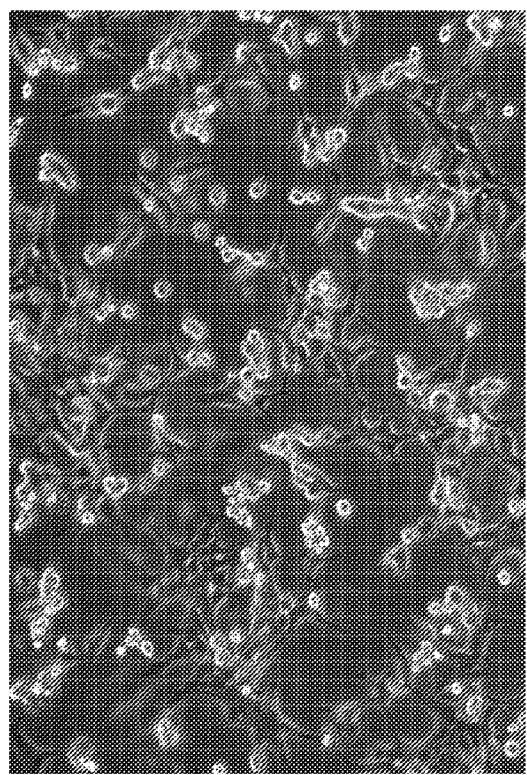
FIG. 1 ENaC induces cytotoxicity.
Figure 1:
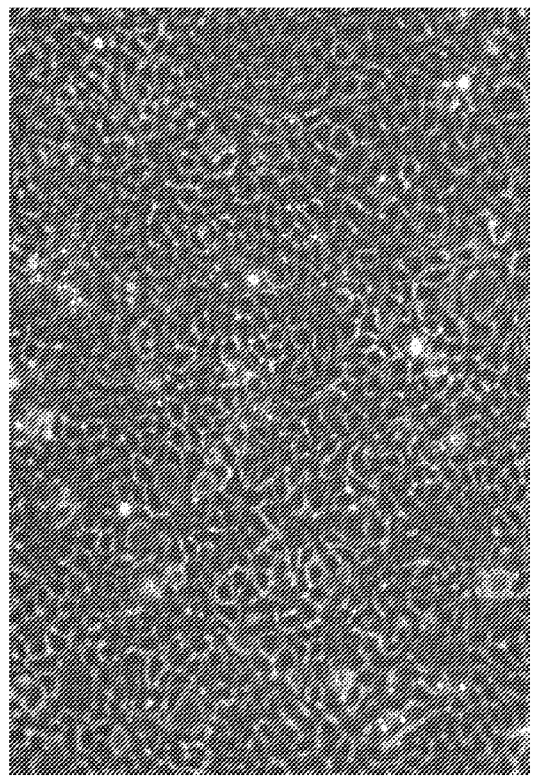

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. Although a number of documents are cited herein, this citation does not constitute an admission that any of these documents forms part of the common general knowledge in the art. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. The materials, methods, and examples are illustrative only and not intended to be limiting.

In order that the present invention may be more readily understood, certain terms are first defined. Additional definitions are set forth throughout the detailed description.

The term "stable" or "stably expressing" is meant to distinguish the cells and cell lines of the invention from cells with transient expression as the terms "stable expression" and "transient expression" would be understood by a person of skill in the art.

The term "cell line" or "clonal cell line" refers to a population of cells that are all progeny of a single original cell. As used herein, cell lines are maintained in vitro in cell culture and may be frozen in aliquots to establish banks of clonal cells.

The term "stringent conditions" or "stringent hybridization conditions" describe temperature and salt conditions for hybridizing one or more nucleic acid probes to a nucleic acid sample and washing off probes that have not bound specifically to target nucleic acids in the sample. Stringent conditions are known to those skilled in the art and can be found in *Current Protocols in Molecular Biology*, John Wiley & Sons, N.Y. (1989), 6.3.1-6.3.6. Aqueous and nonaqueous methods are described in that reference and either can be used. An example of stringent hybridization conditions is hybridization in 6×SSC at about 45° C., followed by at least one wash in 0.2×SSC, 0.1% SDS at 60° C. A further example of stringent hybridization conditions is hybridization in 6×SSC at about 45° C., followed by at least one wash in 0.2×SSC, 0.1% SDS at 65° C. Stringent conditions include hybridization in 0.5M sodium phosphate, 7% SDS at 65° C., followed by at least one wash at 0.2×SSC, 1% SDS at 65° C.

The phrase "percent identical" or "percent identity" in connection with amino acid and/or nucleic acid sequences refers to the similarity between at least two different sequences. This percent identity can be determined by standard alignment algorithms, for example, the Basic Local Alignment Tool (BLAST) described by Altshul et al. ((1990) J. Mol. Biol., 215: 403-410); the algorithm of Needleman et al. ((1970) J. Mol. Biol., 48: 444-453); or the algorithm of Meyers et al. ((1988) Comput. Appl. Biosci., 4: 11-17). A set of parameters may be the Blosum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller ((1989) CABIOS, 4:11-17) that has been incorporated into the ALIGN program (version 2.0), using a PAM120 weight residue table, a gap length penalty of 12 and a gap penalty of 4. The percent identity is usually calculated by comparing sequences of similar length. Protein analysis software matches similar sequences using measures of similarity assigned to various substitutions, deletions and other modifications, including conservative amino acid substitutions. For instance, the GCG Wisconsin Package (Accelrys, Inc.) contains programs such as "Gap" and "Bestfit" that can be used with default parameters to determine sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters. A program in GCG Version 6.1. FASTA (e.g., FASTA2 and FASTA3) provides alignments and percent sequence identity of the regions of the best overlap between the query and search sequences (Pearson, Methods Enzymol. 183:63-98 (1990); Pearson, Methods Mol. Biol. 132:185-219 (2000)). The length of polypeptide sequences compared for identity will generally be at least about 16 amino acid residues, usually at least about 20 residues, more usually at least about 24 residues, typically at least about 28 residues, and preferably more than about 35 residues. The length of a DNA sequence compared for identity will generally be at least about 48 nucleic acid residues, usually at least about 60 nucleic acid residues, more usually at least about 72 nucleic acid residues, typically at least about 84 nucleic acid residues, and preferably more than about 105 nucleic acid residues.

The phrase "substantially as set out," "substantially identical" or "substantially homologous" in connection with an amino acid nucleotide sequence means that the relevant amino acid or nucleotide sequence will be identical to or have insubstantial differences (through conserved amino acid substitutions) in comparison to the sequences that are set out. Insubstantial differences include minor amino acid changes, such as 1 or 2 substitutions in a 50 amino acid sequence of a specified region.

The terms "potentiator", "agonist" or "activator" refer to a compound or substance that increases ion conductance via an ENaC. As used herein, a potentiator or activator may act upon all or upon a specific subset of ENaCs, ENaC subunits or proteolytic isoforms of ENaC.

The terms "inhibitor", "antagonist" or "blocker" refers to a compound or substance that decreases ion conductance via an ENaC. As used herein, an inhibitor or blocker may act upon all or upon a specific subest of ENaCs, ENaC subunits or proteolytic isoforms of ENaC.

The term "modulator" refers to a compound or substance that alters the structure, conformation, biochemical or biophysical properties or functionality of an ENaC either positively or negatively. The modulator can be an ENaC agonist (potentiator or activator) or antagonist (inhibitor or blocker), including partial agonists or antagonists, selective agonists or antagonists and inverse agonists, and can be an allosteric modulator. A substance or compound is a modulator even if its modulating activity changes under different conditions or concentrations or with respect to different forms (i.e., proteolyzed forms) of ENaC. As used herein, a modulator may affect the ion conductance of an ENaC, the response of an ENaC to another regulatory compound or the selectivity of an ENaC. A modulator may also change the ability of another modulator to affect the function of an ENaC A modulator may act upon all or upon a specific subset of ENaCs, ENaC subunits, or proteolytic isoforms of ENaC. Modulators include, but are not limited to, potentiators, activators, inhibitors, agonists, antagonists and blockers.

The phrase "functional ENaC" refers to an ENaC that comprises at least an alpha or delta, beta and a gamma substances and that responds to a known activator such as sodium or a known inhibitor, such as amiloride in substantially the same way as ENaC in a cell that normally expresses ENaC without engineering. ENaC behavior can be determined by, for example, physiological activities and pharmacological responses. Physiological activities include, but are not limited to sodium conductance and lithium conductance. Pharmacological responses include, but are not limited to, inhibition by amiloride.

A "heterologous" or "introduced" ENaC subunit means that the ENaC subunit is encoded by a polynucleotide introduced into a host cell.

This application relates to novel cells and cell lines that have been engineered to express three or more epithelial sodium channel (ENaC) subunits. In some embodiments, the cells or cell lines express three ENaC subunits: an alpha or delta subunit, a beta subunit, and a gamma subunit. In some embodiments, the novel cells or cell lines of the invention express a functional ENaC. In some embodiments the ENaC expressing cells or cell lines are enzymatically treated to generate enzymatically modified forms of ENaC. In other aspects, the invention provides methods of making and using the novel cells and cell lines.

ENaC is a protein that is present in many mammalian tissues, including epithelial cells of the kidney, lung, colon, CNS/brain, heart, vasculature, neurons of arterial baroreceptors, endothelial and vascular smooth muscle cells, eye, mouth, tongue and fallopian tubes. Without being bound by theory, we believe that ENaC dysregulation, dysfunction or improper proteolytic processing may be linked to many disease states including pulmonary disorders such as cystic fibrosis and chronic obstructive pulmonary disease, cardiovascular disorders, renal disorders and infertility.

ENaC is a membrane spanning multimeric protein channel, comprising alpha, beta and gamma subunits. Various stochiometries may be possible, including but not limited to two alpha, one beta, and one gamma; three of each subunit; or one each of each subunit. Delta subunits substitute for the alpha subunits in some or all channels in some tissue types.

According to one embodiment of the invention, the novel cells and cell lines are triply transfected with a nucleic acids individually encoding a ENaC alpha subunit, an ENaC beta subunit, and an ENaC gamma subunit on the same or separate vectors. The novel cell lines of the invention stably express the introduced ENaC subunits. In another embodiment, the novels cells and cells lines have three subunits activated for expression by gene activation. The invention also provides cell lines stably expressing ENaC subunits that have been enzymatically (such as proteolytically) treated to generate enzymatically modified forms of ENaC. The cells and cell lines of the invention comprising intact or enzymatically modified forms of ENaC can be used to identify modulators of ENaC function, including modulators that are specific for a particular ENaC enzymatically modified form. The cells and cell lines can thus be used to obtain information about the properties, activities and roles of individual enzymatically modified forms of ENaC and to identify ENaC modulators with activity for all enzymatically modified forms or on a particular form or subset of forms. These modulators are useful as therapeutics that target differentially modified ENaC forms in disease states or tissues. Because the disregulation of proteolysis of ENaC in vivo, for example, may contribute to an undesired activity or disease state, cells and cell lines of this invention also can be used to screen for modulators that reduce or promote proteolytic processing for therapeutic use where altered of proteolysis may be desired. The cells and cell lines also are useful to identify modulators that have activity with only a subset of proteolytic isoforms of ENaC.

Figure 7:
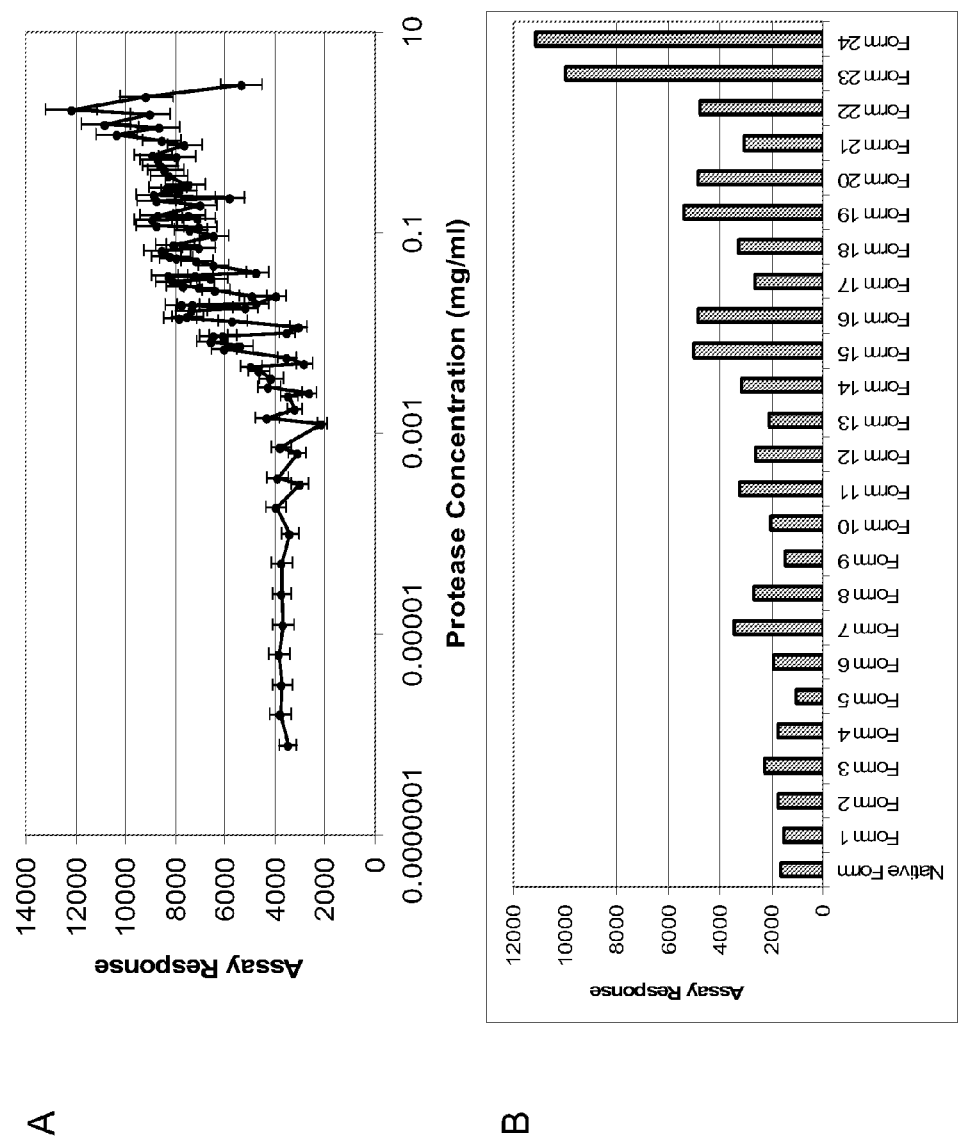
FIG. 7 Proteolysis of ENaC generates novel isoforms.

ENaC also has been proposed as a mammalian salt taste receptor. Within the oral cavity, there are many active proteases including salivary enzymes and bacterially derived proteins, consistent with the proteolysis of ENaC in the oral cavity. As shown herein (FIGS. 7-9), differentially proteolyzed forms of ENaC show varied sensitivity to amiloride, a known blocker of ENaC. Some proteolyzed forms of ENaC also show varied sensitivity to amiloride compared to non-proteolyzed forms of ENaC. Some forms have little or no sensitivity to amiloride. For example, one or a combination of proteolyzed ENaC forms may account for the human salt taste sensory data on the partial but not full block of salt taste by amiloride. Also, ENaC is expressed in various tissues where it has been implicated in diseases where ENaC inhibitors would be expected to be of therapeutic value. Therefore, the use of other (non-amiloride) modulators may be of therapeutic value.

This invention also identifies and solves a difficulty in generating stable ENaC expressing cells and cell lines. As disclosed herein, we have discovered that expression of ENaC is cytotoxic in several host cell lines tested. ENaC expression led to swelling and bursting, resulting in ENaC cytotoxicity. It was further discovered that growing cells and cell lines in low-sodium media alleviated ENaC toxicity and allowed ENaC expressing cells and cell lines to behave in a physiological manner.

In a first aspect, the invention provides cells and cell lines that stably express ENaCs. In some embodiments, the expressed ENaCs conduct sodium and lithium ions and are modulated by amiloride. In further embodiments, the ENaC cells and cell lines of the invention have enhanced properties compared to cells and cell lines made by conventional methods. For example, the ENaC cells and cell lines have enhanced stability of expression (even when maintained in culture without selective antibiotics) and result in high Z' values. Cells and cell lines of the invention can also be treated with enzymes such as trypsin to generate, for example, proteolyzed forms of ENaC. In other aspects, the invention provides methods of making and using the ENaC cells and cell lines.

In various embodiments, the cell or cell line of the invention expresses ENaC alpha, beta and gamma subunits at a consistent level of expression for at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200 days or over 200 days, where consistent expression refers to a level of expression that does not vary by more than: 1%, 2%, 3%, 4%, 5%, 6%, 7%, 8% 9% or 10% over 2 to 4 days of continuous cell culture; 2%, 4%, 6%, 8%, 10% or 12% over 5 to 15 days of continuous cell culture; 2%, 4%, 6%, 8%, 10%, 12%, 14%, 16%, 18% or 20% over 16 to 20 days of continuous cell culture; 2%, 4%, 6%, 8%, 10%, 12%, 14%, 16%, 18%, 20%, 22%, 24% over 21 to 30 days of continuous cell culture; 2%, 4%, 6%, 8%, 10%, 12%, 14%, 16%, 18%, 20%, 22%, 24%, 26%, 28% or 30% over 30 to 40 days of continuous cell culture; 2%, 4%, 6%, 8%, 10%, 12%, 14%, 16%, 18%, 20%, 22%, 24%, 26%, 28% or 30% over 41 to 45 days of continuous cell culture; 2%, 4%, 6%, 8%, 10%, 12%, 14%, 16%, 18%, 20%, 22%, 24%, 26%, 28% or 30% over 45 to 50 days of continuous cell culture; 2%, 4%, 6%, 8%, 10%, 12%, 14%, 16%, 18%, 20%, 22%, 24%, 26%, 28%, 30% or 35% over 45 to 50 days of continuous cell culture, 2%, 4%, 6%, 8%, 10%, 12%, 14%, 16%, 18%, 20%, 22%, 24%, 26%, 28% or 30% over 50 to 55 days of continuous cell culture, 2%, 4%, 6%, 8%, 10%, 12%, 14%, 16%, 18%, 20%, 22%, 24%, 26%, 28%, 30% or 35% over 50 to 55 days of continuous cell culture; 1%, 2%, 3%, 4%, 5%, 10%, 15%, 20%, 25%, 30%, 35% or 40% over 55 to 75 days of continuous cell culture; 1%, 2%, 3%, 4%, 5%, 5%, 10%, 15%, 20%, 25%, 30%, 35%, 40% or 45% over 75 to 100 days of continuous cell culture; 1%, 2%, 3%, 4%, 5%, 5%, 10%, 15%, 20%, 25%, 30%, 35%, 40% or 45% over 101 to 125 days of continuous cell culture; 1%, 2%, 3%, 4%, 5%, 5%, 10%, 15%, 20%, 25%, 30%, 35%, 40% or 45% over 126 to 150 days of continuous cell culture; 1%, 2%, 3%, 4%, 5%, 5%, 10%, 15%, 20%, 25%, 30%, 35%, 40% or 45% over 151 to 175 days of continuous cell culture; 1%, 2%, 3%, 4%, 5%, 5%, 10%, 15%, 20%, 25%, 30%, 35%, 40% or 45% over 176 to 200 days of continuous cell culture; 1%, 2%, 3%, 4%, 5%, 5%, 10%, 15%, 20%, 25%, 30%, 35%, 40% or 45% over more than 200 days of continuous cell culture.

According to the invention, the ENaC expressed by a cell or cell line can be from any mammal, including rat, mouse, rabbit, goat, dog, cow, pig or primate. The alpha (and delta), beta and gamma subunits can be from the same or different species. In a preferred embodiment, the ENaC is human ENaC, including human alpha and/or human delta, human beta, and human gamma subunits. Also within the invention are engineered cells and cell lines stably expressing a moleculed selected from the group consisting of: Unc-105, MEC-4, MEC-10, MEC-2, RPK, FaNaC(Ha), FaNaC(Ht), ASIC1a, ASIC1b, ASIC2a, ASIC3, ASIC1a/2a, ASIC2a/2b, ASIC2a/3, ASIC2b/3, BLINaC, h1NaC.

In some embodiments, a cell or cell line of the invention may comprise a nucleic acid sequence that encodes any one of a human ENaC alpha subunit (SEQ ID NO: 1); a human ENaC beta subunit (SEQ ID NO: 2); and a human ENaC gamma subunit (SEQ ID NO: 3); or a rat ENaC alpha subunit (SEQ ID NO: 4); a rat ENaC beta subunit (SEQ ID NO: 5); and a rat ENaC gamma subunit (SEQ ID NO: 6); or either a mouse ENaC alpha subunit (SEQ ID NO: 22) or a mouse ENaC delta subunit (SEQ ID NO: 25); a mouse ENaC beta subunit (SEQ ID NO: 23); and a mouse ENaC gamma subunit (SEQ ID NO: 24). In other embodiments, a cell or cell line of the invention may comprise an amino acid that is a human ENaC alpha subunit isoform 1 (SEQ ID NO: 7), a human ENaC alpha subunit isoform 2 (SEQ ID NO: 19), a human ENaC alpha subunit isoform 3 (SEQ ID NO: 20), or a human ENaC alpha subunit isoform 4 (SEQ ID NO: 21); a human ENaC beta subunit (SEQ ID NO: 8); and a human ENaC gamma subunit (SEQ ID NO: 9); or a rat ENaC alpha subunit (SEQ ID NO: 10); a rat ENaC beta subunit (SEQ ID NO: 11); or a rat ENaC gamma subunit (SEQ ID NO: 12).

The nucleic acid encoding the ENaC alpha (and delta), beta, or gamma subunit can be genomic DNA or cDNA. In some embodiments, the nucleic acid encoding the ENaC subunit comprises one or more substitutions, mutations or deletions, as compared to a wild-type ENaC, that may or may not result in an amino acid substitution. In some embodiments, the nucleic acid is a fragment of the nucleic acid sequence provided. Such ENaCs that are fragments or have such modifications retain at least one biological property of an ENaC, e.g., its ability to conduct sodium, conduct lithium, or be modulated by amiloride. The invention encompasses cells and cell lines stably expressing a subunit-encoding nucleotide sequence that is at least about 85% identical to a sequence disclosed herein. In some embodiments, the subunit-encoding sequence identity is at least 85%, 90%, 95%, 96%, 97%, 98%, 99% or higher compared to a subunit sequence provided herein. The invention also encompasses cells and cell lines wherein a nucleic acid encoding an ENaC subunit hybridizes under stringent conditions to a nucleic acid provided herein encoding the subunit.

In some embodiments, the cell or cell line comprises an ENaC subunit-encoding nucleic acid sequence comprising a substitution compared to a sequence provided herein by at least one but less than 10, 20, 30, or 40 nucleotides, up to or equal to 1%, 5%, 10% or 20% of the nucleotide sequence or from a sequence substantially identical thereto (e.g., a sequence at least 85%, 90%, 95%, 96%, 97%, 98%, 99% or higher identical thereto, or that is capable of hybridizing under stringent conditions to the sequences disclosed). In some embodiments, the cell or cell line comprises an ENaC subunit-encoding nucleic acid sequence comprising an insertion into or deletion from the sequences provided herein by less than 10, 20, 30, or 40 nucleotides up to or equal to 1%, 5%, 10% or 20% of the nucleotide sequence or from a sequence substantially identical thereto (e.g., a sequence at least 85%, 90%, 95%, 96%, 97%, 98%, 99% or higher identical thereto, or that is capable of hybridizing under stringent conditions to the sequences disclosed). The substitutions, insertions and deletions described herein may occur in any of the polynucleotides encoding ENaC subunits in the cells or cell lines of the invention.

In some embodiments, where the nucleic acid substitution or modification results in an amino acid change, such as an amino acid substitution, the native amino acid may be replaced by a conservative or non-conservative substitution. In some embodiments, the sequence identity between the original and modified polypeptide sequence can differ by about 1%, 5%, 10% or 20% of the polypeptide sequence or from a sequence substantially identical thereto (e.g., a sequence at least 85%, 90%, 95%, 96%, 97%, 98%, 99% or higher identical thereto). Those of skill in the art will understand that a conservative amino acid substitution is one in which the amino acid side chains are similar in structure and/or chemical properties and the substitution should not substantially change the structural characteristics of the parent sequence. In embodiments comprising a nucleic acid comprising a mutation, the mutation may be a random mutation or a site-specific mutation.

Conservative modifications will produce ENaCs having functional and chemical characteristics similar to those of the unmodified ENaC. A "conservative amino acid substitution" is one in which an amino acid residue is substituted by another amino acid residue having a side chain R group with similar chemical properties to the parent amino acid residue (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson, Methods Mol. Biol. 243:307-31 (1994).

Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine.

Alternatively, a conservative amino acid substitution is any change having a positive value in the PAM250 log-likelihood matrix disclosed in Gonnet et al., Science 256: 1443-45 (1992). A "moderately conservative" replacement is any change having a nonnegative value in the PAM250 log-likelihood matrix.

Any ENaC alpha subunit from any species may be co-expressed with any ENaC beta subunit from any species, and any ENaC gamma subunit from any species in a cell or cell line of the invention. Similarly, any ENaC delta subunit from any species may be co-expressed with any ENaC beta subunit from any species, and any ENaC gamma subunit from any species in a cell line of the invention. In some embodiments, an ENaC subunit may be a chimeric subunit comprising sequences form two or more species. In some embodiments, the novel cell and cell line stably expresses human ENaC subunits, for example a cell or cell line that expresses at least one human ENaC alpha subunit (SEQ ID NO: 7); at least one human ENaC beta subunit (SEQ ID NO: 8); and at least one human ENaC gamma subunit (SEQ ID NO: 9). In some embodiments, the novel cell line is triply transfected to expresses a human ENaC alpha subunit, a human ENaC beta subunit and a human ENaC gamma subunit.

The invention further encompasses cells or cell lines that comprise an ENaC in which one or more subunits have a proteolyzed form and further encompasses a collection or panel of cell lines each comprising a different proteolyzed isoform. Such cells, cell lines and collections are useful to determine the activity of a proteolyzed isoform and the differential activity of a modulator on different proteolyzed isoforms of ENaC. In particular embodiments, ENaC expressing cells are exposed to one or more proteases at varying concentrations for varying times. In some embodiments the protease concentration is above zero but less than 0.1 ng/ml, about 0.1 ng/ml; 1 ng/ml; 10 ng/ml; 50 ng/ml; 100 ng/ml; 250 ng/ml; 500 ng/ml, 750 ng/ml, 1 µg/ml, 1.5 µg/ml, 2 µg/ml, 2.5 µg/ml, 3 µg/ml, 4 µg/ml, 5 µg/ml, 6 µg/ml, 7 µg/ml, 8 µg/ml, 9 µg/ml, 10 µg/ml, 100 µg/ml, 0.5 mg/ml, 1 mg/ml, 1.5 mg/ml, 2 mg/ml, 2.5 mg/ml, 3 mg/ml, 3.5 mg/ml, 4 mg/ml, 4.5 mg/ml, 5 mg/ml, 5.5 mg/ml, 6 mg/ml, 6.5 mg/ml, 7 mg/ml, 7.5 mg/ml, 8 mg/ml, 8.5 g/ml, 9 mg/ml, 9.5 mg/ml, 10 mg/ml or even greater concentrations or any concentration in between those listed. That is, the enzyme concentration may be in picomolar up to millimolar range. In some embodiments, ENaC expressing cells are exposed to protease for about 1 sec, 5 sec, 10 sec, 15 sec, 30 sec, 45 sec, 1 min, 2 min, 3 min, 4 min, 5 min, 6 min, 7 min, 8 min, 9 min, 10 min, 15 min, 20 min, 30 min, 60 min, 90 min, longer than 90 min, or any length of time in between. Non-limiting examples of proteases include furin, trypsin, chymotrypsin, elastase, thrombin, plasmin, kallikrein, and acrosin, PACE4, PC5/6B, PC7, channel-activating protease-1 (CAP-1), prostatin, mCAP-2, human transmembrane protease serine 4 (TMPRSS4), mCAP-3, or a protease within saliva, stomach secretions or bacterial lysates, or any protease which hydrolyzes ENaC, or a combination of these. In other embodiments, enzymatically modified or proteolyzed forms of ENaC are generated by transfecting a cell or cell line expressing ENaC with a gene encoding the enzyme (e.g., protease) and stimulating or inducing its expression. Proteolyzed forms of ENaC or of an ENaC subunit may be characterized, for example, by analysis of peptides released into the media following proteolysis, such as by mass spectrometry, by analysis of the proteolyzed ENaC such as by Western blot or other immunodetection or by other suitable means that are well known in the art.

In some embodiments, the ENaC subunit-encoding nucleic acid sequence further comprises a tag. Such tags may encode, for example, a HIS tag, a myc tag, a hemagglutinin (HA) tag, protein C, VSV-G, FLU, yellow fluorescent protein (YFP), green fluorescent protein, FLAG, BCCP, maltose binding protein tag, Nus-tag, Softag-1, Softag-2, Strep-tag, S-tag, thioredoxin, GST, V5, TAP or CBP. A tag may be used as a marker to determine ENaC expression levels, intracellular localization, protein-protein interactions, ENaC regulation, or ENaC function. Tags may also be used to purify or fractionate ENaC.

Host cells used to produce a cell or cell line of the invention may express in their native state one or more endogenous ENaC subunits or lack expression of any ENaC subunit. The host cell may be a primary, germ, or stem cell, including an embryonic stem cell. The host cell may also be an immortalized cell. Primary or immortalized host cells may be derived from mesoderm, ectoderm or endoderm layers of eukaryotic organisms. The host cell may be endothelial, epidermal, mesenchymal, neural, renal, hepatic, hematopoietic, or immune cells. For example, the host cells may be intestinal crypt or villi cells, clara cells, colon cells, intestinal cells, goblet cells, enterochromafin cells, enteroendocrine cells. The host cells may be eukaryotic, prokaryotic, mammalian, human, primate, bovine, porcine, feline, rodent, marsupial, murine or other cells. The host cells may also be nonmammalian, such as yeast, insect, fungus, plant, lower eukaryotes and prokaryotes. Such host cells may provide backgrounds that are more divergent for testing ENaC modulators with a greater likelihood for the absence of expression products provided by the cell that may interact with the target. In preferred embodiments, the host cell is a mammalian cell. Examples of host cells that may be used to produce a cell or cell line of the invention include but are not limited to: Chinese hamster ovary (CHO) cells, established neuronal cell lines, pheochromocytomas, neuroblastomas fibroblasts, rhabdomyosarcomas, dorsal root ganglion cells, NSO cells, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1

(ATCC CCL 26), MRC-5 (ATCC CCL 171), L-cells, HEK-293 (ATCC CRL1573) and PC12 (ATCC CRL-1721), HEK293T (ATCC CRL-11268), RBL (ATCC CRL-1378), SH-SY5Y (ATCC CCL-2266), MDCK (ATCC CCL-34), SJ-RH30 (ATCC CRL-2061), HepG2 (ATCC HB-8065), ND7/23 (ECACC 92090903), CHO (ECACC 85050302), Vero (ATCC CCL 81), Caco-2 (ATCC HTB 37), K562 (ATCC CCL 243), Jurkat (ATCC TIB-152), Per.C6 (Crucell, Leiden, The Netherlands), Huvec (ATCC Human Primary PCS 100-010, Mouse CRL 2514, CRL 2515, CRL 2516), HuH-7D12 (ECACC 01042712), 293 (ATCC CRL 10852), A549 (ATCC CCL 185), IMR-90 (ATCC CCL 186), MCF-7 (ATC HTB-22), U-20S (ATCC HTB-96), T84 (ATCC CCL 248), or any established cell line (polarized or nonpolarized) or any cell line available from repositories such as American Type Culture Collection (ATCC, 10801 University Blvd. Manassas, Va. 20110-2209 USA) or European Collection of Cell Cultures (ECACC, Salisbury Wiltshire SP4 0JG England). In some embodiments, the host cell is not a CHO cell.

In one embodiment, the host cell is an embryonic stem cell that is then used as the basis for the generation of transgenic animals. In some embodiments one or more subunits may be expressed with desired temporal and/or tissue specific expression. Embryonic stem cells stably expressing at least one ENaC subunit, or all three ENaC subunits, and preferably a functional introduced ENaC, may be implanted into organisms directly, or their nuclei may be transferred into other recipient cells and these may then be implanted, or they may be used to create transgenic animals.

As will be appreciated by those of skill in the art, any vector that is suitable for use with the host cell may be used to introduce a nucleic acid encoding an ENaC subunit into the host cell. The vectors comprising the various ENaC subunits may be the same type or may be of different types. Examples of vectors that may be used to introduce the ENaC subunit encoding nucleic acids into host cells include but are not limited to plasmids, viruses, including retroviruses and lentiviruses, cosmids, artificial chromosomes and may include for example, pCMVScript, pCDNA3.1 Hygro, pcDNA3.1neo, pcDNA3.1puro, pSV2neo, pIRES puro, pSV2 zeo. In some embodiments, the vectors comprise expression control sequences such as constitutive or conditional promoters. One of ordinary skill in the art will be able to select such sequences. For example, suitable promoters include but are not limited to CMV, TK, SV40 and EF-1a. In some embodiments, the promoters are inducible, temperature regulated, tissue specific, repressible, heat-shock, developmental, cell lineage specific, eukaryotic, prokaryotic or temporal promoters or a combination or recombination of unmodified or mutagenized, randomized, shuffled sequences of any one or more of the above. In other embodiments, ENaC is expressed by gene activation or when a gene encoding an ENaC subunit is episomal. Nucleic acids encoding ENaC subunits are preferably constitutively expressed.

In some embodiments, the vector lacks a selectable marker or drug resistance gene. In other embodiments, the vector optionally comprises a nucleic acid encoding a selectable marker such as a protein that confers drug or antibiotic resistance. Each vector for a sequence encoding a different ENaC subunit may have the same or a different drug resistance or other selectable marker. If more than one of the drug resistance markers are the same, simultaneous selection may be achieved by increasing the level of the drug. Suitable markers will be well-known to those of skill in the art and include but are not limited to genes conferring resistance to any one of the following: Neomycin/G418, Puromycin, hygromycin, Zeocin, methotrexate and blasticidin. Although drug selection (or selection using any other suitable selection marker) is not a required step, it may be used to enrich the transfected cell population for stably transfected cells, provided that the transfected constructs are designed to confer drug resistance. If subsequent selection of cells expressing at least three ENaC subunits is accomplished using signaling probes, selection too soon following transfection can result in some positive cells that may only be transiently and not stably transfected. However, this can be minimized by allowing sufficient cell passage allowing for dilution of transient expression in transfected cells.

In some embodiments, the vector comprises a nucleic acid sequence encoding an RNA tag sequence. "Tag sequence" refers to a nucleic acid sequence that is an expressed RNA or portion of an RNA that is to be detected by a signaling probe. Signaling probes may detect a variety of RNA sequences. Any of these RNAs may be used as tags. Signaling probes may be directed against the RNA tag by designing the probes to include a portion that is complementary to the sequence of the tag. The tag sequence may be a 3' untranslated region of the plasmid that is cotranscribed and comprises a target sequence for signaling probe binding. The RNA encoding the gene of interest may include the tag sequence or the tag sequence may be located within a 5'-untranslated region or 3'-untranslated region. In some embodiments, the tag is not with the RNA encoding the gene of interest. The tag sequence can be in frame with the protein-coding portion of the message of the gene or out of frame with it, depending on whether one wishes to tag the protein produced. Thus, the tag sequence does not have to be translated for detection by the signaling probe. The tag sequences may comprise multiple target sequences that are the same or different, wherein one signaling probe hybridizes to each target sequence. The tag sequences may encode an RNA having secondary structure. The structure may be a three-arm junction structure. Examples of tag sequences that may be used in the invention, and to which signaling probes may be prepared, include but are not limited to the RNA transcript of epitope tags such as, for example, a HIS tag, a myc tag, a hemagglutinin (HA) tag, protein C, VSV-G, FLU, yellow fluorescent protein (YFP), green fluorescent protein, FLAG, BCCP, maltose binding protein tag, Nus-tag, Softag-1, Softag-2, Strep-tag, S-tag, thioredoxin, GST, V5, TAP or CBP. As described herein, one of ordinary skill in the art could create his or her own RNA tag sequences.

In another aspect of the invention, cells and cell lines of the invention have enhanced stability as compared to cells and cell lines produced by conventional methods. To identify stable expression, a cell or cell line's expression of each ENaC subunit is measured over a timecourse and the expression levels are compared. Stable cell lines will continue expressing ENaC alpha or delta, beta and gamma subunits throughout the timecourse. In some aspects of the invention, the timecourse may be for at least one week, two weeks, three weeks, etc., or at least one month, or at least two, three, four, five, six, seven, eight or nine months, or any length of time in between. Isolated cells and cell lines can be further characterized, such as by qRT-PCR and single end-point RT-PCR to determine the absolute amounts and relative amounts of each ENaC subunit being expressed. In some embodiments, stable expression is measured by comparing the results of functional assays over a timecourse. The measurement of stability based on functional assay provides the benefit of identifying clones that not only stably express the mRNA of the gene of interest, but also stably produce and properly process (e.g., post-translational modification, subunit assembly, and localization within the cell) the protein encoded by the gene of interest that functions appropriately.

Cells and cell lines of the invention have the further advantageous property of providing assays with high reproducibility as evidenced by their Z' factor. See Zhang J H, Chung T D, Oldenburg K R, "A Simple Statistical Parameter for Use in Evaluation and Validation of High Throughput Screening Assays." *J. Biomol. Screen.* 1999; 4(2):67-73. Z' values pertain to the quality of a cell or cell line because it reflects the degree to which a cell or cell line will respond consistently to modulators. $Z'$ is a statistical calculation that takes into account the signal-to-noise range and signal variability (i.e., from well to well) of the functional response to a reference compound across a multiwell plate. $Z'$ is calculated using data obtained from multiple wells with a positive control and multiple wells with a negative control. The ratio of their combined standard deviations multiplied by three to the difference in their mean values is subtracted from one to give the $Z'$ factor, according the equation below:

$$Z' \text{ factor}=1-((3\sigma_{positive\ control}+3\sigma_{negative\ control})/(\mu_{positive\ control}-\mu_{negative\ control}))$$

The theoretical maximum $Z'$ factor is 1.0, which would indicate an ideal assay with no variability and limitless dynamic range. As used herein, a "high Z'" refers to a Z' factor of Z' of at least 0.6, at least 0.7, at least 0.75 or at least 0.8, or any decimal in between 0.6 and 1.0. In the case of a complex target such as ENaC, a high Z' means a Z' of at least 0.4 or greater. A score less than 0 is undesirable because it indicates that there is overlap between positive and negative controls. In the industry, for simple cell-based assays, Z' scores up to 0.3 are considered marginal scores, Z' scores between 0.3 and 0.5 are considered acceptable, and Z' scores above 0.5 are considered excellent. Cell-free or biochemical assays may approach higher Z' scores, but $Z'$ scores for cell-based systems tend to be lower because cell-based systems are complex.

As those of ordinary skill in the art will recognize, historically, cell-based assays using cells expressing even a single chain protein do not typically achieve a Z' higher than 0.5 to 0.6. Cells with engineered expression (either with introduced coding sequences or gene activation methods) of multi-subunit proteins, if even reported, would be lower due to their added complexity. Such cells would not be reliable to use in an assay because the results are not reproducible. Cells and cell lines of the invention, on the other hand, have high Z' values and advantageously produce consistent results in assays. ENaC expression cells and cell lines of the invention provided the basis for high throughput screening (HTS) compatible assays because they generally have $Z'$ factors at least 0.7. In some aspects of the invention, the cells and cell lines result in Z' of at least 0.3, at least 0.4, at least 0.5, at least 0.6, at least 0.7, or at least 0.8. Even Z' values of at least 0.3-0.4 for ENaC-expressing cell are advantageous because ENaC is a multigene target, such as ENaC, because historically, such targets have been difficult to express. In other aspects of the invention, the cells and cell lines of the invention result in a Z' of at least 0.7, at least 0.75 or at least 0.8 maintained for multiple passages, e.g., between 5-20 passages, including any integer in between 5 and 20. In some aspects of the invention, the cells and cell lines result in a Z' of at least 0.7, at least 0.75 or at least 0.8 maintained for 1, 2, 3, 4 or 5 weeks or 2, 3, 4, 5, 6, 7, 8 or 9 months, including any period of time in between.

Also according to the invention, cells and cell lines that express a form of a naturally occurring ENaC, as well as cells and cell lines that express a proteolyzed form of ENaC, can be characterized for sodium ion conductance and lithium ion conductance. In some embodiments, the cells and cell lines of the invention express ENaC with "physiologically relevant" activity. As used herein, physiological relevance refers to a property of a cell or cell line expressing an ENaC whereby the ENaC conducts sodium and lithium ions as a naturally occurring ENaC of the same type (e.g., an $\alpha\beta\gamma$-ENaC behaves as an $\alpha\beta\gamma$-ENaC and a $\delta\beta\gamma$-ENaC behaves as a $\delta\beta\gamma$-ENaC) and responds to modulators in the same ways that naturally occurring ENaC of the same type is modulated by the same compounds. ENaC cells and cell lines of this invention, including some proteolyzed forms of ENaC, preferably demonstrate comparable function to cells that normally express native ENaC in a suitable assay, such as a membrane potential assay using sodium as the ion conducted by ENaC, a membrane potential assay using lithium as the ion conducted by ENaC, electrophysiology or by inhibition with amiloride. Such comparisons are used to determine a cell or cell line's physiological relevance. "Sip and spit" taste tests using a panel of trained taste testers also may be used to further validate ENaC physiological relevance in cells and cell lines of the invention. The results of sip and spit taste tests using modulators identified via screening of non-proteolyzed or proteolyzed forms of ENaC can be used to validate the physiological relevance of these proteolyzed forms.

In some embodiments, the cells and cell lines of the invention have increased sensitivity to modulators of ENaC. Cells and cell lines of the invention respond to modulators and conduct sodium and lithium ions with physiological range $EC_{50}$ or $IC_{50}$ values for ENaC. As used herein, $EC_{50}$ refers to the concentration of a compound or substance required to induce a half-maximal activating response in the cell or cell line. As used herein, $IC_{50}$ refers to the concentration of a compound or substance required to induce a half-maximal inhibitory response in the cell or cell line. $EC_{50}$ and $IC_{50}$ values may be determined using techniques that are well-known in the art, for example, a dose-response curve that correlates the concentration of a compound or substance to the response of the ENaC-expressing cell line. Sodium chloride and lithium chloride $EC_{50}$ and $IC_{50}$ values for the ENaC-expressing cells and cell lines of the invention were within the ranges established for naturally occurring ENaCs. For example, the $EC_{50}$ for sodium chloride in a cell line of the invention is about 50 mM, the $EC_{50}$ for lithium chloride is about 35 mM, and the $IC_{50}$ for amiloride is sub-micromolar to low micromolar, e.g. single digit micromolar, for example, 0.7 µM or less.

A further advantageous property of the ENaC cells and cell lines of the inventions, flowing from the physiologically relevant function of the ENaC is that modulators identified in initial screening are functional in secondary functional assays, e.g., Ussing chamber assays or electrophysiology. As those of ordinary skill in the art will recognize, compounds identified in initial screening assays typically must be modified, such as by combinatorial chemistry, medicinal chemistry or synthetic chemistry, for their derivatives or analogs to be functional in secondary functional assays. However, due to the high physiological relevance of the present ENaC cells and cell lines, many compounds identified therewith are functional without modification.

One aspect of the invention provides a collection of clonal cells and cell lines, each expressing the same ENaC, or different ENaCs, including different proteolyzed forms of ENaC subunits. The collection may include, for example, cells or cell lines expressing combinations of different subunits, or full length or fragments of subunits. The collection may also include, for example, proteolyzed forms of ENaC.

To make cells and cell lines of the invention, one can use, for example, the technology described in U.S. Pat. No. 6,692,965 and International Patent Publication WO/2005/079462. Both of these documents are incorporated herein by reference in their entirety for all purposes. This technology provides real-time assessment of millions of cells such that any desired number of clones (from hundreds to thousands of clones) may be selected. Using cell sorting techniques, such as flow cytometric cell sorting (e.g., with a FACS machine) or magnetic cell sorting (e.g., with a MACS machine), one cell per well may be automatically deposited with high statistical confidence in a culture vessel (such as a 96 well culture plate). The speed and automation of the technology allows multigene cell lines to be readily isolated.

Using the technology, the RNA sequence for each ENaC subunit may be detected using a signaling probe, also referred to as a molecular beacon or fluorogenic probe. In some embodiments, the molecular beacon recognizes a target tag sequence as described above. In another embodiment, the molecular beacon recognizes a sequence within the ENaC subunit itself. Signaling probes may be directed against the RNA tag or ENaC subunit sequence by designing the probes to include a portion that is complementary to the RNA sequence of the tag or the ENaC subunit, respectively.

Nucleic acids comprising a sequence encoding an ENaC subunit, or the sequence of an ENaC subunit and a tag sequence, and optionally a nucleic acid encoding a selectable marker may be introduced into selected host cells by well known methods. The methods include but not limited to transfection, viral delivery, protein or peptide mediated insertion, coprecipitation methods, lipid based delivery reagents (lipofection), cytofection, lipopolyamine delivery, dendrimer delivery reagents, electroporation or mechanical delivery. Examples of transfection reagents are GENEPORTER, GENEPORTER2, LIPOFECTAMINE, LIPOFECTAMINE 2000, FUGENE 6, FUGENE HD, TFX-10, TFX-20, TFX-50, OLIGOFECTAMINE, TRANSFAST, TRANSFECTAM, GENESHUTTLE, TROJENE, GENESILENCER, X-TREMEGENE, PERFECTIN, CYTOFECTIN, SIPORT, UNIFECTOR, SIFECTOR, TRANSIT-LT1, TRANSIT-LT2, TRANSIT-EXPRESS, IFECT, RNAI SHUTTLE, METAFECTENE, LYOVEC, LIPOTAXI, GENEERASER, GENEJUICE, CYTOPURE, JETSI, JETPEI, MEGAFECTIN, POLYFECT, TRANSMESSANGER, RNAiFECT, SUPERFECT, EFFECTENE, TF-PEI-KIT, CLONFECTIN, AND METAFECTINE.

Following introduction of the ENaC coding sequences or the ENaC activation sequences into host cells and optional subsequent drug selection, molecular beacons (e.g., fluorogenic probes) are introduced into the cells and cell sorting is used to isolate cells positive for their signals. Multiple rounds of sorting may be carried out, if desired. In one embodiment, the flow cytometric cell sorter is a FACS machine. MACS (magnetic cell sorting) or laser ablation of negative cells using laser-enabled analysis and processing can also be used. According to this method, cells expressing at least one alpha or delta, one beta and one gamma subunit are detected and recovered The ENaC subunit sequences may be integrated at different locations of the genome in the cell. The expression level of the introduced genes encoding the ENaC subunits may vary based upon integration site. The skilled worker will recognize that sorting can be gated for any desired expression level. Further, stable cell lines may be obtained wherein one or more of the introduced genes encoding an ENaC subunit is episomal or results from gene activation.

Signaling probes useful in this invention are known in the art and generally are oligonucleotides comprising a sequence complementary to a target sequence and a signal emitting system so arranged that no signal is emitted when the probe is not bound to the target sequence and a signal is emitted when the probe binds to the target sequence. By way of non-limiting illustration, the signaling probe may comprise a fluorophore and a quencher positioned in the probe so that the quencher and fluorophore are brought together in the unbound probe. Upon binding between the probe and the target sequence, the quencher and fluorophore separate, resulting in emission of signal. International publication WO/2005/079462, for example, describes a number of signaling probes that may be used in the production of the cells and cell lines of this invention. Where tag sequences are used, the vector for each of the ENaC subunit can comprise the same or a different tag sequence. Whether the tag sequences are the same or different, the signaling probes may comprise different signal emitters, such as different colored fluorophores and the like so that (RNA) expression of each subunit may be separately detected. By way of illustration, the signaling probe that specifically detects ENaC alpha subunit mRNA can comprise a red fluorophore, the probe that detects the first ENaC beta subunit (RNA) can comprise a green fluorophore and the probe that detects the ENaC gamma subunit (RNA) can comprise a yellow fluorophore. Those of skill in the art will be aware of other means for differentially detecting the expression of the three subunits with a signaling probe in a triply transfected cell.

Nucleic acids encoding signaling probes may be introduced into the selected host cell by any of numerous means that will be well-known to those of skill in the art, including but not limited to transfection, coprecipitation methods, lipid based delivery reagents (lipofection), cytofection, lipopolyamine delivery, dendrimer delivery reagents, electroporation or mechanical delivery. Examples of transfection reagents are GENEPORTER, GENEPORTER2, LIPOFECTAMINE, LIPOFECTAMINE 2000, FUGENE 6, FUGENE HD, TFX-10, TFX-20, TFX-50, OLIGOFECTAMINE, TRANSFAST, TRANSFECTAM, GENESHUTTLE, TROJENE, GENESILENCER, X-TREMEGENE, PERFECTIN, CYTOFECTIN, SIPORT, UNIFECTOR, SIFECTOR, TRANSIT-LT1, TRANSIT-LT2, TRANSIT-EXPRESS, IFECT, RNAI SHUTTLE, METAFECTENE, LYOVEC, LIPOTAXI, GENEERASER, GENEJUICE, CYTOPURE, JETSI, JETPEI, MEGAFECTIN, POLYFECT, TRANSMESSANGER, RNAiFECT, SUPERFECT, EFFECTENE, TF-PEI-KIT, CLONFECTIN, AND METAFECTINE.

In one embodiment, the signaling probes are designed to be complementary to either a portion of the RNA encoding a ENaC subunit or to portions of their 5' or 3' untranslated regions. Even if the signaling probe designed to recognize a messenger RNA of interest is able to detect endogenously expressed target sequences, the proportion of these sequences in comparison to the proportion of the sequence of interest produced by transfected cells is such that the sorter is able to discriminate the two cell types.

The expression level of an ENaC subunit may vary from cell or cell line to cell or cell line. The expression level in a cell or cell line also may decrease over time due to epigenetic events such as DNA methylation and gene silencing and loss of transgene copies. These variations can be attributed to a variety of factors, for example, the copy number of the transgene taken up by the cell, the site of genomic integration of the transgene, and the integrity of the transgene following genomic integration. One may use FACS or other cell sorting methods (i.e., MACS) to evaluate expression levels. Additional rounds of introducing signaling probes may be used, for example, to determine if and to what extent the cells remain positive over time for any one or more of the RNAs for which they were originally isolated.

Figure 2:
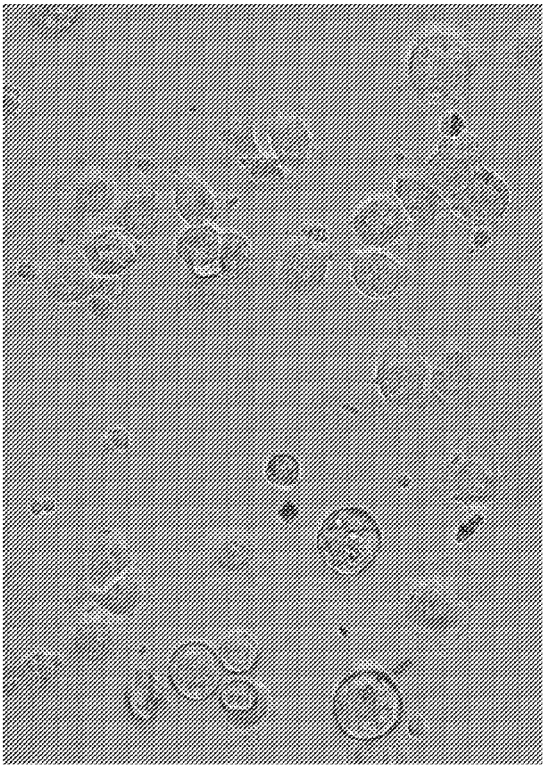
FIG. 2 ENaC induces cell swelling.
Figure 2:
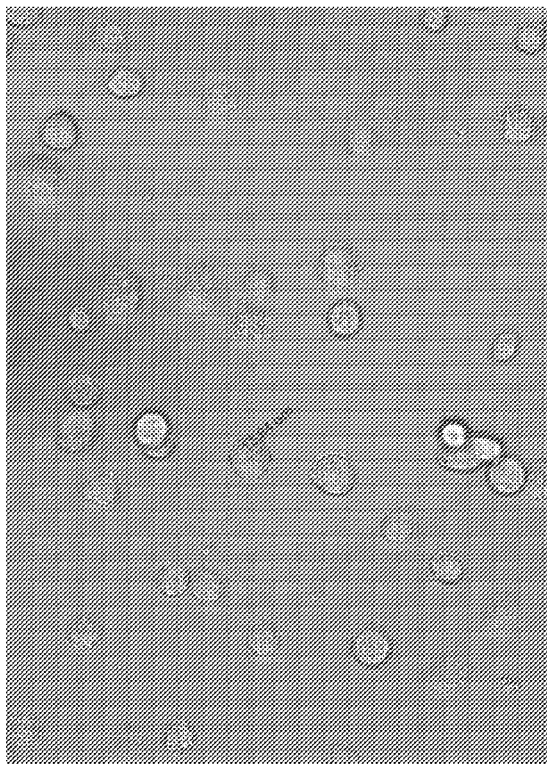

In a further aspect of the invention, we discovered a novel method for producing stable, viable ENaC expressing cells. Cells engineered to express ENaC demonstrated increased cell death compared to control cells (FIG. 1), indicating that ENaC expression has a cytotoxic effect. The cells also appeared swollen compared to control cells (FIG. 2). Without being bound by theory, ENaC expressing cells may take up an amount of sodium ions that disrupts the osmotic gradient, causing increased water uptake and potential swelling and cell bursting. This cytotoxicity could explain why ENaC expressing cell lines have heretofore not been producible. To overcome this newly recognized problem, we identified modified culture media (with reduced ion conductance) that produced viable ENaC expressing cells with normal morphology. According to the invention, ENaC expressing cells are preferably grown in cell culture media that has been modified to reduce ion conductance by ENaC.

In a first embodiment, ion conductance is reduced by reducing ion concentrations (e.g., sodium) in the media. According to the invention, sodium concentration in media is optimized for a particular cell because cells vary in their genetic background and thus respond to sodium concentrations in different ways. Accordingly, to produce an ENaC cell or cell line of the invention, cells are grown in various media with several different concentrations of sodium (ranging from 9 mM to 300 mM). Different types of host cells, as well as different cells within one type of host cell, may be grown in media with different concentrations of sodium. Growing a variety of cells of the invention in media with different concentrations of sodium allows for production and selection of cells that are viable and stably express ENaC. The cells and cell lines of the invention may be cultured in various media with modified sodium concentrations at different times during the process of generating the cells or cell lines, including before transfection, between transfection and sorting, during sorting, during maintenance of the cells or cell lines after sorting, or any combination thereof. In some embodiments, the sodium ion concentration in the culture media is reduced. Culture media with reduced sodium can have a sodium concentration of about 140 mM, about 130 mM, about 120 mM, about 110 mM, about 100 mM, about 90 mM, about 80 mM, about 70 mM, about 60 mM, about 50 mM, about 40 mM, about 30 mM, about 20 mM, 10 mM, about 9 mM or less, or any concentration in between. In some embodiments, cells that tolerate sodium concentration in the media of 150 mM or greater are identified. In order to maintain osmolarity, the culture media of the ENaC expressing cells and cell lines of the invention may have their sodium ions replaced with other cations. Non-limiting examples of such cations include ammonium, lithium, choline, and cesium. One skilled in the art will recognize appropriate sodium ion replacements for culture media. Ion conductance also may be reduced by adding an ENaC antagonist or inhibitor (e.g., amiloride) to normal or reduced sodium cell culture media. One skilled in the art will understand that different concentrations of antagonists/inhibitors may be used depending on the type of antagonist/inhibitor used and depending on the ion concentration in the media. In some embodiments, an ENaC antagonist or inhibitor and/or one or more protease inhibitors may be added to the media.

Once cells expressing ENaC are isolated, they may be cultured in the modified media with their respective different sodium concentrations for a length of time sufficient to produce and identify those stably expressing all three subunits. In one embodiment, isolated cells may be grown individually or pooled to give rise to populations of cells. Individual or multiple cells or cell lines may also be grown separately or pooled. If a pool of cells or cell lines is producing a desired activity, it can be further fractionated until the cell or cell line or set of cells or cell lines having this effect is identified. This may make it easier to maintain large numbers of cells and cell lines without the requirements for maintaining each separately.

A further advantageous property of the ENaC cells and cell lines of the invention is that they stably express at least one alpha or one delta, at least one beta and at least one gamma subunit in the absence of drug selection pressure. Thus, in preferred embodiments, cells and cell lines of the invention are maintained in culture without any selective drug. In further embodiments, cells and cell lines are maintained without any antibiotics. As used herein, cell maintenance refers to culturing cells after they have been selected as described above for their ENaC expression. Maintenance does not refer to the optional step of growing cells in a selective drug (e.g., an antibiotic) prior to cell sorting where drug resistance marker(s) introduced into the cells allow enrichment of stable transfectants in a mixed population.

Drug-free cell maintenance provides a number of advantages. For examples, drug-resistant cells do not always express the co-transfected transgene of interest at adequate levels, because the selection relies on survival of the cells that have taken up the drug resistant gene, with or without the transgene. Further, selective drugs are often mutagenic or otherwise interfere with the physiology of the cells, leading to skewed results in cell-based assays. For example, selective drugs may decrease susceptibility to apoptosis (Robinson et al., 1997), increase DNA repair and drug metabolism (Deffie et al., 1988), increase cellular pH (Thiebaut et al., 1990; Roepe et al., 1993; Simon et al., 1994), decrease lysosomal and endosomal pH (Schindler et al., 1996; Altan et al., 1998), decrease plasma membrane potential (Roepe et al., 1993), increase plasma membrane conductance to chloride (Gill et al., 1992) and ATP (Abraham et al., 1993), and increase rates of vesicle transport (Altan et al., 1999). Thus, the cells and cell lines of this invention allow screening assays that are free from any artifact caused by selective drugs. In some preferred embodiments, the cells and cell lines of this invention are not cultured with selective drugs such as antibiotics before or after cell sorting, so that cells and cell lines with desired properties are isolated by sorting, even when not beginning with an enriched cell population.

In another aspect, the invention provides methods of using the cells and cell lines of the invention. The cells and cell lines of the invention may be used in any application for which functional ENaC subunits, ENaC ion channels or proteolyzed forms of ENaC are needed. The cells and cell lines may be used, for example, but not limited to, in an in vitro cell-based assay or an in vivo assay where the cells are implanted in an animal (e.g., a non-human mammal) to, e.g., screen for ENaC modulators; produce protein for crystallography and binding studies; and investigate compound selectivity and dosing, receptor/compound binding kinetic and stability, and effects of receptor expression on cellular physiology (e.g., electrophysiology, protein trafficking, protein folding, and protein regulation). The cells and cell lines of the invention also can be used in knock down studies to study the roles of specific ENaC subunits.

Cells and cell lines expressing various combinations of subunits can be used separately or together to identify ENaC modulators, including those specific for a particular ENaC or a particular subunit or proteolytic isoform of ENaC and to obtain information about the activities of individual subunits or proteolytic isoforms. The present cells and cell lines may be used to identify the roles of different forms of ENaC in different ENaC pathologies by correlating the identity of in vivo forms of ENaC with the identify of known forms of ENaCs or proteolyzed ENaCs based on their response to various modulators. This allows selection of disease- or tissue-specific ENaC modulators for highly targeted treatment of such ENaC-related pathologies.

Modulators include any substance or compound that alters an activity of ENaC, an ENaC subunit or a proteolytic isoform of ENaC. The modulator can be an ENaC agonist (potentiator or activator) or antagonist (inhibitor or blocker), including partial agonists or antagonists, selective agonists or antagonists and inverse agonists, and can be an allosteric modulator. A substance or compound is a modulator even if its modulating activity changes under different conditions or concentrations or with respect to different forms (i.e., proteolyzed forms) of ENaC. In other aspects, a modulator may change the ability of another modulator to affect the function of an ENaC. For example, a modulator of a form of ENaC that is not inhibited by amiloride may render that form of ENaC susceptible to inhibition by amiloride.

To identify an ENaC modulator, one can expose a novel cell or cell line of the invention to a test compound under conditions in which the ENaC would be expected to be functional and then detect a statistically significant change (e.g., $p<0.05$) in ENaC activity compared to a suitable control, e.g., cells that are not exposed to the test compound. Positive and/or negative controls using known agonists or antagonists and/or cells expressing different combinations of ENaC subunits or proteolytic isoforms may also be used. In some embodiments, the ENaC activity to be detected and/or measured is membrane depolarization, change in membrane potential, or fluorescence resulting from such membrane changes. One of ordinary skill in the art would understand that various assay parameters may be optimized, e.g., signal to noise ratio.

The invention also provides methods of identifying modulators specific for particular enzymatically modified (e.g., proteolyzed, phosphorylated, dephosphorylated, acetylated, ubiquitinated, SUMOylated, glycosylated, methylated, myrstiolated, or fanesylated) forms of ENaC to determine the tissue specificity of different ENaC enzymatically modified forms. Such information may be useful in identifying the relevant enzymatically modified forms of ENaC implicated in ENaC pathologies, (i.e., pathologies related to ion conductance through various ENaC channels) and selecting tissue specific compounds for the selective treatment of such pathologies or for the development of related compounds useful in those treatments.

In some embodiments, one or more cells or cell lines of the invention are exposed to a plurality of test compounds, for example, a library of test compounds. A library of test compounds can be screened using the cell lines of the invention to identify one or more modulators. The test compounds can be chemical moieties including small molecules, polypeptides, peptides, peptide mimetics, antibodies or antigen-binding portions thereof. In the case of antibodies, they may be non-human antibodies, chimeric antibodies, humanized antibodies, or fully human antibodies. The antibodies may be intact antibodies comprising a full complement of heavy and light chains or antigen-binding portions of any antibody, including antibody fragments (such as Fab and Fab, Fab', F(ab')$_2$, Fd, Fv, dAb and the like), single chain antibodies (scFv), single domain antibodies, all or an antigen-binding portion of a heavy chain or light chain variable region.

In some embodiments, prior to exposure to a test compound, the cells or cell lines of the invention may be modified by pretreatment with, for example, enzymes, including mammalian or other animal enzymes, plant enzymes, bacterial enzymes, protein modifying enzymes and lipid modifying enzymes. Such enzymes can include, for example, kinases, proteases, phosphatases, glycosidases, oxidoreductases, transferases, hydrolases, lyases, isomerases, ligases and the like. For example, in some embodiments, cells and cell lines are pretreated with at least one proteolytic enzyme such as trypsin or furin. Alternatively, the cells and cell lines may be exposed to the test compound first followed by treatment to identify compounds that alter the modification of the ENaC by the treatment.

In some embodiments, large compound collections are tested for ENaC modulating activity in a cell-based, functional, high-throughput screen (HTS), e.g., using 384 well format. In some embodiments, a test compound or multiple test compounds including a library of test compounds may be screened using more than one cell or cell line of the invention. If multiple cells or cell lines, each expressing a different naturally occurring or enzymatically modified ENaC molecule, are used, one can identify modulators that are effective on multiple ENaC isoforms or alternatively, modulators that are specific for a particular ENaC and that do not modulate other ENaC isoforms. In the case of a cell or cell line of the invention that expresses a human ENaC, one can expose the cells to a test compound to identify a compound that modulates ENaC activity (either increasing or decreasing) for use in the treatment of disease or condition characterized by undesired ENaC activity, or the decrease or absence of desired ENaC activity. Further, according to the methods of the invention, cells or cell lines of the invention can be used to identify compounds or substances that potentiate or inhibit salt taste for use in ingestible substances.

These and other embodiments of the invention may be further illustrated in the following non-limiting Examples.

EXAMPLES

Example 1

Generating Cells Expressing ENaC Alpha, Beta and Gamma Subunits

Transfection

¶ Transfected cells were grown for at least one week, preferably at least 2 weeks prior to the addition of signaling probes. During the growth period, cells were transferred into four groups, each group with a different sodium concentration (approximately 50, 75, 90, 150 mM Na) to ensure that at least one group had optimal conditions for the experiment. Also during the growth period, antibiotics were added to the media (150 µg/ml Hygromycin, 500 µg/ml G418 and 5 µg/ml Puromycin). Following antibiotic selection, cells were passaged 1 to 10 times in the absence of antibiotics to allow time for expression that is not stable over the selected period of time to subside.

Selection of Cells

Cells were harvested and transfected with signaling probes (SEQ ID NO: 16-18). The cells were then dissociated and collected for analysis and sorted using a fluorescence activated cell sorter. Standard analytical methods were used to gate cells fluorescing above background and to isolate cells falling within that defined gate directly into 96-well plates. Cell sorting was operated to deposit one cell only per well.

Target Sequences detected by signaling probes

Target 1

```
                                      (SEQ ID NO: 13)
5'-GTTCTTAAGGCACAGGAACTGGGAC-3' (beta)
```

Target 2

```
5'-GAAGTTAACCCTGTCGTTCTGCGAC-3'       (SEQ ID NO: 14)

(gamma)
```

Target 3

```
5'-GTTCTATAGGGTCTGCTTGTCGCTC-3'       (SEQ ID NO: 15)

(alpha)
```

Signaling Probes
Supplied as 100 µM stocks
Signaling probe 1—binds (Target 1)

```
                                      (SEQ ID NO: 16)
5'-Cy5GCCAGGTCCCAGTTCCTGTGCCTTAAGAACCTCGC BHQ3 quench-3'
```

Signaling probe 2 —binds (Target 2)

```
                                      (SEQ ID NO: 17)
5'-Cy5.5 GCGAGTCGCAGAACGACAGGGTTAACTTCCTCGC BHQ3 quench-3'
```

Note that BHQ3 could be substituted with BHQ1 or a gold particle in Probe 1 or Probe 2.
Signaling probe 3 —binds (Target 3)

```
                                      (SEQ ID NO: 18)
5'-Fam GCGAGAGCGACAAGCAGACCCTATAGAACCTCGC BHQ1 quench-3'
```

Note that BHQ1 could be substituted with BHQ2 or Dabcyl in Probe 3.

Sorted cells were maintained in media groups as described above. Cells were maintained and were passaged as needed to prevent overconfluence.

Various cell properties were observed while the cells were growing and being passaged in their respective media. For example, cell adherence, viability and fragility (e.g., whether debris remained in media after passaging) were observed using optical microscopy. One cell line was selected with cells that were viable, adhered to the wells and were not fragile was a cell line that was derived from CHO cells that were transfected with all three ENaC subunits and maintained in media containing 90 mM sodium.

Example 2

Preparing Reduced Sodium Media

In initial experiments, we discovered that cells were dying and those that remained alive were enlarged. To generate viable cells with normal morphology that stably express ENaC, we grew ENaC expressing cells in media with various concentrations of sodium (ranging from 50 mM to 150 mM). We prepared these various media with differing sodium concentrations by combining two different stock media (complete media and choline chloride media) in various ratios.

We prepared "Complete media" as follows: we supplemented Nutrient Mixture F-12 HAM (Sigma N4888) with 10% Fetal Bovine Serum (Sigma F2442), 1% L-Glutamine (Sigma G7513), 1% HEPES (Sigma H0887) and 1% MEM Amino Acids (Sigma M7145). For a drug containing version, we added Hygromycin (150 µg/ml), G418 (500 µg/ml) and Puromycin (5 µg/ml).

We prepared a "Choline Chloride Media" as follows: To 500 ml of sterile deionized (DI) water in a 1L beaker we added the following components, followed by an additional 500 ml of DI water and filtered:

| Component | g/L |
|---|---|
| CaCl2•2H2O | 0.265 |
| MgSO4 (anhyd) | 0.09767 |
| KCl | 0.4 |
| Choline Chloride | 14.3 |
| Choline Bicarbonate | 9.1 ml |
| Phenol Red | 0.0159 |
| L-Glutamine 200 mM | 20 ml |
| D-glucose solution 45% | 10 ml |
| HEPES 1M | 10 ml |
| 12.5X BME* | 80 ml |
| 500X vitamin solution** | 2 ml |
| 0.01 g/ml Fe(NO3)3.9H2O*** | 10 µl |

*To prepare 12.5X BME, we added the following to 100 ml of BME 50X solution: L-cysteine HCl (0.018 g), Glycine (0.0375 g), L-Histidine HCl monohydrate (0.0125 g), L-Serine (0.0525 g), L-Proline (0.043 g).
**To prepare 500X Vitamin Solution we added the following to 50 ml sterile DI water and filtered: Choline Chloride (0.1 g), Folic Acid (0.1 g), myo-Inositol (0.18 g), Nicotinamide (0.1 g), DL-Pantothenic Acid hemicalcium salt (0.1 g), Pyridoxine HCl (0.1 g), Riboflavin (0.01 g), Thiamine HCl (0.1 g).
***To prepare 0.01 g/ml Fe(NO3) 3.9 H2O we added 0.1 g of Fe(NO3)3.9H2O to 10 ml sterile DI water and filtered.

For various "low-sodium media", we combined Complete media and Choline Chloride media in varying ratios such that the concentration of sodium and the concentration of choline totaled 150 mM. Although those of skill in the art will understand from this disclosure how to prepare media with a range of sodium concentrations, by way of example, to make 90 mM sodium media, we combined 300 ml of Complete media, 180 ml Choline Chloride media, 20 ml Fetal bovine Serum, 2 ml 100×MEM Nonessential amino acid and 2 ml 100× Proline (3.4 g/L of proline diluted with Choline Chloride media). For drug containing low-sodium media, antibiotics were added to final concentrations of 150 Hygromycin, 500 µg/ml G418 and 5 µg/ml Puromycin. Those of skill in the art will recognize that ions other than choline may be used to produce low-sodium media. For example, we also successfully used N-methyl-D-glucamine (NMDG) to substitute NaCl in media.

Example 3

Characterization of the Stable ENaC Expressing Cell Line

1. Confirmation and Quantification of Gene Expression.

Expression of the mRNAs encoding the three ENaC subunits was confirmed for the top responding ENaC clones by TaqMan and endpoint RT-PCR methods. Total RNA was extracted from the ENaC cell line for TaqMan analysis of gene expression using PRE-DEVELOPED TAQMAN GENE EXPRESSION ASSAY (Applied Biosystems). Relative expression levels over control cells are presented in FIG. 3B.

Heterologous expression of the mRNAs encoding the three ENaC subunits was also confirmed by cell sorting using a FACS machine. Relative expression levels over control cells are presented in FIG. 3A.

2. Membrane Potential Assay

The influx of positively-charged sodium ions following the activation of ENaC results in a change in the membrane potential of the cell. To test the activity of ENaC cell lines, we used a membrane potential assay. Such assays are well known in the art. See, e.g., Zheng, W. et al., *Assays and Drug Development Technologies*, 2:543-553 (2004); A. S. Waggoner, *Annu. Rev. Biophys. Bioeng*, 8:47-68 (1979); Zochowski, M. et al., *Biol. Bull*. 198:1-21 (2000).

Figure 3:
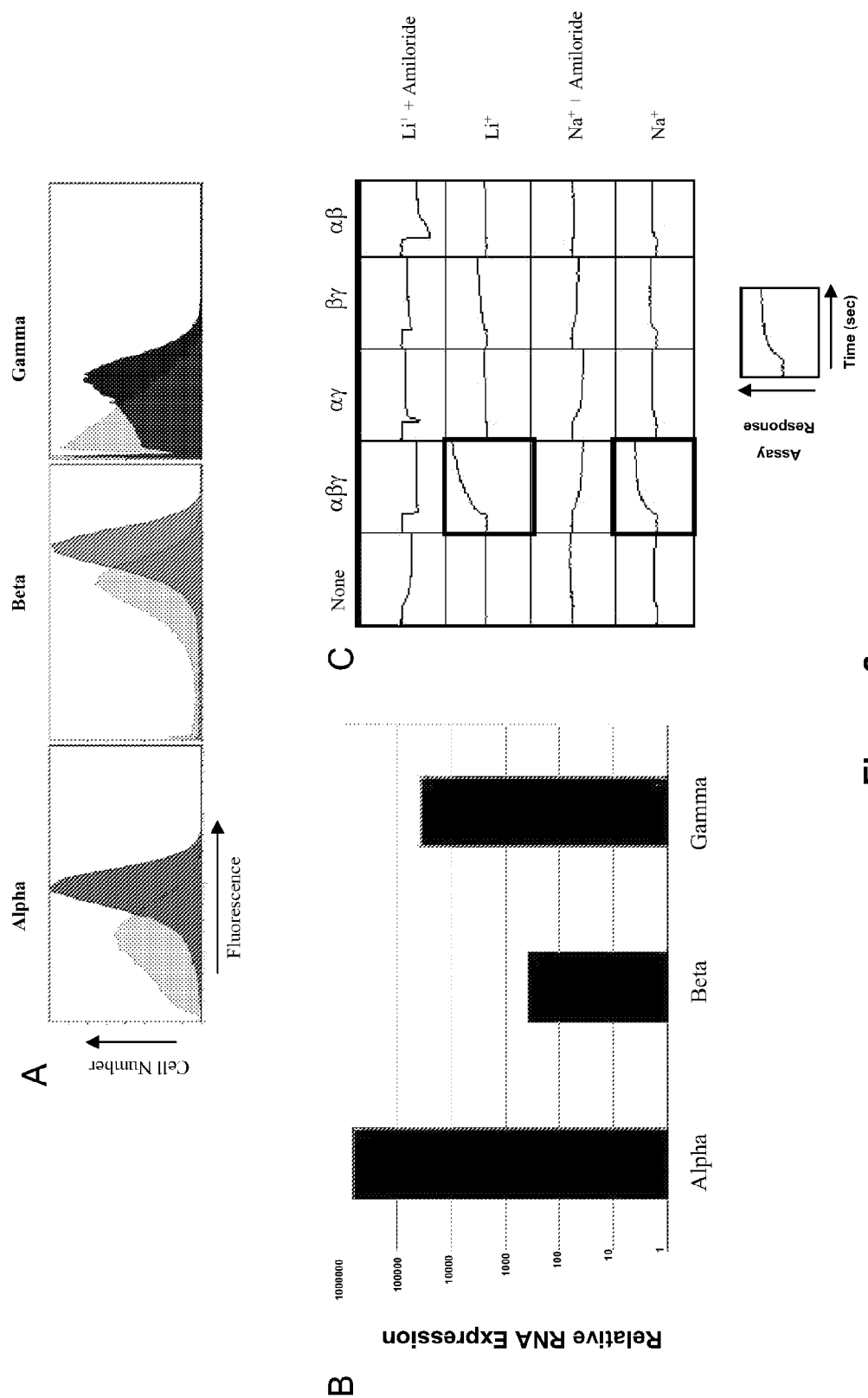
FIG. 3 Characterization of a stable ENaC cell line.

ENaC is an ion channel composed of alpha, beta and gamma subunits. We compared the activities of ENaC cell lines using transient transfection assays. As shown in FIG. 3C, the activity of untransfected cells ("None"), cells transfected with all three ENaC subunits, and cells transfected with any combination of only two subunits was compared. Only cells transfected with all three subunits reported sodium uptake when exposed to 150 mM sodium.

We generated the ENaC expressing cell line from ENaC expressing cells that were transfected and grown in media with reduced sodium ion concentration, such as 90 mM sodium. We maintained the ENaC cell line both in media with 150 mM sodium media as well as in 90 mM sodium media. We characterized cells of the ENaC cell line maintained under both these conditions for their ability to conduct sodium ions, their ability to conduct lithium ions, and their inhibition with amiloride. As shown in Table 1, cells grown in complete media have EC50 and 1050 values that are significantly different from physiological ENaC values, while cells grown in reduce sodium media are physiologically and pharmacologically relevant. We also observed that the addition of antibiotics were required to maintain the consistency of the functional response of the ENaC cell line over time when the cells were maintained in 150 mM sodium media but not when they were maintained in 90 mM sodium media. These results demonstrated that a number of characteristics of the cells of the ENaC cell line are different when the cells are maintained in 90 mM versus 150 mM media. Only cells maintained in the 90 mM sodium media demonstrated ENaC activity or function that was stable, physiologically and pharmacologically relevant, due to e.g. differences in the characteristics of the cells including host genome organization and gene expression in the different media conditions.

TABLE 1

|  | 150 mM Media | 90 mM Media |
| --- | --- | --- |
| NaCl EC50 (approx) | 80 mM | 48 mM |
| LiCl EC50 (approx) | 82 mM | 33 mM |
| Amiloride IC50 (approx) | 11.0 uM | 0.64 uM |

3. Determination of Z' Value for ENaC Cell-Based Assay

The Z' value for the optimized ENaC assay was calculated to achieve a value of 0.85, a surprisingly high value for a membrane potential assay expressing a previously intractable heteromultimeric ion channel target with associated cytotoxicity.

Figure 4:
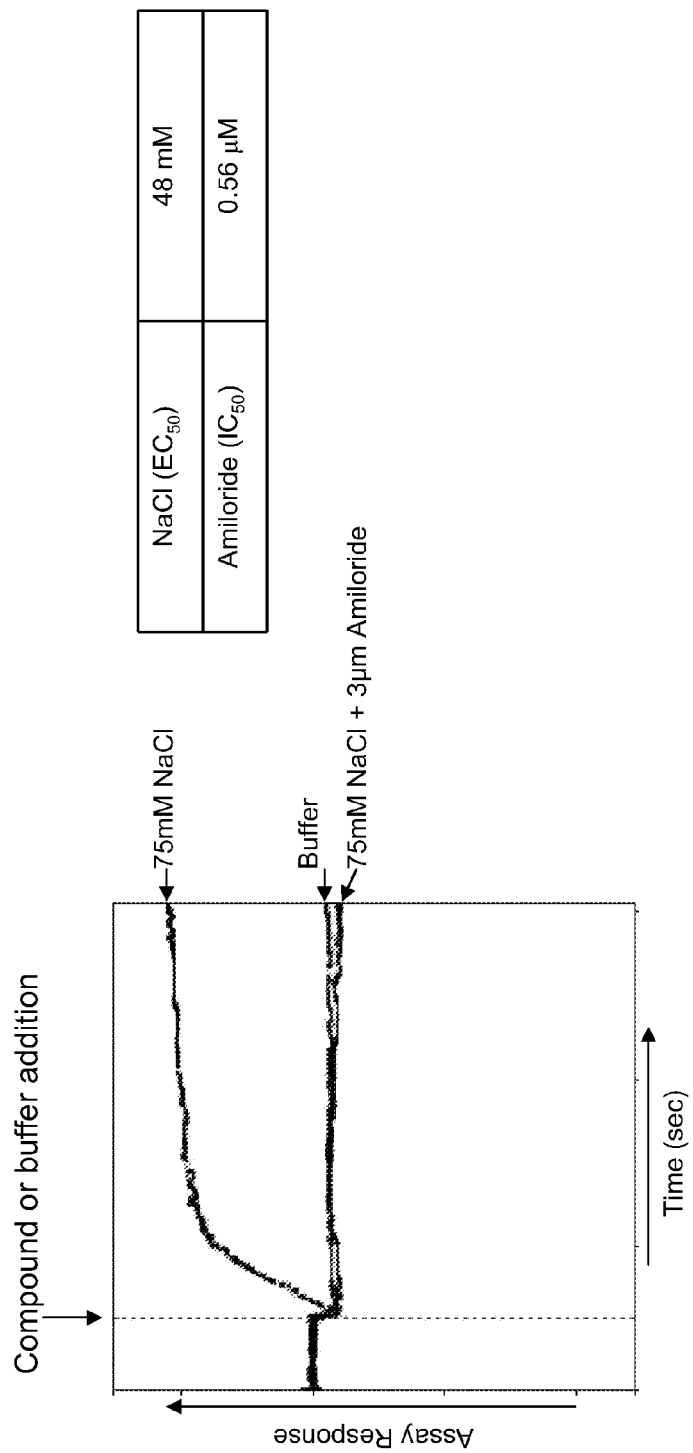
FIG. 4 Response of an ENaC cell line in a functional assay.

As shown in FIG. 4, testing of the cell line expressing ENaC in the membrane potential assay showed activation by sodium, and the sodium uptake was reduced, as expected, with amiloride, a known ENaC blocker. The EC50 value for sodium (48 mM) and the IC50 value for amiloride (0.56 µM) were consistent with reported values for ENaC. For the ENaC cell line, essentially all of the sodium response was blocked by amiloride. This was an important result to confirm that the assay responses are ENaC-specific. These data indicate that the ENaC expressing cells of the present invention are physiologically and pharmacologically relevant.

Figure 5:
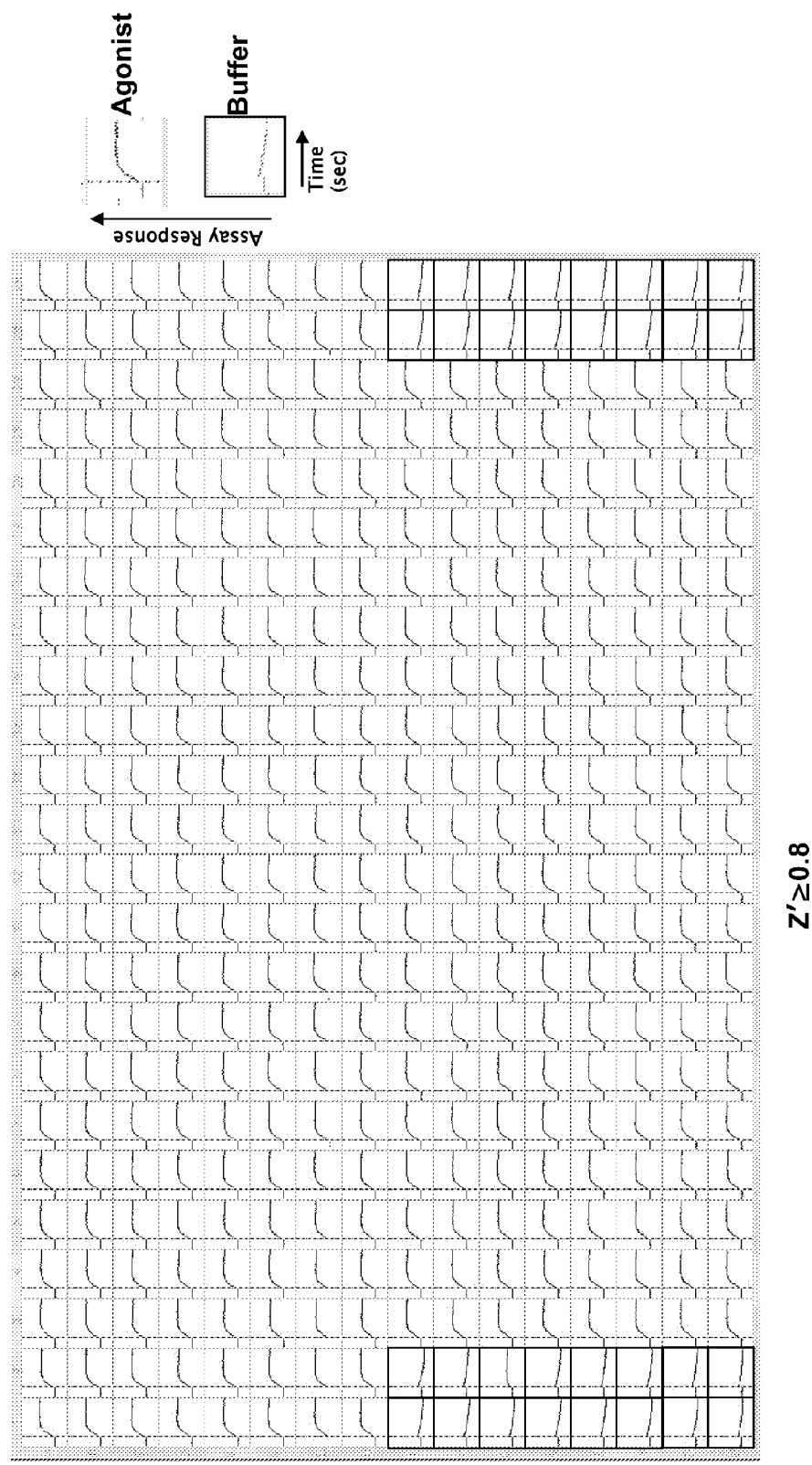
FIG. 5 Assay Consistency.

In order to test the reproducibility of the cell lines of the invention, the line was plated onto a 384-well plate and tested for its ability to conduct sodium. The cells were exposed to NaCl or buffer alone, and sodium uptake was measured and Z' value was determined. FIG. 5 demonstrates that the cells of each well of the 384-well plate responded similarly to sodium stimulation. A Z' value of 0.85 was calculated, indicating that the cells of the invention demonstrate high reproducibility.

Example 4

High Throughput Screening and Identification of ENaC Modulators

Assay Buffer—Phosphate

| Chemical | Final Concentration |
| --- | --- |
| CaCl2•2H20 | 1.939 mM |
| KCl | 5.365 mM |
| KH2P04 | 441 µM |
| MgCl2•6H20 | 492 µM |
| MgS04•7H20 | 406 µM |
| Na2HP04 | 338.5 µM |
| Glucose | 5.549 mM |
| HEPES | 20 mM |
| NaCl | 25 mM |
| Choline Chloride | 125 mM |

Add components to 500 ml water and bring up to 1 L pH to 7.4

ENaC High-Throughput Screening Assay Protocol

On the day before assay, we harvested the cells from stock plates into 90 mM sodium media with no antibiotics and plated $1.5 \times 10^4$ cells in 50 µl into black clear-bottom 384 well assay plates (Coring 3712). The assay plates were maintained in a 37° C. cell culture incubator under 5% CO2 for 19-21 hours. The media was then removed from the assay plates and 20 µl blue membrane potential dye (Molecular Devices Inc) was added and the cells were incubated for 1 hr at room temperature. Test compounds were solubilized in dimethylsulfoxide, diluted in a phosphate buffer and loaded into 384 well polypropylene micro-titer plates. The cell and compound plates were loaded into an FDSS instrument (Hamamatsu) which measures fluorescence (relative fluorescence units) from the plates over time. Fluorescence values were continuously collected from the beginning of the experiment and following addition of test compounds to report baseline values and any changes due to the addition of test compounds. Test compounds in assay buffer or assay buffer alone were then added to the cells and flluorescence values were collected for two minutes. A solution of sodium chloride in assay buffer with reduced choline chloride was then added to the cells to raise the final sodium concentration by 75 mM. The activity of the compound was determined by measuring the change in fluorescence produced following the compound's addition to the cells and/or following subsequent sodium addition.

Figure 6:
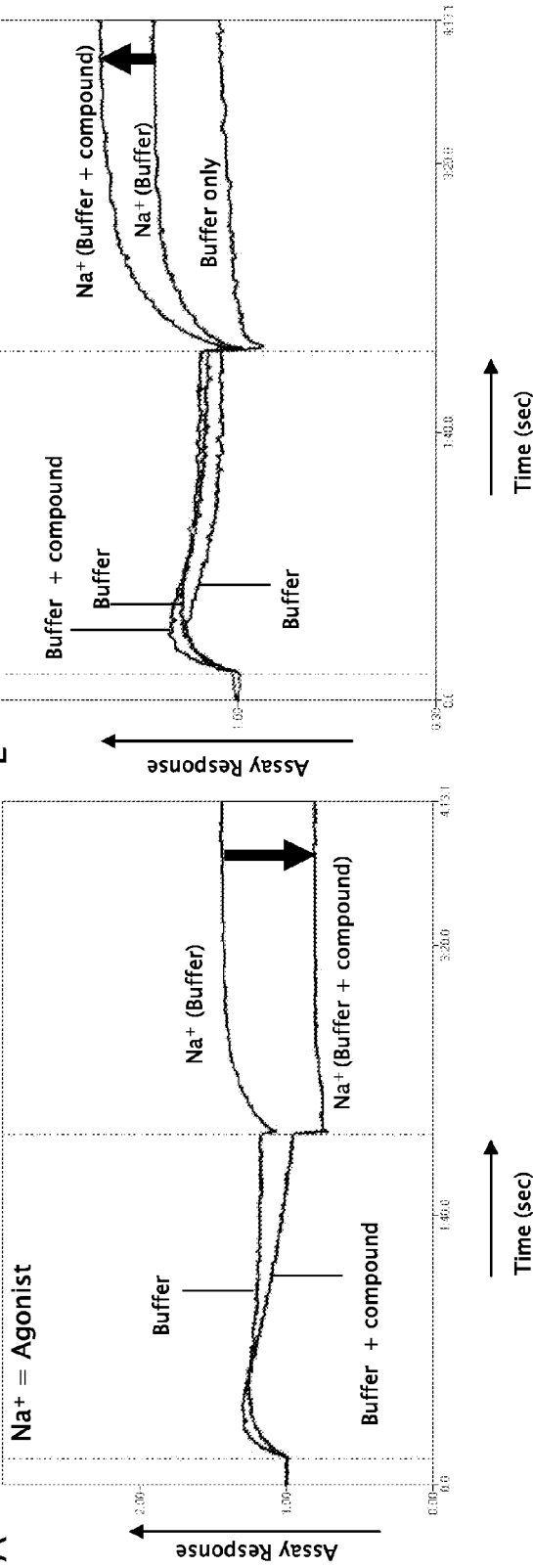
FIG. 6 Identification of Novel ENaC Modulators

The high-throughput screening assay described above was used with a library of compounds to identify several novel ENaC blockers. Unexpectedly, several ENaC potentiators, no examples of which had been previously reported, were also identified in the high-throughput screening assay. FIG. 6 demonstrates representative traces for both an ENaC inhibitor (left panel) and an ENaC potentiator (right panel). These data demonstrate that the ENaC expressing cells of the present invention are well suited for high-throughput screening. The cells of the present invention may also be used in high-throughput screening at the beginning of a drug candidate study to identify promising lead compounds.

Example 5

Enzymatically Modified Isoforms of ENaC

ENaC Isoform Specific High-Throughput Screening Assay Protocol

To investigate the effect of protease treatment on ENaC activity, we conducted the membrane potential assay as described in Example 3 above using a blue membrane potential (MBP) dye solution containing protease (trypsin) at a concentration that does not produce cell detachment. After a 1 hour incubation with a dye-protease solution at room temperature, the assay was run using the FDSS (Hamamatsu Corporation) as described above.

The experiment was performed using several treatment groups, each receiving a different concentration of trypsin (0 to 3 mg/ml). The cells were incubated with the trypsin for 1 hour at room temperature concurrently with membrane potential dye (standard protocol). Following incubation, the ion flux in response to challenge with sodium or sodium+amiloride was reported with the standard two step membrane potential FDSS protocol. Signal (RFU) values were indicated at each dose of protease tested, averaged over nine independent experiments. As shown in FIG. 7A, we were able to distinguish twenty-four proteolytically modified forms (twenty-five including the untreated form) with different activities, indicated by the peaks, valleys, and plateaus. We further characterized these proteolytically modified isoforms for their ability to conduct sodium. FIG. 7B demonstrates that each ENaC cleavage isoform has a unique capacity for sodium conductance. These data indicate that proteolytic cleavage of ENaC generates isoforms with pharmacologically distinct profiles (Table 2). Table 2 shows concentrations of trypsin at which different proteolyzed forms of ENaC have been defined.

TABLE 2

| Isoform | [Trypsin]mg/ml | Amiloride IC50 (approx.) |
|---|---|---|
| Form 1 | 0.000025 | 5.6 |
| Form 2 | 0.001250 | NA |
| Form 3 | 0.001438 | 8.4 |
| Form 4 | 0.002500 | NA |

TABLE 2-continued

| Isoform | [Trypsin]mg/ml | Amiloride IC50 (approx.) |
|---|---|---|
| Form 5 | 0.004140 | 11.9 |
| Form 6 | 0.005000 | 54.3 |
| Form 7 | 0.008280 | 4.7 |
| Form 8 | 0.011500 | NA |
| Form 9 | 0.016500 | 8.7 |
| Form 10 | 0.023000 | NA |
| Form 11 | 0.035100 | 1.2 |
| Form 12 | 0.046875 | NA |
| Form 13 | 0.066250 | 16.3 |
| Form 14 | 0.093750 | 0.44 |
| Form 15 | 0.187500 | 1.3 |
| Form 16 | 0.225000 | 0.82 |
| Form 17 | 0.420000 | 6.2 |
| Form 18 | 0.562500 | 0.41 |
| Form 19 | 0.600000 | 2.4 |
| Form 20 | 0.750000 | NA |
| Form 21 | 0.940000 | 6.1 |
| Form 22 | 1.200000 | NA |
| Form 23 | 1.680000 | 2.1 |
| Form 24 | 2.250000 | NA |

Figure 8:
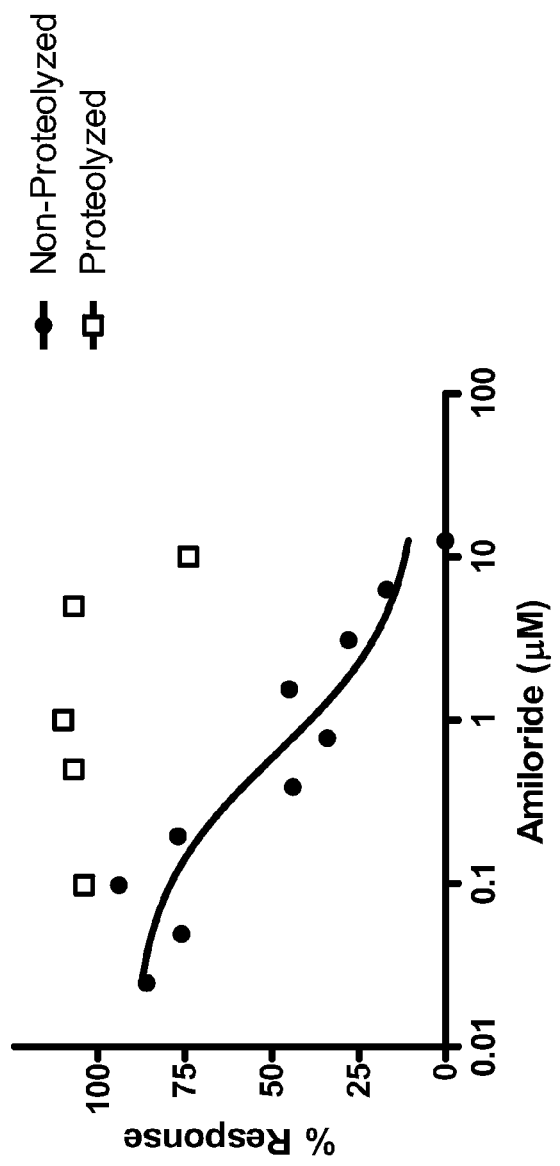
FIG. 8 Amiloride selectively inhibits the non-proteolyzed form of ENaC compared to one of the proteolyzed forms of ENaC (ENaC-P).

We further characterized the effect of amiloride on the proteolytically cleaved ENaC cells. The isoform specific assay described above was performed with MBP dye solution with trypsin concentrations as listed (Table 2). The cells were then exposed to sodium and subsequently to increasing doses of amiloride. 1050 values (Table 2) demonstrate that amiloride was variably effective at inhibiting some of the cleaved ENaC forms. 1050 values were not calculated for a subset of the forms where amiloride was not effective as a blocker at the concentrations tested ("NA"). FIG. 8 demonstrates that amiloride effectively inhibits uncleaved ENaC, but is much less effective or not effective at inhibiting the cleaved ENaC form 24. These data confirm that ENaC cleavage isoforms are differentially inhibited.

Figure 9:
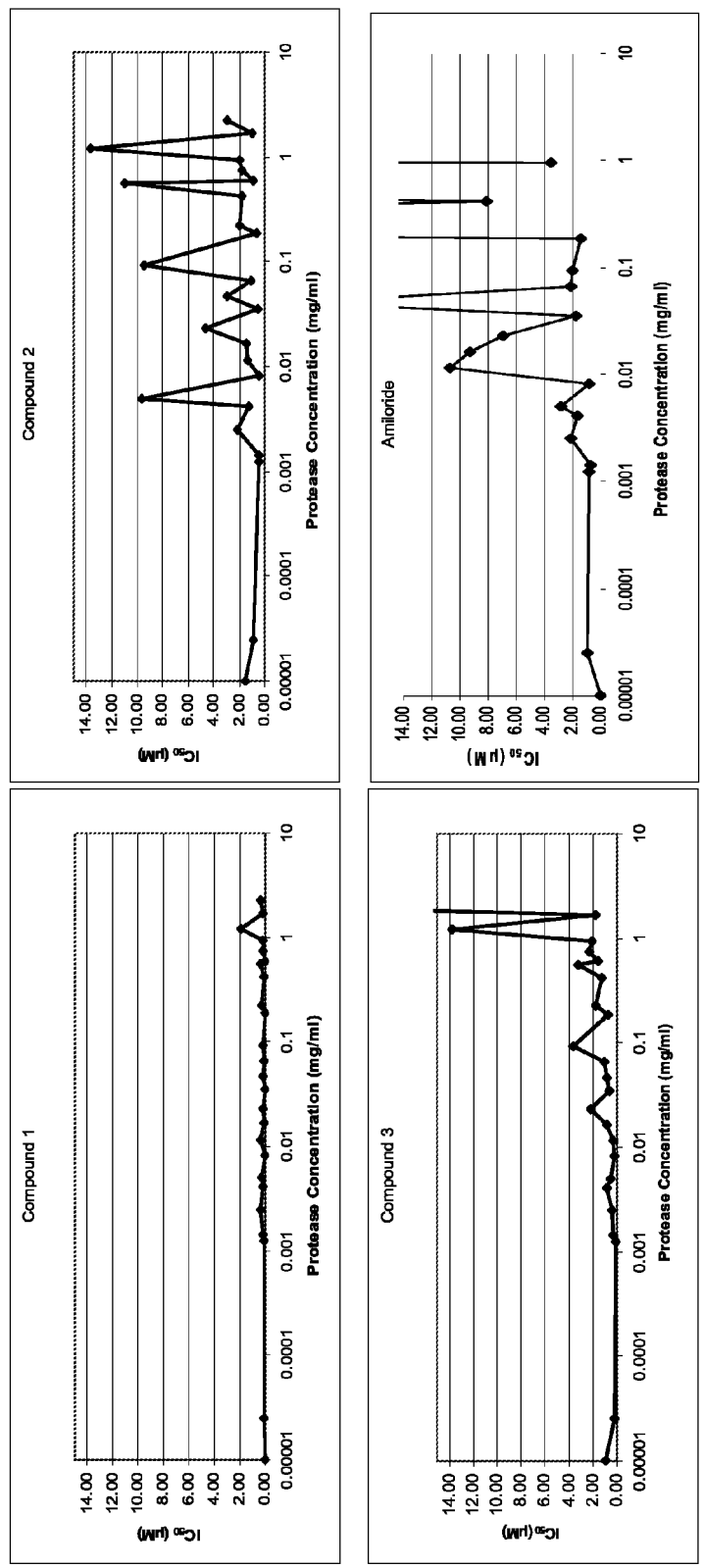
FIG. 9 Proteolyzed forms of ENaC are differentially blocked by different compounds including amiloride (Form 24).

We also tested the ability of novel ENaC inhibitors (identified in Example 4) to inhibit proteolytically cleaved ENaC. As described above, this experiment was performed using several treatment groups, each receiving a different concentration of trypsin (0 to 2.25 mg/ml). The cells were loaded with membrane potential dye concurrently with the trypsin. The cells were incubated with the trypsin for 1 hour at room temperature and assayed for activity with sodium alone or with sodium and an inhibitor. Dose response studies of Amiloride, as well as three compounds identified by the high-throughput screen, were performed at the end of the dye loading incubation in the standard two step membrane potential FDSS protocol. 1050 values were calculated and plotted as a function of protease concentration. FIG. 9 demonstrates that proteolytically cleaved ENaC has variable sensitivity to inhibitory compounds. For instance, compound 1 (top left panel) is capable of inhibiting nearly all ENaC isoforms, while compound 2 (top right panel), compound 3 (bottom left panel), and amiloride (bottom right panel) each inhibit a unique subset of ENaC isoforms. These data further confirm that ENaC cleavage isoforms are differentially inhibited and indicate that the ENaC cells of the present invention can be used to identify isoform specific modulators of ENaC. The different isoforms of ENaC can be pursed in drug discovery to more effectively address the role of the different isoforms of ENaC or the effect or role of proteolysis in disease.

Example 6

Confirmation of ENaC Modulators by Ussing Chamber Analysis

We verified compounds identified using ENaC cell lines of the invention in a high-throughput screening membrane potential assay (with and without protease treatment), in an independent functional assay using human primary epithelial cells in an Ussing Chamber assay as follows. Human primary epithelial cells express endogenous ENaC and, thus, permit a comparison of the activity of ENaC in a cell or cell line of the invention with the activity of endogenously expressed ENaC.

Cells

Primary human bronchial epithelial (HBE) cells (Lonza) were cultured in bronchial epithelial cell growth medium supplemented with bovine pituitary extract, hydrocortisone, human recombinant epidermal growth factor, epinephrine, transferrin (10 µg/ml), insulin (5 µg/ml), retinoic acid, triiodothyronine, gentamicin, and amphotericin B according to manufacturer's instructions. The medium was changed every 3 days until the cells were 90% confluent. The cells were then passaged and seeded onto Snapwell culture inserts in differentiation medium containing 50% DMEM in bronchial epithelial cell growth medium with the supplements described above, but without triiodothyronine and at a final retinoic acid concentration of 50 nM (all-trans-retinoic acid; Sigma). Cells were seeded at a density of $1 \times 10^4$ cells/$cm^2$ onto 1.12-$cm^2$ Snapwell (Costar) inserts. HBE cells were maintained submerged for the first 7 days in culture; then they were exposed to an air-liquid interface for the remainder of the culture period. At all stages of culture, cells were maintained at 37° C. in 5% $CO_2$ in an air incubator. Four HBE cell donors were used for these studies.

Transepithelial Measurements

HBE cells on culture inserts were rinsed, mounted in an EasyMount Chamber System (Physiologic Instruments) and bathed with continuously gassed Ringer solution (5% $CO_2$ in $O_2$, pH 7.4) maintained at 37° C. containing (in mM) 120 NaCl, 25 $NaHCO_3$, 3.3 $KH_2PO_4$, 0.8 $K_2HPO_4$, 1.2 $CaCl_2$, 1.2 $MgCl_2$, and 10 glucose (all from Sigma). Electrodes [agar bridged (4% in 1 M KCl) Ag—AgCl] were used and the inserts were voltage clamped to 0 mV. Transepithelial current, voltage and resistance were measured every 10 seconds for the duration of the experiment. Membranes with a resistance of <200 mOhms were discarded. The test compounds identified above were added to the apical surface of the membrane. All dosing was cumulative (final concentrations of compounds: 0.5 uM, 1 uM, 4.33 uM, 10 uM). Membranes receiving vehicle only were used as a control.

10 µM amiloride was added towards the end of the experiment, in order to determine the magnitude of the ENaC current.

Figure 10:
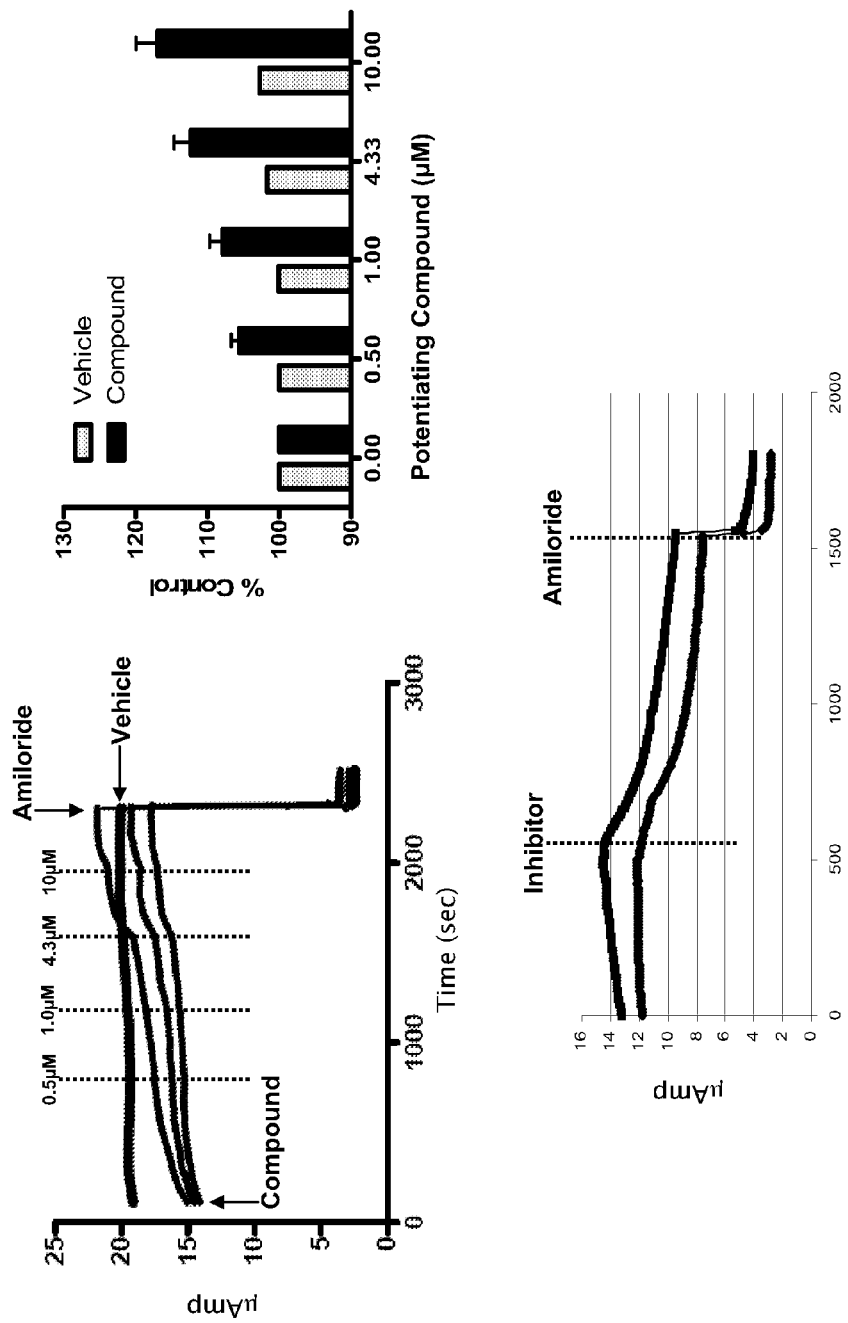
FIG. 10 High-Throughput screening data confirmed by Ussing Chamber assays.

As shown in FIG. 10, the Ussing chamber assay confirmed the activity of both the positive (upper panels) and negative (lower panel) modulators that were identified using an ENaC cell line of the invention in the ENaC HTS assay, including compounds that were identified by their selective activation of protease-treatment enzymatically modified ENaC isoforms.

Example 7

Taste Test Confirmation of Potentiators

To confirm the activity of ENaC potentiators identified using an ENaC cell line of the invention in the ENaC high-throughput screening assay, we conducted a standard "sip and spit" taste test. Tasters are screened for acuity and descriptive capabilities. All have been trained to detect and quantify taste perception. Briefly, subjects performed blind taste testing of a salt solution alone or with two different concentrations (5 and 10 ppm) of a test compound. Panelists are presented with coded paired samples labeled A and B. Each pair consists of a reference solution (salt solution alone) and a test solution (salt solution plus potentiator). Test solutions contain potentiator compounds at either of the two different concentrations. Subjects are asked to taste both samples and select the sample that tastes more salty. At least three out of four times, solutions containing the potentiator compound were detected as saltier than the solution alone.

Figure 11:
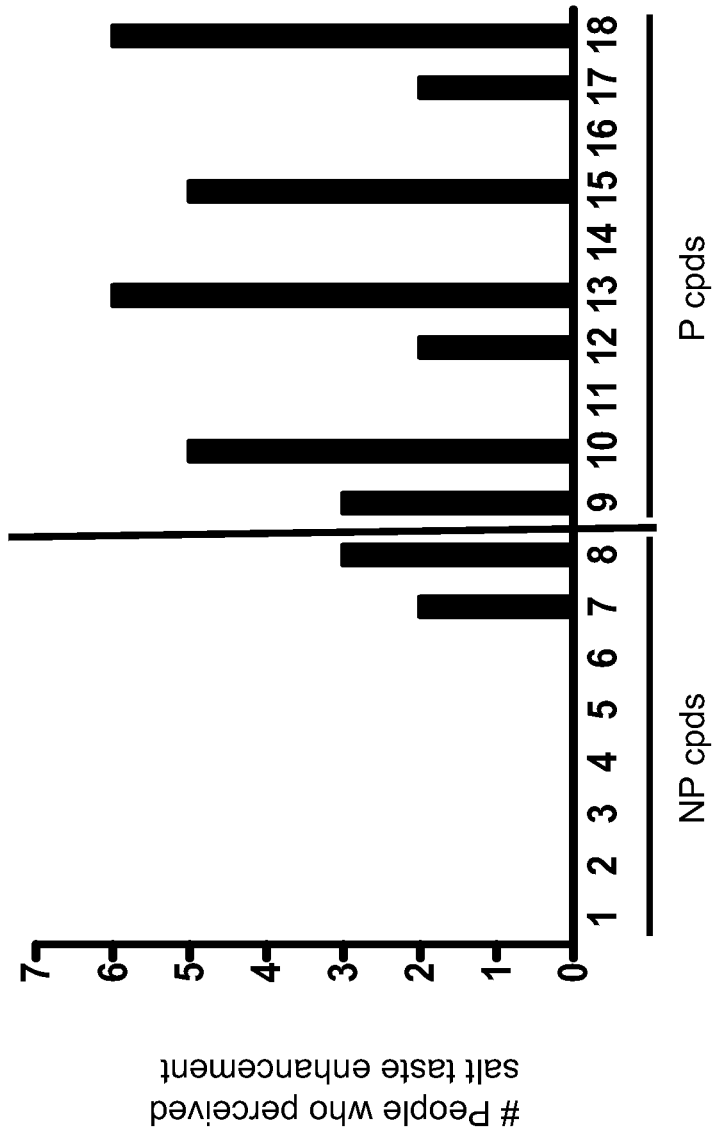
FIG. 11 Taste testing of compounds that selectively potentiate either the non-proteolyzed (NP) or one proteolyzed (P) form of ENaC.

Taste testing was used to assess the effect of potentiator compounds on salt taste. This included a set of compounds (P) that were active at the most highly proteolyzed form but not the non-proteolyzed form, as well as a set of compounds (NP) active at the non-proteolyzed form but not the most highly proteolyzed form. As shown in FIG. 11, on average the P compounds were more effective at potentiating salt taste than the NP compounds. These data are consistent with the presence of proteases in the oral cavity, and demonstrate that the cleaved isoforms of ENaC play a major role in detecting salty taste as well as or in addition to the non-cleaved isoform. By confirming the activity of the novel potentiators identified in Example 3, these data also confirm that the ENaC expressing cells of the present invention can be used in a high-throughput screening assay to identify novel modulators of ENaC activity.

What is claimed is:

1. A stably transfected engineered cell line, or a cell from the cell line, stably expressing:
   a) an epithelial sodium channel (ENaC) alpha or delta subunit,
   b) an ENaC beta subunit, and
   c) an ENaC gamma subunit;
   wherein the cell line, or the cell from the cell line, maintains, for at least one week, the ability to produce a Z' value of at least 0.3 in a membrane potential dye assay using NaCl as an agonist.

2. The cell or cell line of claim 1, wherein at least one subunit is expressed from:
   a) an introduced nucleic acid encoding the at least one subunit;
   b) an endogenous nucleic acid by engineered gene activation; or
   c) both a) and b).

3. The cell or cell line of claim 1, wherein the cell or the cells in the cell line:
   a) is a eukaryotic cell or are eukaryotic cells, respectively;
   b) does not/do not express ENaC endogenously absent any engineering, respectively; or
   c) the combination of (a) and (b).

4. The cell or cell line of claim 1, wherein the cell is a CHO cell or the cells in the cell line are CHO cells.

5. The cell or cell line of claim 1, wherein the cell or the cells in the cell line forms/form polarized monolayers.

6. The cell or cell line of claim 1, wherein the ENaC:
   a) is mammalian;
   b) comprises subunits from different species;
   c) comprises one or more subunits that are chimeric;
   d) is proteolyzed; or
   e) any combination of (a)-(d).

7. The cell or cell line of claim 1, wherein the cell or cell line maintains, for at least one week, the ability to produce a Z' value of 0.5-0.6 in a membrane potential dye assay using NaCl as an agonist.

8. The cell or cell line of claim 1, which stably expresses ENaC in culture media without antibiotics.

9. The cell or cell line of claim 1, wherein the ENaC alpha subunit is selected from the group consisting of:
   a) an ENaC alpha polypeptide comprising the amino acid sequence set forth in SEQ ID NO: 7, SEQ ID NO: 10, SEQ ID NO: 19, SEQ ID NO: 20, or SEQ ID NO: 21;
   b) an ENaC alpha polypeptide comprising an amino acid sequence that is at least 95% identical to the amino acid sequence of any one of SEQ ID NOS: 7, 10, 19, 20 and 21;

c) an ENaC alpha polypeptide encoded by a nucleic acid that hybridizes under stringent conditions to any one of SEQ ID NOS: 1, 4 and 22, wherein the stringent conditions comprise hybridization in 6X SSC at about 45° C., followed by at least one wash in 0.2X SSC, 0.1% SDS at 60° C.; and d) an ENaC alpha polypeptide that is an allelic variant of any one of SEQ ID NOS: 7, 10, 19, 20 and 21.

10. The cell or cell line of claim 1, wherein the ENaC alpha subunit is encoded by a nucleic acid selected from the group consisting of:
  a) a nucleic acid comprising the nucleotide sequence set forth in SEQ ID NO: 1, SEQ ID NO: 4, or SEQ ID NO: 22;
  b) a nucleic acid that hybridizes to a nucleic acid comprising the nucleotide sequence of any one of SEQ ID NOS: 1, 4, and 22 under stringent conditions, wherein the stringent conditions comprise hybridization in 6X SSC at about 45° C., followed by at least one wash in 0.2X SSC, 0.1% SDS at 60° C.;
  c) a nucleic acid that encodes a polypeptide comprising the amino acid sequence of any one of SEQ ID NOS: 7, 10, 19, 20 and 21;
  d) a nucleic acid comprising a nucleotide sequence that is at least 95% identical to any one of SEQ ID NOS: 1, 4 and 22; and
  e) a nucleic acid that is an allelic variant of any one of SEQ ID NOS: 1, 4 and 22.

11. The cell or cell line of claim 1, wherein the ENaC beta subunit is selected from the group consisting of:
  a) an ENaC beta subunit polypeptide that comprises the amino acid sequence set forth in SEQ IDNO: 8 or SEQ ID NO: 11;
  b) an ENaC beta subunit polypeptide that comprises an amino acid sequence that is at least 95% identical to the amino acid sequence of any one of SEQ ID NOS: 8 and 11;
  c) an ENaC beta subunit polypeptide encoded by a nucleic acid that hybridizes under stringent conditions to a nucleic acid comprising the nucleotide sequence of any one of SEQ ID NOS: 2, 5 and 23, wherein the stringent conditions comprise hybridization in 6X SSC at about 45° C., followed by at least one wash in 0.2X SSC, 0.1% SDS at 60° C.; and
  d) an ENaC beta subunit polypeptide that is an allelic variant of any one of SEQ ID NOS: 8 and 11.

12. The cell or cell line of claim 1, wherein the ENaC beta subunit is encoded by a nucleic acid selected from the group consisting of:
  a) a nucleic acid comprising the nucleotide sequence set forth in SEQ ID NO: 2, SEQ ID NO: 5, or SEQ ID NO: 23;
  b) a nucleic acid that hybridizes to any one of SEQ ID NOS: 2, 5 and 23 under stringent conditions, wherein the stringent conditions comprise hybridization in 6X SSC at about 45° C., followed by at least one wash in 0.2X SSC, 0.1% SDS at 60° C.;
  c) a nucleic acid that encodes the polypeptide of any one of SEQ ID NOS: 8 and 11;
  d) a nucleic acid comprising a nucleotide sequence that is at least 95% identical to any one of SEQ ID NOS: 2, 5 and 23; and
  e) a nucleic acid that is an allelic variant of any one of SEQ ID NOS: 2, 5 and 23.

13. The cell or cell line of claim 1, wherein the ENaC gamma subunit is selected from the group consisting of:
  a) an ENaC gamma subunit polypeptide comprising the amino acid sequence set forth in SEQ ID NO: 9 or SEQ ID NO: 12;
  b) an ENaC gamma subunit polypeptide comprising an amino acid sequence that is at least 95% identical to any one of SEQ ID NOS: 9 and 12;
  c) an ENaC gamma subunit polypeptide encoded by a nucleic acid that hybridizes under stringent conditions to a nucleic acid comprising the nucleotide sequence of any one of SEQ ID NOS: 3, 6 and 24, wherein the stringent conditions comprise hybridization in 6X SSC at about 45° C., followed by at least one wash in 0.2X SSC, 0.1% SDS at 60° C.; and
  d) an ENaC gamma subunit polypeptide that is an allelic variant of SEQ ID NOS: 9 or 12.

14. The cell or cell line of claim 1, wherein the ENaC gamma subunit is encoded by a nucleic acid selected from the group consisting of:
  a) a nucleic acid comprising the nucleotide sequence set forth in SEQ ID NO: 3, SEQ ID NO: 6 or SEQ ID NO: 24;
  b) a nucleic acid that hybridizes to a nucleic acid comprising the nucleotide sequence of any one of SEQ ID NOS: 3, 6 and 24 under stringent conditions, wherein the stringent conditions comprise hybridization in 6X SSC at about 45° C., followed by at least one wash in 0.2X SSC, 0.1% SDS at 60° C.;
  c) a nucleic acid that encodes the polypeptide of SEQ ID NOS: 9 or 12;
  d) a nucleic acid with at least 95% sequence identity to any one of SEQ ID NOS: 3, 6 and 24; and
  e) a nucleic acid that is an allelic variant of any one of SEQ ID NOS: 3, 6 and 24.

15. The cell or cell line of claim 1, wherein the ENaC delta subunit is encoded by a nucleic acid selected from the group consisting of:
  a) a nucleic acid comprising the nucleotide sequence set forth in SEQ ID NO: 25;
  b) a nucleic acid that hybridizes to SEQ ID NO: 25 under stringent conditions, wherein the stringent conditions comprise hybridization in 6X SSC at about 45° C., followed by at least one wash in 0.2X SSC, 0.1% SDS at 60° C.;
  c) a nucleic acid with at least 95% sequence identity to SEQ ID NO: 25; and
  d) a nucleotide that is an allelic variant of any one of SEQ ID NO: 25.

16. The cell or cell line of claim 1, wherein the cell or cell line has been treated with a protease or a protease inhibitor.

17. The cell or cell line of claim 16, wherein said protease is trypsin.

18. The cell or cell line of claim 1, wherein at least one ENaC subunit is a proteolyzed subunit.

19. The cell or cell line of claim 3, wherein the cell or the cells in the cell line is/are mammalian cells.

20. The cell or cell line of claim 6, wherein the ENaC:
  a) is human;
  b) comprises subunits from different species;
  c) comprises one or more subunits that are chimeric;
  d) is proteolyzed;
  e) any combination of (b)-(d); or
  f) the combination of (a) and (d).

21. The cell or cell line of claim 1, wherein the cell or the cells in the cell line is/are mammalian cells.

22. The cell or cell line of claim 1, wherein the ENaC is human.

23. The cell line of claim 1, wherein the cell or cell line maintains, for at least one week, the ability to produce a Z' value of 0.7-0.8 in a membrane potential dye assay using NaCl as an agonist.

24. The cell line of claim 1, wherein the cell or cell line maintains, for at least one week, the ability to produce a Z' value of at least 0.7 in a membrane potential dye assay using NaCl as an agonist.

25. The cell or cell line of claim 1, wherein the cell or cell line maintains the ability to produce the Z' value for four or more weeks.

26. A method for producing the cell line of claim 1 comprising the steps of:
  (a) introducing a first vector comprising a nucleic acid encoding an ENaC alpha or delta subunit, a second vector comprising a nucleic acid encoding an ENaC beta subunit and a third vector comprising a nucleic acid encoding an ENaC gamma subunit into a host cell;
  (b) introducing, a first molecular beacon that detects the expression of the ENaC alpha or delta subunit, a second molecular beacon that detects the expression of the ENaC beta subunit and a third molecular beacon that detects the expression of the ENaC gamma subunit, into the host cell produced in step (a);
  (c) isolating a cell that expresses the ENaC alpha or delta subunit, the ENaC beta subunit and the ENaC gamma subunit; and
  (d) generating a cell line from the cell isolated in step (c).

27. The method of claim 26 wherein the isolating utilizes a cell sorter.

28. The method of claim 27, wherein the cell sorter is a flow cytometric cell sorter, a fluorescence-activated cell sorter or a magnetic cell sorter.

29. A method for identifying a modulator of an ENaC function comprising the step of exposing at least one cell line of claim 1 to a test compound and detecting a change in the ENaC function.

30. The method of claim 29, wherein the detecting step utilizes a membrane potential assay, electrophysiology assay, a binding assay or an Ussing chamber assay.

31. The method of claim 29, wherein the modulator is selected from the group consisting of an ENaC inhibitor, an ENaC antagonist, an ENaC agonist or an ENaC potentiator.

32. The method of claim 29, wherein the test compound is a small molecule, a chemical moiety, a polypeptide, or an antibody.

33. The method of claim 29, wherein the test compound is a library of compounds.

34. The method of claim 33, where the library is a small molecule library, a combinatorial library, a peptide library or an antibody library.

35. The method of claim 29, wherein the modulator is selective for an enzymatically modified form of ENaC.

36. The method of claim 29, wherein the cells are grown in reduced sodium media.

37. The method of claim 36, wherein the sodium concentration in the media is between 9 and 150 mM sodium.

38. The method of claim 36, wherein the sodium concentration in the media is between 40 and 120 mM sodium.

39. A method for producing a cell comprising an enzymatically modified form of ENaC, comprising the step of exposing a cell from the cell line of claim 1 to at least one protease, wherein at least one enzymatically modified form of ENaC is generated.

* * * * *